US012648705B2

(12) United States Patent (10) Patent No.: US 12,648,705 B2
Weinstein et al. (45) Date of Patent: Jun. 9, 2026

(54) SYSTEMS, DEVICES AND METHODS FOR RADIO FREQUENCY-BASED PHYSIOLOGICAL MONITORING OF PATIENTS

(71) Applicant: Zoll Medical Israel Ltd., Kfar-Saba (IL)

(72) Inventors: Uriel Weinstein, Mazkeret Batya (IL); Rafi Ravid, Savyon (IL)

(73) Assignee: ZOLL Medical Israel Ltd., Kfar-Saba (IL)

( * ) Notice: Subject to any disclaimer, the term of this patent is extended or adjusted under 35 U.S.C. 154(b) by 1198 days.

(21) Appl. No.: 16/364,548

(22) Filed: Mar. 26, 2019

(65) Prior Publication Data

US 2019/0298208 A1 Oct. 3, 2019

Related U.S. Application Data

(60) Provisional application No. 62/650,706, filed on Mar. 30, 2018.

(51) Int. Cl.
A61B 5/024 (2006.01)
A61B 5/00 (2006.01)
(Continued)

(52) U.S. Cl.
CPC ...... A61B 5/02444 (2013.01); A61B 5/02116 (2013.01); A61B 5/02405 (2013.01);
(Continued)

(58) Field of Classification Search
CPC . A61B 5/02444; A61B 5/361; A61B 5/02116; A61B 5/02405; A61B 5/6805;
(Continued)

(56) References Cited

U.S. PATENT DOCUMENTS 4,240,445 A 12/1980 Iskander et al.
4,344,440 A 8/1982 Aaby et al.
(Continued)

FOREIGN PATENT DOCUMENTS

CN 101032400 A 9/2007
CN 101516437 A 8/2009
(Continued)

OTHER PUBLICATIONS

Extended Search Report for European Application No. 19776258.6, date of mailing, Dec. 13, 2021, 9 pages.
(Continued)

*Primary Examiner* — Charles A Marmor, II
*Assistant Examiner* — Meghan R Kumar
(74) *Attorney, Agent, or Firm* — The Webb Law Firm

(57) ABSTRACT

Some embodiments of the current disclosure are directed toward physiological monitoring systems, devices and methods for implementation as wearable and/or wireless sensor(s) and to be used in aiding clinicians in the diagnosis and identification of various clinical conditions, events and/or trends. The systems and devices include an RF device configured to transmit radio-frequency (RF) waves towards an artery located within a tissue of a patient or a subject and to receive reflected RF waves from the artery. In some embodiments, the reflected RF waves are analyzed to determine various physiological conditions of the subject including but not limited to blood pressure, heart rate, arrhythmic events, and/or the like.

20 Claims, 24 Drawing Sheets

(51) Int. Cl.

| | |
|---|---|
| *A61B 5/021* | (2006.01) |
| *A61B 5/0507* | (2021.01) |
| *A61B 5/361* | (2021.01) |
| *A61B 5/363* | (2021.01) |

(52) U.S. Cl.
CPC ............ *A61B 5/361* (2021.01); *A61B 5/6805* (2013.01); *A61B 5/681* (2013.01); *A61B 5/746* (2013.01); *A61B 5/0507* (2013.01); *A61B 5/363* (2021.01); *A61B 5/6823* (2013.01); *A61B 5/6824* (2013.01); *A61B 5/6831* (2013.01); *A61B 5/6833* (2013.01)

(58) Field of Classification Search
CPC ....... A61B 5/681; A61B 5/746; A61B 5/0507; A61B 5/363; A61B 5/6823; A61B 5/6824; A61B 5/6831; A61B 5/6833; A61B 5/02438; A61B 5/02125
See application file for complete search history.

(56) References Cited

U.S. PATENT DOCUMENTS

| | | | |
|---|---|---|---|
| 4,557,272 A | 12/1985 | Carr | |
| 4,632,128 A | 12/1986 | Paglione et al. | |
| 4,640,280 A | 2/1987 | Sterzer | |
| 4,641,659 A | 2/1987 | Sepponen | |
| 4,774,961 A | 10/1988 | Carr | |
| 4,777,718 A | 10/1988 | Henderson et al. | |
| 4,825,880 A | 5/1989 | Stauffer et al. | |
| 4,926,868 A | 5/1990 | Larsen | |
| 4,945,914 A | 8/1990 | Allen | |
| 4,958,638 A | 9/1990 | Sharpe | |
| 4,986,870 A | 1/1991 | Frohlich | |
| 5,003,622 A | 3/1991 | Ma et al. | |
| 5,109,855 A | 5/1992 | Guner | |
| 5,330,507 A * | 7/1994 | Schwartz | A61N 1/36114 |
| | | | 600/521 |
| 5,394,882 A | 3/1995 | Mawhinney | |
| 5,404,877 A | 4/1995 | Nolan | |
| 5,474,574 A | 12/1995 | Payne et al. | |
| 5,540,727 A | 7/1996 | Tockman et al. | |
| 5,549,650 A | 8/1996 | Bornzin et al. | |
| 5,668,555 A | 9/1997 | Starr | |
| 5,704,355 A | 1/1998 | Bridges | |
| 5,766,208 A | 6/1998 | McEwan | |
| 5,807,257 A | 9/1998 | Bridges | |
| 5,829,437 A | 11/1998 | Bridges | |
| 5,841,288 A | 11/1998 | Meaney et al. | |
| 5,865,177 A | 2/1999 | Segawa | |
| 5,967,986 A | 10/1999 | Cimochowski et al. | |
| 6,019,724 A | 2/2000 | Gronningsaeter et al. | |
| 6,025,803 A | 2/2000 | Bergen et al. | |
| 6,061,589 A | 5/2000 | Bridges et al. | |
| 6,064,903 A | 5/2000 | Riechers et al. | |
| 6,093,141 A | 7/2000 | Mosseri et al. | |
| 6,144,344 A | 11/2000 | Kim | |
| 6,161,036 A | 12/2000 | Matsumara et al. | |
| 6,193,669 B1 | 2/2001 | Degany et al. | |
| 6,208,286 B1 | 3/2001 | Rostislavovich et al. | |
| 6,233,479 B1 | 5/2001 | Haddad et al. | |
| 6,267,723 B1 | 7/2001 | Matsumura et al. | |
| 6,320,547 B1 | 11/2001 | Fathy et al. | |
| 6,330,479 B1 | 12/2001 | Stauffer | |
| 6,409,662 B1 | 6/2002 | Lloyd et al. | |
| 6,454,711 B1 | 9/2002 | Haddad et al. | |
| 6,471,655 B1 | 10/2002 | Baura | |
| 6,480,733 B1 | 11/2002 | Turcott | |
| 6,526,318 B1 | 2/2003 | Ansarinia | |
| 6,592,518 B2 | 7/2003 | Denker et al. | |
| 6,604,404 B2 | 8/2003 | Paltieli et al. | |
| 6,729,336 B2 | 5/2004 | Da Silva et al. | |
| 6,730,033 B2 | 5/2004 | Yao et al. | |
| 6,755,856 B2 | 6/2004 | Fierens et al. | |
| 6,933,811 B2 | 8/2005 | Enokihara et al. | |
| 6,940,457 B2 | 9/2005 | Lee et al. | |
| 7,020,508 B2 | 3/2006 | Stivoric et al. | |
| 7,045,440 B2 | 5/2006 | Huff et al. | |
| 7,122,012 B2 | 10/2006 | Bouton et al. | |
| 7,130,681 B2 | 10/2006 | Gebhardt et al. | |
| 7,184,824 B2 | 2/2007 | Hashimshony | |
| 7,191,000 B2 | 3/2007 | Zhu et al. | |
| 7,197,356 B2 | 3/2007 | Carr | |
| 7,266,407 B2 | 9/2007 | Li et al. | |
| 7,267,651 B2 | 9/2007 | Nelson | |
| 7,272,431 B2 | 9/2007 | McGrath | |
| 7,280,863 B2 | 10/2007 | Shachar | |
| 7,454,242 B2 | 11/2008 | Fear et al. | |
| 7,474,918 B2 | 1/2009 | Frants et al. | |
| 7,479,790 B2 | 1/2009 | Choi | |
| 7,493,154 B2 | 2/2009 | Bonner et al. | |
| 7,529,398 B2 | 5/2009 | Zwirn et al. | |
| 7,570,063 B2 | 8/2009 | Van Veen et al. | |
| 7,591,792 B2 | 9/2009 | Bouton | |
| 7,697,972 B2 | 4/2010 | Verard et al. | |
| 7,719,280 B2 | 5/2010 | Lagae et al. | |
| 7,747,302 B2 | 6/2010 | Milledge et al. | |
| 7,868,627 B2 | 1/2011 | Turkovskyi | |
| 8,032,211 B2 | 10/2011 | Hashimshony et al. | |
| 8,211,040 B2 | 7/2012 | Kojima et al. | |
| 8,217,839 B1 | 7/2012 | Paulsen | |
| 8,295,920 B2 | 10/2012 | Bouton et al. | |
| 8,352,015 B2 | 1/2013 | Bernstein et al. | |
| 8,384,596 B2 | 2/2013 | Rofougaran et al. | |
| 8,473,054 B2 | 6/2013 | Pillai et al. | |
| 8,682,399 B2 | 3/2014 | Rabu | |
| 8,882,759 B2 | 11/2014 | Manley et al. | |
| 8,938,292 B2 | 1/2015 | Hettrick et al. | |
| 8,983,592 B2 | 3/2015 | Belalcazar | |
| 8,989,837 B2 | 3/2015 | Weinstein et al. | |
| 9,220,420 B2 | 12/2015 | Weinstein et al. | |
| 9,265,438 B2 | 2/2016 | Weinstein et al. | |
| 9,572,512 B2 | 2/2017 | Weinstein et al. | |
| 9,629,561 B2 | 4/2017 | Weinstein et al. | |
| 9,788,752 B2 | 10/2017 | Weinstein et al. | |
| 10,136,833 B2 | 11/2018 | Weinstein et al. | |
| 10,548,485 B2 | 2/2020 | Arditi et al. | |
| 10,561,336 B2 | 2/2020 | Rappaport et al. | |
| 10,588,599 B2 | 3/2020 | Weinstein et al. | |
| 10,660,609 B2 | 5/2020 | Weinstein et al. | |
| 10,680,324 B2 | 6/2020 | Weinstein et al. | |
| 11,013,420 B2 | 5/2021 | Ravid et al. | |
| 11,020,002 B2 | 6/2021 | Weinstein et al. | |
| 11,108,153 B2 | 8/2021 | Weinstein et al. | |
| 11,241,158 B2 | 2/2022 | Arditi et al. | |
| 11,259,715 B2 | 3/2022 | Ravid et al. | |
| 2002/0032386 A1 | 3/2002 | Sackner et al. | |
| 2002/0045836 A1 | 4/2002 | Alkawwas | |
| 2002/0049394 A1 | 4/2002 | Roy et al. | |
| 2002/0050954 A1 | 5/2002 | Jeong-Kun et al. | |
| 2002/0147405 A1 | 10/2002 | Denker et al. | |
| 2002/0151816 A1 | 10/2002 | Rich et al. | |
| 2003/0036674 A1 | 2/2003 | Bouton | |
| 2003/0036713 A1 | 2/2003 | Bouton et al. | |
| 2003/0088180 A1 | 5/2003 | Van Veen et al. | |
| 2003/0100815 A1 | 5/2003 | Da Silva et al. | |
| 2003/0199770 A1 | 10/2003 | Chen et al. | |
| 2003/0219598 A1 | 11/2003 | Sakurai | |
| 2004/0015087 A1 | 1/2004 | Boric-Lubecke et al. | |
| 2004/0073081 A1 | 4/2004 | Schramm | |
| 2004/0077943 A1 | 4/2004 | Meaney et al. | |
| 2004/0077952 A1 | 4/2004 | Rafter et al. | |
| 2004/0249257 A1 | 12/2004 | Tupin et al. | |
| 2004/0254457 A1 | 12/2004 | van der Weide | |
| 2004/0261721 A1 | 12/2004 | Steger | |
| 2005/0038503 A1 | 2/2005 | Greenhalgh et al. | |
| 2005/0107693 A1 | 5/2005 | Fear et al. | |
| 2005/0151234 A1 | 7/2005 | Yoshimura | |
| 2005/0192488 A1 | 9/2005 | Bryenton | |
| 2005/0245816 A1 | 11/2005 | Candidus et al. | |
| 2006/0004269 A9 | 1/2006 | Caduff et al. | |
| 2006/0009813 A1 | 1/2006 | Taylor et al. | |
| 2006/0025661 A1 | 2/2006 | Sweeney et al. | |
| 2006/0101917 A1 | 5/2006 | Merkel | |

(56)  References Cited

U.S. PATENT DOCUMENTS

| | | | |
|---|---|---|---|
| 2006/0237223 A1 | 10/2006 | Chen et al. | |
| 2006/0265034 A1 | 11/2006 | Aknine et al. | |
| 2007/0016032 A1 | 1/2007 | Aknine | |
| 2007/0016050 A1 | 1/2007 | Moehring et al. | |
| 2007/0055123 A1 | 3/2007 | Takiguchi | |
| 2007/0100385 A1 | 5/2007 | Rawat | |
| 2007/0123770 A1 | 5/2007 | Bouton et al. | |
| 2007/0123778 A1 | 5/2007 | Kantorovich | |
| 2007/0135721 A1 | 6/2007 | Zdeblick | |
| 2007/0152812 A1 | 7/2007 | Wong et al. | |
| 2007/0156057 A1 | 7/2007 | Cho et al. | |
| 2007/0162090 A1 | 7/2007 | Penner | |
| 2007/0191733 A1 | 8/2007 | Gianchandani et al. | |
| 2007/0263907 A1 | 11/2007 | McMakin et al. | |
| 2008/0027313 A1 | 1/2008 | Shachar | |
| 2008/0030284 A1 | 2/2008 | Tanaka et al. | |
| 2008/0036668 A1 | 2/2008 | White et al. | |
| 2008/0097199 A1 | 4/2008 | Mullen | |
| 2008/0129511 A1 | 6/2008 | Yuen et al. | |
| 2008/0139934 A1 | 6/2008 | McMorrow et al. | |
| 2008/0167566 A1 | 7/2008 | Kamil et al. | |
| 2008/0169961 A1 | 7/2008 | Steinway et al. | |
| 2008/0183247 A1 | 7/2008 | Harding | |
| 2008/0200802 A1 | 8/2008 | Bahavaraju et al. | |
| 2008/0224688 A1 | 9/2008 | Rubinsky et al. | |
| 2008/0269589 A1 | 10/2008 | Thijs et al. | |
| 2008/0283282 A1 | 11/2008 | Kawasaki et al. | |
| 2008/0294036 A1 | 11/2008 | Hoi et al. | |
| 2008/0316124 A1 | 12/2008 | Hook | |
| 2008/0319301 A1 | 12/2008 | Busse | |
| 2009/0021720 A1 | 1/2009 | Hecker | |
| 2009/0048500 A1 | 2/2009 | Corn | |
| 2009/0076350 A1 | 3/2009 | Bly et al. | |
| 2009/0153412 A1 | 6/2009 | Chiang et al. | |
| 2009/0153433 A1 | 6/2009 | Nagai et al. | |
| 2009/0187109 A1 | 7/2009 | Hashimshony | |
| 2009/0203972 A1 | 8/2009 | Heneghan et al. | |
| 2009/0227882 A1 | 9/2009 | Foo | |
| 2009/0240132 A1 | 9/2009 | Friedman | |
| 2009/0240133 A1 | 9/2009 | Friedman | |
| 2009/0240156 A1* | 9/2009 | Fischell | A61B 5/349 |
| | | | 600/509 |
| 2009/0248450 A1 | 10/2009 | Fernandez | |
| 2009/0262028 A1 | 10/2009 | Mumbru et al. | |
| 2009/0281412 A1 | 11/2009 | Boyden et al. | |
| 2009/0299175 A1 | 12/2009 | Bernstein et al. | |
| 2009/0312615 A1 | 12/2009 | Caduff et al. | |
| 2009/0322636 A1 | 12/2009 | Brigham et al. | |
| 2010/0004517 A1 | 1/2010 | Bryenton | |
| 2010/0013318 A1 | 1/2010 | Iguchi et al. | |
| 2010/0052992 A1 | 3/2010 | Okamura et al. | |
| 2010/0056907 A1 | 3/2010 | Rappaport et al. | |
| 2010/0076315 A1 | 3/2010 | Erkamp et al. | |
| 2010/0081895 A1 | 4/2010 | Zand | |
| 2010/0106223 A1 | 4/2010 | Grevious | |
| 2010/0152600 A1 | 6/2010 | Droitcour et al. | |
| 2010/0256462 A1 | 10/2010 | Rappaport et al. | |
| 2010/0265159 A1 | 10/2010 | Ando et al. | |
| 2010/0305460 A1 | 12/2010 | Pinter et al. | |
| 2010/0312301 A1 | 12/2010 | Stahmann | |
| 2010/0321253 A1 | 12/2010 | Ayala Vazquez et al. | |
| 2010/0332173 A1 | 12/2010 | Watson et al. | |
| 2011/0004076 A1 | 1/2011 | Janna et al. | |
| 2011/0009754 A1 | 1/2011 | Wenzel et al. | |
| 2011/0022325 A1 | 1/2011 | Craddock et al. | |
| 2011/0040176 A1 | 2/2011 | Razansky et al. | |
| 2011/0060215 A1 | 3/2011 | Tupin et al. | |
| 2011/0068995 A1 | 3/2011 | Baliarda et al. | |
| 2011/0125207 A1 | 5/2011 | Nabutovsky et al. | |
| 2011/0130800 A1 | 6/2011 | Weinstein et al. | |
| 2011/0257555 A1 | 10/2011 | Banet et al. | |
| 2012/0029323 A1 | 2/2012 | Zhao | |
| 2012/0065514 A1 | 3/2012 | Naghavi et al. | |
| 2012/0068906 A1 | 3/2012 | Asher et al. | |
| 2012/0098706 A1 | 4/2012 | Lin et al. | |
| 2012/0104103 A1 | 5/2012 | Manzi | |
| 2012/0330151 A1 | 12/2012 | Weinstein et al. | |
| 2013/0041268 A1 | 2/2013 | Rimoldi et al. | |
| 2013/0053671 A1 | 2/2013 | Farra | |
| 2013/0069780 A1* | 3/2013 | Tran | A61B 5/021 |
| | | | 340/539.12 |
| 2013/0090566 A1 | 4/2013 | Muhlsteff et al. | |
| 2013/0123614 A1 | 5/2013 | Bernstein et al. | |
| 2013/0184573 A1 | 7/2013 | Pahlevan et al. | |
| 2013/0190646 A1 | 7/2013 | Weinstein et al. | |
| 2013/0225989 A1 | 8/2013 | Saroka et al. | |
| 2013/0231550 A1 | 9/2013 | Weinstein et al. | |
| 2013/0274599 A1 | 10/2013 | Bouton et al. | |
| 2013/0281800 A1 | 10/2013 | Saroka et al. | |
| 2013/0297344 A1 | 11/2013 | Cosentino et al. | |
| 2013/0310700 A1 | 11/2013 | Wiard et al. | |
| 2014/0046690 A1 | 2/2014 | Gunderson et al. | |
| 2014/0081159 A1 | 3/2014 | Tao et al. | |
| 2014/0128032 A1 | 5/2014 | Muthukumar | |
| 2014/0163425 A1 | 6/2014 | Tran | |
| 2014/0251659 A1 | 9/2014 | Asano et al. | |
| 2014/0288436 A1* | 9/2014 | Venkatraman | A61B 5/1118 |
| | | | 600/509 |
| 2015/0018676 A1 | 1/2015 | Barak | |
| 2015/0025333 A1 | 1/2015 | Weinstein et al. | |
| 2015/0150477 A1 | 6/2015 | Weinstein et al. | |
| 2015/0164349 A1* | 6/2015 | Gopalakrishnan | A61B 5/746 |
| | | | 600/508 |
| 2015/0335310 A1 | 11/2015 | Bernstein et al. | |
| 2016/0038048 A1* | 2/2016 | Ting | A61B 5/02405 |
| | | | 600/479 |
| 2016/0073924 A1 | 3/2016 | Weinstein et al. | |
| 2016/0095534 A1 | 4/2016 | Thakur | |
| 2016/0198957 A1 | 7/2016 | Arditi et al. | |
| 2016/0198976 A1 | 7/2016 | Weinstein et al. | |
| 2016/0213321 A1 | 7/2016 | Weinstein et al. | |
| 2016/0317054 A1 | 11/2016 | Weinstein et al. | |
| 2016/0345845 A1* | 12/2016 | Ravid | A61B 5/021 |
| 2017/0035327 A1 | 2/2017 | Yuen et al. | |
| 2017/0135598 A1 | 5/2017 | Weinstein et al. | |
| 2017/0238966 A1 | 8/2017 | Weinstein et al. | |
| 2017/0296093 A1 | 10/2017 | Weinstein et al. | |
| 2019/0046038 A1 | 2/2019 | Weinstein et al. | |
| 2019/0298208 A1 | 10/2019 | Weinstein et al. | |
| 2020/0113447 A1 | 4/2020 | Arditi et al. | |
| 2020/0297309 A1 | 9/2020 | Weinstein et al. | |
| 2020/0381819 A1 | 12/2020 | Weinstein et al. | |
| 2021/0244282 A1 | 8/2021 | Weinstein et al. | |
| 2021/0251507 A1 | 8/2021 | Ravid et al. | |
| 2022/0013899 A1 | 1/2022 | Weinstein et al. | |
| 2022/0192516 A1 | 6/2022 | Arditi et al. | |

FOREIGN PATENT DOCUMENTS

| | | | |
|---|---|---|---|
| DE | 10008886 | | 9/2001 |
| EP | 1834588 | A1 | 9/2007 |
| EP | 2506917 | A1 | 10/2012 |
| EP | 2 602 870 | A1 | 6/2013 |
| JP | 05-038957 | | 5/1993 |
| JP | 10-137193 | A | 5/1998 |
| JP | 2000-235006 | A | 8/2000 |
| JP | 2001-525925 | A | 12/2001 |
| JP | 2002-094321 | | 3/2002 |
| JP | 2003-141466 | | 5/2003 |
| JP | 2004-526488 | A | 9/2004 |
| JP | 2006-208070 | A | 8/2006 |
| JP | 2006-319767 | A | 11/2006 |
| JP | 2007-061359 | A | 3/2007 |
| JP | 2007-149959 | | 6/2007 |
| JP | 2008-515548 | A | 5/2008 |
| JP | 2008-148141 | A | 6/2008 |
| JP | 2008-518706 | A | 6/2008 |
| JP | 2008-530546 | A | 7/2008 |
| JP | 2008-542759 | A | 11/2008 |
| JP | 2008-545471 | | 12/2008 |
| JP | 2009-514619 | A | 4/2009 |
| JP | 2009-522034 | A | 6/2009 |
| JP | 2010-507929 | | 3/2010 |

(56)            References Cited

FOREIGN PATENT DOCUMENTS

| JP | 2010-072957 | | 4/2010 | | |
|----|-------------|---|--------|---|---|
| JP | 2010-512190 | A | 4/2010 | | |
| JP | 2010-530769 | | 9/2010 | | |
| JP | 2010-537766 | A | 12/2010 | | |
| JP | 2011-507583 | A | 3/2011 | | |
| JP | 2011-524213 | A | 9/2011 | | |
| JP | 2012-090257 | | 5/2012 | | |
| WO | WO 02/03499 | A1 | 1/2002 | | |
| WO | WO 2003/009752 | A2 | 2/2003 | | |
| WO | WO 2006/127719 | A2 | 11/2006 | | |
| WO | WO 2006/130798 | A2 | 12/2006 | | |
| WO | WO 2007/017861 | A2 | 2/2007 | | |
| WO | WO 2007/023426 | A2 | 3/2007 | | |
| WO | WO 2008/070856 | A2 | 6/2008 | | |
| WO | WO 2008/148040 | A1 | 12/2008 | | |
| WO | WO 2009/031149 | A2 | 3/2009 | | |
| WO | WO 2009/031150 | A2 | 3/2009 | | |
| WO | WO 2009/060182 | A1 | 5/2009 | | |
| WO | WO 2009/081331 | A1 | 7/2009 | | |
| WO | WO 2009/152625 | A1 | 12/2009 | | |
| WO | WO 2011/067623 | A1 | 6/2011 | | |
| WO | WO 2011/067685 | A1 | 6/2011 | | |
| WO | WO 2011/141915 | A2 | 11/2011 | | |
| WO | WO 2012/011065 | A1 | 1/2012 | | |
| WO | WO 2012/011066 | A1 | 1/2012 | | |
| WO | WO-2013005720 | A1 | 1/2013 | | |
| WO | WO 2013/118121 | A1 | 8/2013 | | |
| WO | WO 2013/121290 | A2 | 8/2013 | | |
| WO | WO 2015/118544 | A1 | 8/2015 | | |
| WO | WO 2016/040337 | A1 | 3/2016 | | |
| WO | WO-2017139922 | A1 * | 8/2017 | ......... | A61B 5/02108 |

OTHER PUBLICATIONS

Lin et al., "Enhanced performances of a compact conical pattern annular-ring patch antenna using a slotted ground plane," Microwave Conference, 2001. APMC 2001. 2001 Asia-Pacific Dec. 3-6, 201, IEEE, vol. 3, Dec. 3, 2001, pp. 1036-1039.

Lin et al., "Using dual-antenna nanosecond pulse near field sensing technology for non-contact and continuous blood pressure measurement", Engineering in Medicine and Biology Society (EMBC), 2013 35th Annual International Conference of the IEEE, IEEE, Aug. 28, 2012 (Aug. 28, 2012), pp. 219-222.

Matsugatani et al., "Surface Wave Distribution Over Electromagnetic Bandgap (EBG) and EBG Reflective Shield for Patch Antenna," IEICE Transactions on Electronics, vol. E88-C, No. 12, Dec. 1, 2005, pp. 2341-2349.

Solberg et al: "A feasibility study on aortic pressure estimation using UWB radar", Ultra-Wideband, 2009. ICUWB 2009. IEEE International Conference on, IEEE, Piscataway, NJ, USA, Sep. 9, 2009 (Sep. 9, 2009), pp. 464-468.

Yang et al., "Reflection phase characterizations of the EBG ground plane for low profile wire antenna applications," IEEE Transactions on Antennas and Propagation, vol. 51, No. 10, Oct. 1, 2003, pp. 2691-2703.

International Search Report and Written Opinion for International Application No. PCT/IL2019/050347, mailed on Jul. 24, 2019, 9 pages.

Zhang et al., "Planar artificial magnetic conductors and patch antennas," IEEE Transactions on Antennas and Propagation, vol. 51, No. 10, Oct. 1, 2003, pp. 2704-2712.

Alekseev, S. I., et al. "Human Skin permittivity determined by millimeter wave reflection measurements", Bioelectromagnetics, vol. 28, No. 5, Jul. 1, 2007, pp. 331-339.

Ascension Technology Corporation, "TrakSTAR Adds Versatility to Ascension's New Product Line: Desktop Model Joins driveBAY Tracker for Fast Guidance of Miniaturized Sensor", USA, Apr. 7, 2008.

Bell et al., "A Low-Profile Achimedean Spiral Antenna Using an EBG Ground Plane", IEEE Antennas and Wireless Propagation Letters 3, pp. 223-226 (2004).

Beyer-Enke et al., Intra-arterial Doppler flowmetry in the superficial femoral artery following angioplasty., 2000, European Radiology, vol. 10, No. 4, p. 642-649.

Claron Technology Inc., "MicronTracker 3: A New Generation of Optical Trackers", Canada, 2009.

Czum et al., "The Vascular Diagnostic Laboratory", The Heart & Vascular Institute Newsletter, vol. 1, USA, Winter, 2001.

Extended Search Report for European Application No. 11809360.8, date of mailing, Mar. 11, 2014.

Ghosh, et al., Immediate Evaluation of Angioplasty and Stenting Results in Supra-Aortic Arteries by Use of a Doppler-Tipped Guidewire, Aug. 2004, American Journal of Neuroradiology, vol. 25, p. 1172-1176.

Gentili et al., "A Versatile Microwave Plethysmograph for the Monitoring of Physiological Parameters", IEEE Transactions on Biomedical Engineering, IEEE Service Center, Pitscataway, NJ, US, vol. 49, No. 10, Oct. 1, 2002.

Haude et al., Intracoronary Doppler-and Quantitative Coronary Angiography-Derived Predictors of Major Adverse Cardiac Events After Stent Implantation, Mar. 6, 2001, Circulation, vol. 103(9), p. 1212-1217.

Immersion Corporation, "Immersion Introduces New 3D Digitizing Product-MicroScribe G2; Faster Data Transfer, USB Compatibility, New Industrial Design", Press Release, San Jose, USA, Jul. 1, 2002.

International Preliminary Report on Patentability, mailed Jan. 31, 2013, for International Application No. PCT/IB2011/053246, 22 pages.

International Preliminary Report on Patentability, dated Aug. 19, 2014 for International Application No. PCT/IB2013/000663 filed Feb. 15, 2013.

International Preliminary Report on Patentability, dated Jun. 5, 2012, for International Application No. PCT/IB2010/054861.

International Preliminary Report on Patentability, mailed Jan. 22, 2013, for International Application No. PCT/IB2011/053244, 6 pages.

International Preliminary Report on Patentability, mailed Jun. 5, 2012, for International Application No. PCT/IB2009/055438.

International Search Report and Written Opinion of the International Searching Authority, mailed Dec. 2, 2011, for International Application No. PCT/IB2011/053244, 7 pages.

International Search Report and Written Opinion, mailed Dec. 13, 2011, for International Application No. PCT/IB2011/053246, 24 pages.

International Search Report and Written Opinion, mailed Feb. 26, 2015, for International Application No. PCT/IL2014/050937.

International Search Report and Written Opinion, mailed Jul. 20, 2010, for International Application No. PCT/IB2009/055438.

International Search Report and Written Opinion, mailed Nov. 26, 2013 for International Application No. PCT/IB2013/000663 filed Feb. 15, 2013.

International Search Report, dated Apr. 5, 2011, for International Application No. PCT/IB2010/054861.

International Search Report and Written Opinion, mailed Nov. 28, 2018 for International Application No. PCT/IL2018/050808 filed Jul. 20, 2018.

Kantarci et al., Follow-Up of Extracranial Vertebral Artery Stents with Doppler Sonography., Sep. 2006, American Journal of Roentgenology, vol. 187, p. 779-787.

Lal et al., "Duplex ultrasound velocity criteria for the stented carotid artery", Journal of Vascular Surgery, vol. 47, No. 1, pp. 63-73, Jan. 2008.

Larsson et al., "State Diagrams of the Heart—a New Approach to Describing Cardiac Mechanics", Cardiovascular Ultrasound 7:22 (2009).

Liang, Jing et al., Microstrip Patch Antennas on Tunable Electromagnetic Band-Gap Substrates, IEEE Transactions on Antennas and Propagation, vol. 57, No. 6, Jun. 2009.

Lin, J.C. et al., "Microwave Imaging of Cerebral Edema", Proceedings of the IEEE, IEEE, NY, US, vol. 70, No. 5; May 1, 1982, pp. 523-524.

Miura et al. "Time Domain Reflectometry: Measurement of Free Water in Normal Lung and Pulmonary Edema," American Journal of Physiology—Lung Physiology 276:1 (1999), pp. L207-L212.

(56)                    References Cited

OTHER PUBLICATIONS

Notice of Reasons for Rejection, mailed Apr. 17, 2015, for JP 2013-520273.
Notice of Reasons for Rejection, mailed Apr. 28, 2014, for JP 2012-541588.
Notice of Reasons for Rejection, mailed Mar. 31, 2015, for JP 2012-541588.
Partial Supplementary Search Report, mailed Oct. 19, 2015, for EP Application No. 13748671.8.
Paulson, Christine N., et al. "Ultra-wideband radar methods and techniques of medical sensing and imaging" Proceedings of Spie, vol. 6007, Nov. 9, 2005, p. 60070L.
Pedersen, P.C., et al., "Microwave Reflection and Transmission Measurements for Pulmonary Diagnosis and Monitoring", IEEE Transactions on Biomedical Engineering, IEEE Service Center, Piscataway, NJ, US, vol. BME-19, No. 1, Jan. 1, 1978; pp. 40-48.
Polhemus, "Fastrak: The Fast and Easy Digital Tracker", USA, 2008.
Ringer et al., Follow-up of Stented Carotid Arteries by Doppler Ultrasound, Sep. 2002, Neurosurgery, vol. 51, No. 3, p. 639-643.

Supplementary European Search Report and European Search Opinion, dated Jun. 13, 2013, for European Application No. 09851811.1.
Supplementary European Search Report and European Search Opinion, dated Mar. 11, 2014, for European Application No. 11809359.1.
Supplementary European Search Report and Search Opinion, dated Dec. 4, 2014, for EP Application No. 10834292.4.
Supplementary European Search Report, mailed Mar. 7, 2016, for EP Application No. 13748671.8.
Written Opinion for International Application No. PCT/IB2010/054861 dated Apr. 5, 2011.
Yang, F. et al. "Enhancement of Printed Dipole Antennas Characteristics Using Semi-EBG Ground Plane", Journal of Electromagnetic Waves and Application, U.S., Taylor & Francis, Apr. 3, 2006, vol. 8, pp. 993-1006.
International Search Report and Written Opinion, mailed Jun. 24, 2015, for International Application No. PCT/IL2015/050140, filed Feb. 5, 2015.
Tao et al., "An Ultrawideband Radar Based Pulse Sensor for Arterial Stiffness Measurement", Proceedings of the 29th Annual International Conference of the IEEE EMBS, Aug. 23-26, 2007, pp. 1679-1682.

\* cited by examiner

410

*Radar pulse wave* amplitude t

412

Identify depth of an artery to be interrogated by RF signals

Isolate RF signals reflected from the identified depth

418

414

420 — RF pulse signal

RF pulse peak
detection algorithm

422 — Low-pass Filter
(~16 Hz cutoff)

RF filter algorithm

424 — High-pass Filter
(~8 Hz cutoff)

416

426 — $|d[\ ]/dt|$

428 — 80 ms Moving
Average

430 — Peak
Detection

432 — Detection
Rules

434 — Heart rate signal          FIG. 4B

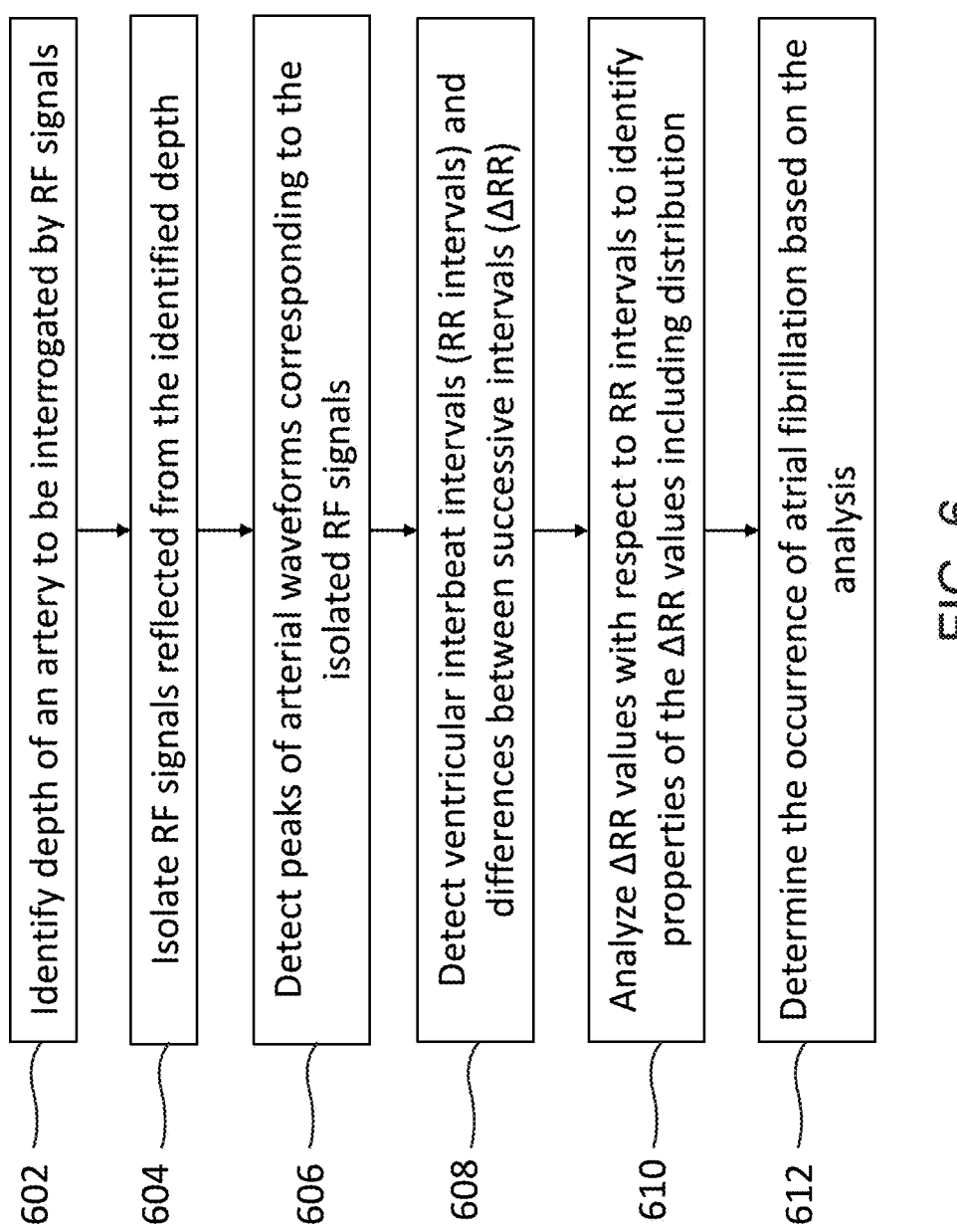

FIG. 6

602 — Identify depth of an artery to be interrogated by RF signals

604 — Isolate RF signals reflected from the identified depth

606 — Detect peaks of arterial waveforms corresponding to the isolated RF signals 608 — Detect ventricular interbeat intervals (RR intervals) and differences between successive intervals (ΔRR)

610 — Analyze ΔRR values with respect to RR intervals to identify properties of the ΔRR values including distribution 612 — Determine the occurrence of atrial fibrillation based on the analysis

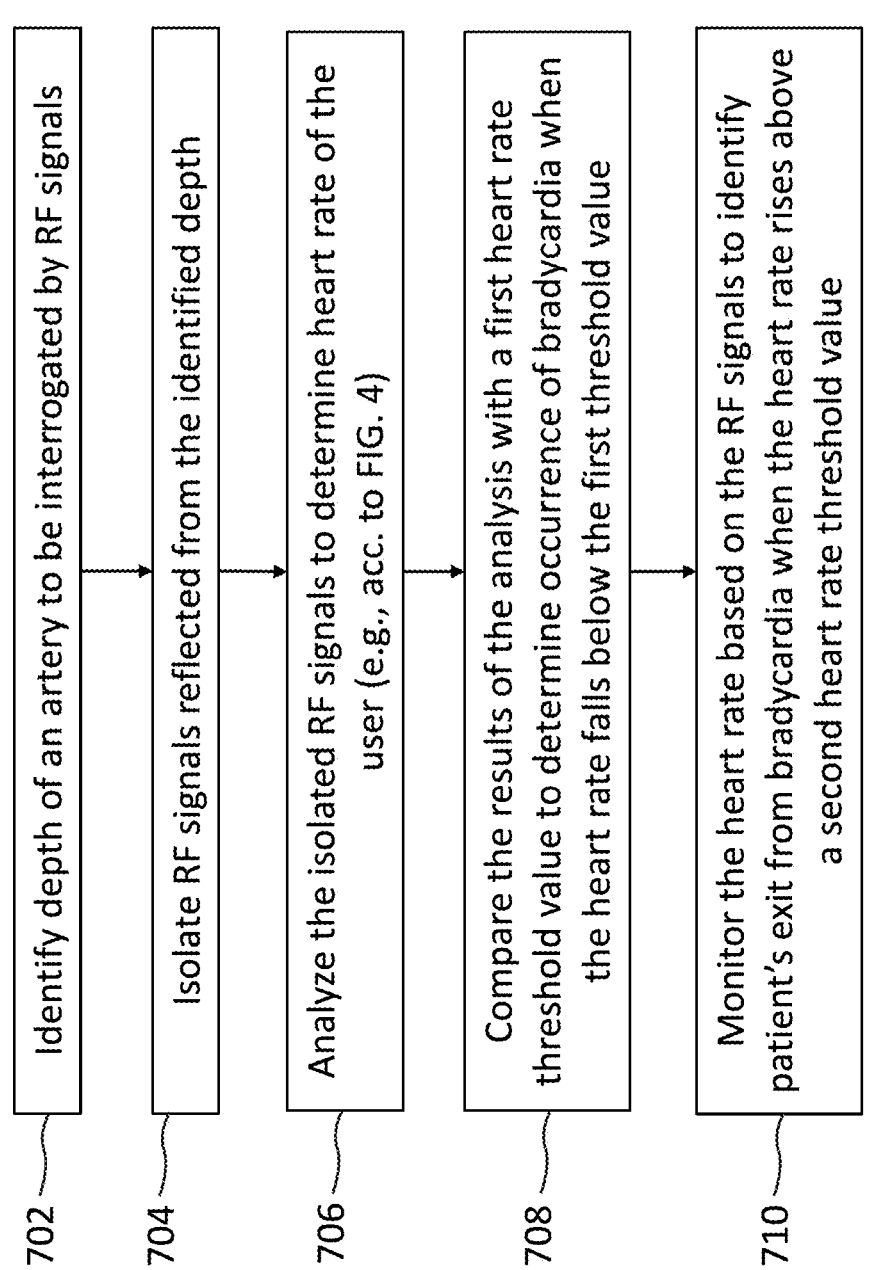

702 — Identify depth of an artery to be interrogated by RF signals

704 — Isolate RF signals reflected from the identified depth

706 — Analyze the isolated RF signals to determine heart rate of the user (e.g., acc. to FIG. 4)

708 — Compare the results of the analysis with a first heart rate threshold value to determine occurrence of bradycardia when the heart rate falls below the first threshold value 710 — Monitor the heart rate based on the RF signals to identify patient's exit from bradycardia when the heart rate rises above a second heart rate threshold value

FIG. 7

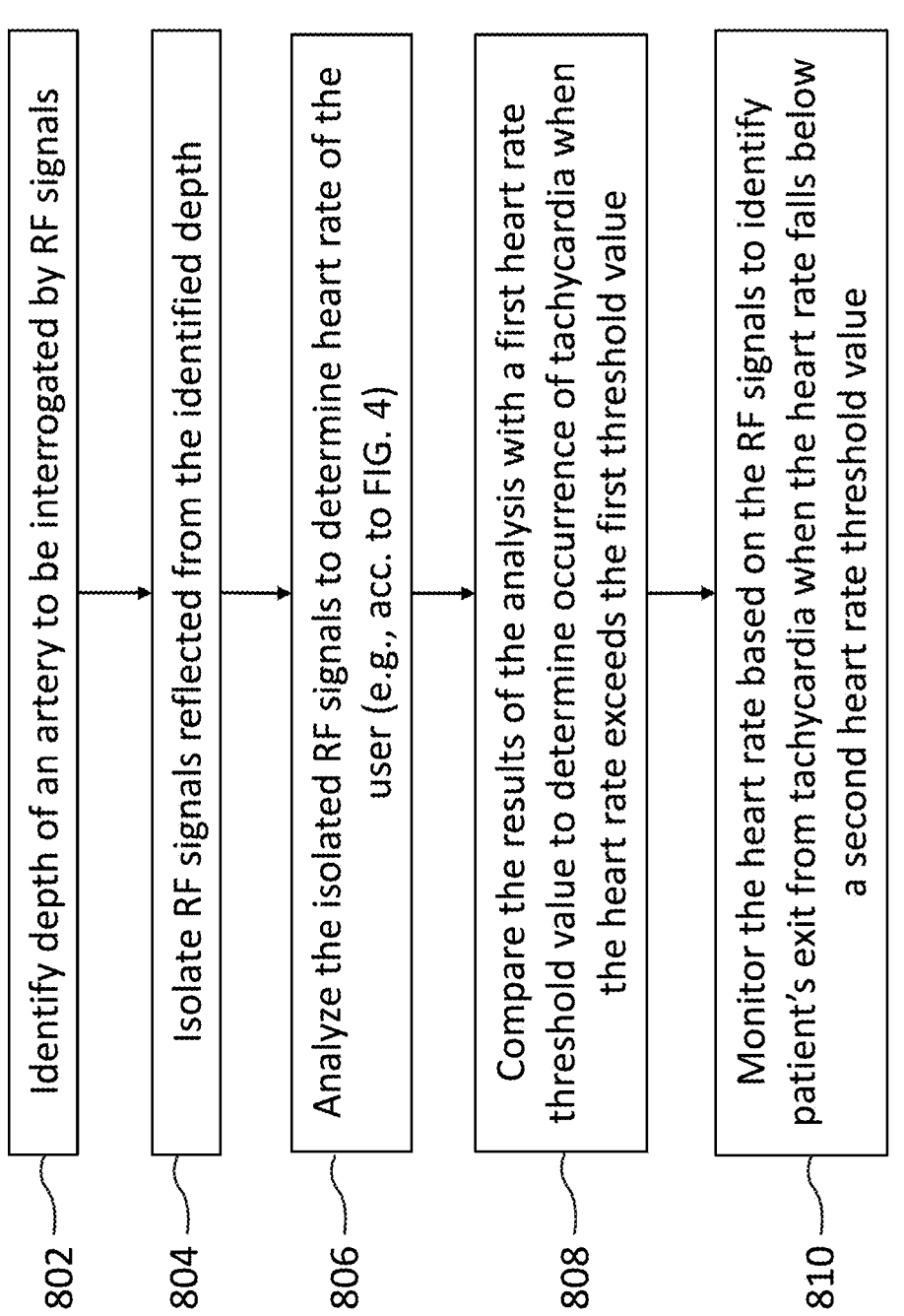

Identify depth of an artery to be interrogated by RF signals — 802

Isolate RF signals reflected from the identified depth — 804

Analyze the isolated RF signals to determine heart rate of the user (e.g., acc. to FIG. 4) — 806

Compare the results of the analysis with a first heart rate threshold value to determine occurrence of tachycardia when the heart rate exceeds the first threshold value — 808

Monitor the heart rate based on the RF signals to identify patient's exit from tachycardia when the heart rate falls below a second heart rate threshold value — 810

FIG. 8

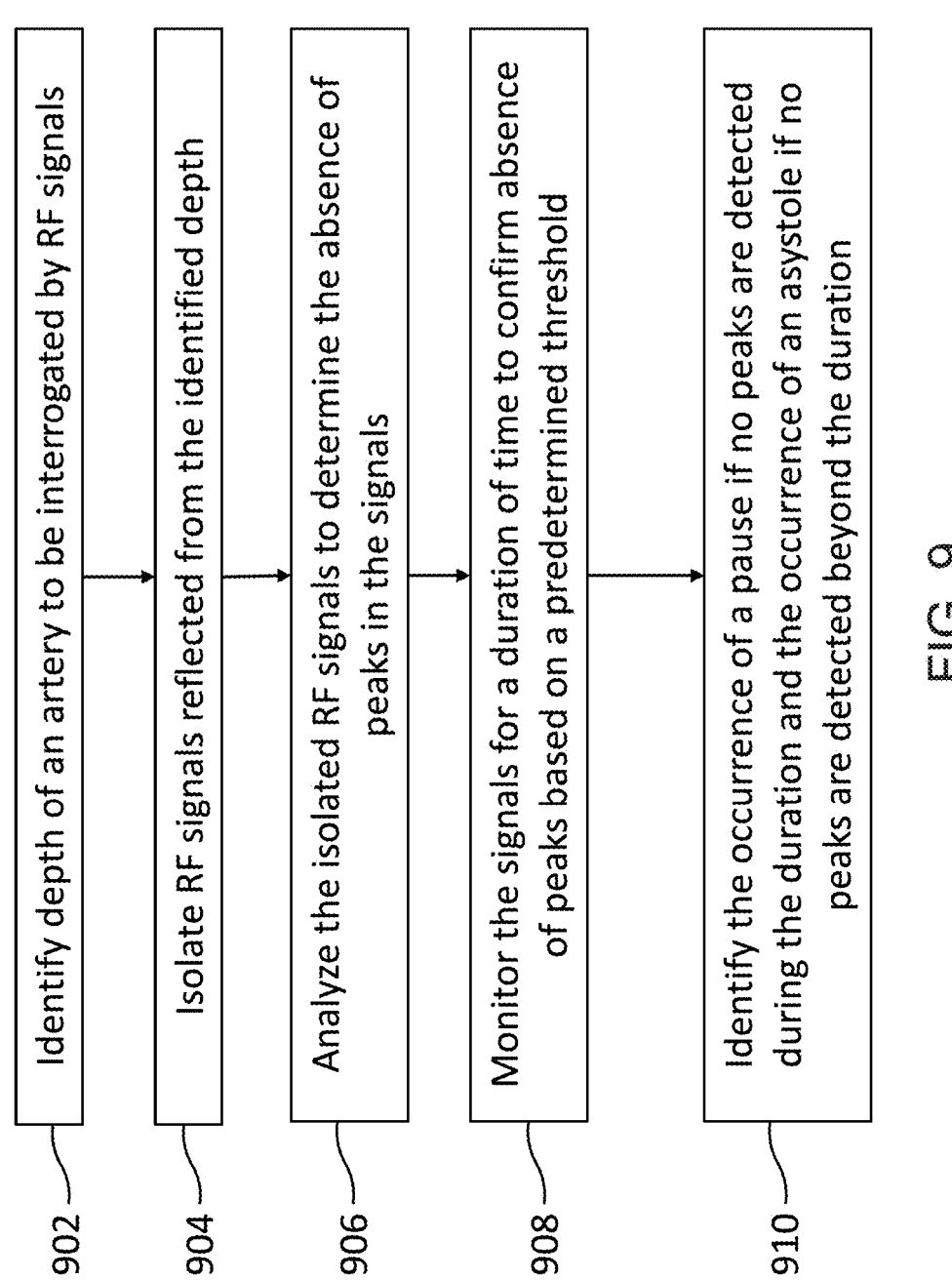

902 Identify depth of an artery to be interrogated by RF signals

904 Isolate RF signals reflected from the identified depth

906 Analyze the isolated RF signals to determine the absence of peaks in the signals 908 Monitor the signals for a duration of time to confirm absence of peaks based on a predetermined threshold 910 Identify the occurrence of a pause if no peaks are detected during the duration and the occurrence of an asystole if no peaks are detected beyond the duration

FIG. 9

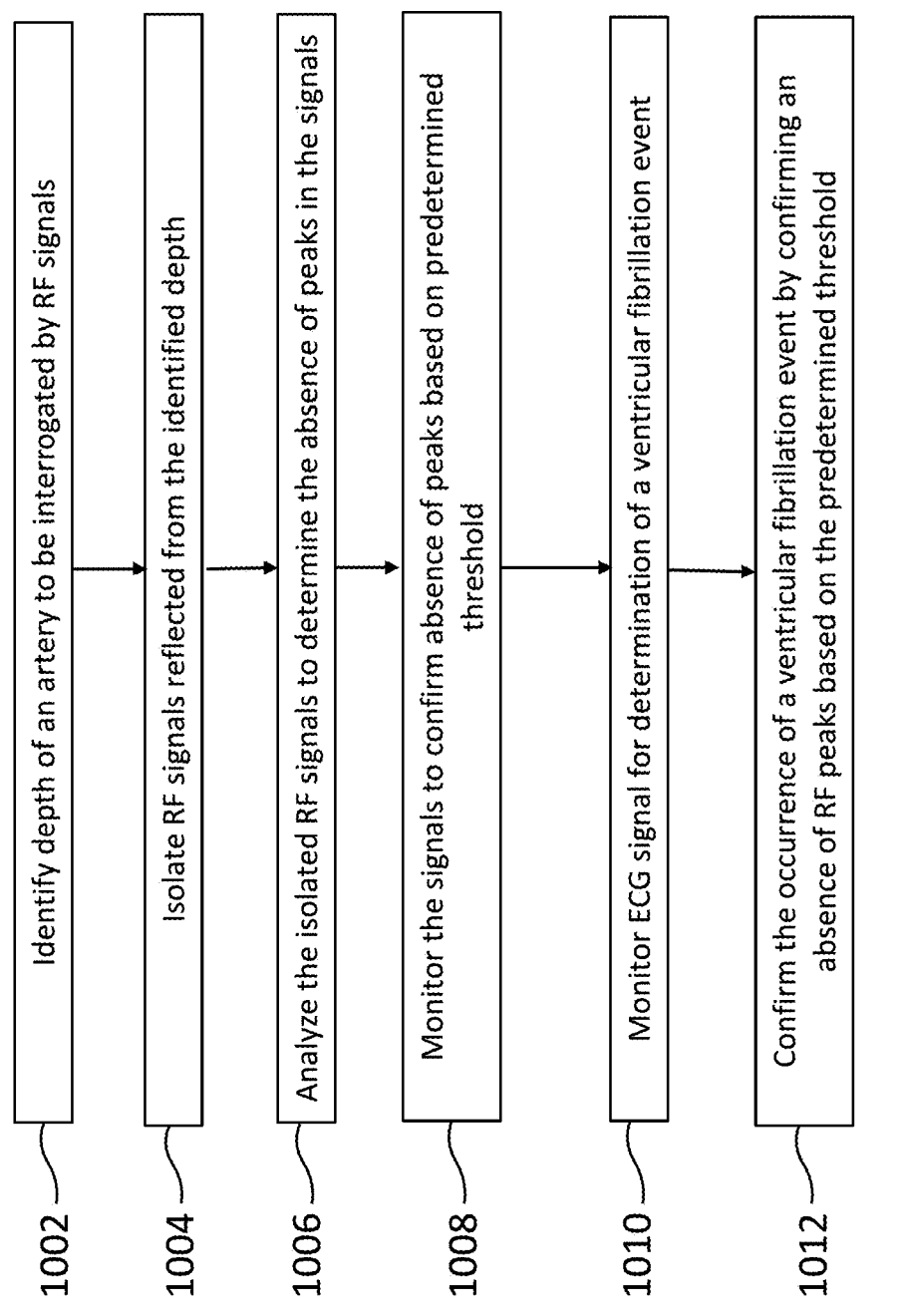

FIG. 10

1002 — Identify depth of an artery to be interrogated by RF signals

1004 — Isolate RF signals reflected from the identified depth

1006 — Analyze the isolated RF signals to determine the absence of peaks in the signals 1008 — Monitor the signals to confirm absence of peaks based on predetermined threshold 1010 — Monitor ECG signal for determination of a ventricular fibrillation event 1012 — Confirm the occurrence of a ventricular fibrillation event by confirming an absence of RF peaks based on the predetermined threshold 1202  Identify depth of an artery to be interrogated by RF signals 1204  Isolate RF signals reflected from the identified depth 1206  Analyze the isolated RF signals to identify presence of an extra heartbeat to determine occurrence of ventricular ectopy 1302  Identify an interrogation zone located between at least two RF detectors 1304  Determine entry time and exit time of an arterial pulse within the interrogation zone 1306  Analyze the entry and exit times to determine pulse wave velocity (PWV) and/or pulse transit time (PTT)

1308  Determine blood pressure of the patient based on the determined PWV and/or PVV

1

SYSTEMS, DEVICES AND METHODS FOR RADIO FREQUENCY-BASED PHYSIOLOGICAL MONITORING OF PATIENTS

CROSS-REFERENCE TO RELATED APPLICATIONS

The present application claims the benefit of priority to U.S. Provisional Application No. 62/650,706, filed on Mar. 30, 2018, the contents of which are hereby incorporated by reference in their entirety.

FIELD OF THE DISCLOSURE

Embodiments of the current disclosure are directed toward physiological monitoring of patients, and more particularly, systems, devices and methods for radio frequency (RF)-based physiological monitoring of patients to diagnosis arrhythmia, blood pressure, and other related medical conditions.

BACKGROUND OF THE DISCLOSURE

There is a wide variety of electronic and mechanical devices for monitoring underlying patients' medical conditions. In some examples, depending on the underlying medical condition being monitored and/or treated, medical devices such as cardiac pacemakers or defibrillators may be surgically implanted or connected externally to the patient. Physicians may use such devices alone or in combination with drug therapies to treat or control patient medical conditions.

Such patients can include heart failure patients, e.g., congestive heart failure (CHF) is a condition in which the heart's function as a pump is inadequate to meet the body's needs. Generally, many disease processes can impair the pumping efficiency of the heart to cause congestive heart failure. The symptoms of congestive heart failure vary, but can include: fatigue, diminished exercise capacity, shortness of breath, and swelling (edema). The diagnosis of congestive heart failure is based on knowledge of the individual's medical history, a careful physical examination, and selected laboratory tests.

Patients in this group can suffer from cardiac arrhythmias. One of the most deadly cardiac arrhythmias is ventricular fibrillation, which occurs when normal, regular electrical impulses are replaced by irregular and rapid impulses, causing the heart muscle to stop normal contractions. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia. External pacemakers, defibrillators and other medical monitors designed for ambulatory and/or long-term use have further improved the ability to timely detect and treat life-threatening conditions.

Heart failure patients can also benefit from having their thoracic fluid levels being monitored. Radio-frequency (RF) electromagnetic radiation has been used for diagnosis and imaging of body tissues. Diagnostic devices that include an antenna can be used to direct the RF electromagnetic waves into a body and generate signals responsively to the waves that are scattered from within the body. Such signals can be processed to determine various properties of body tissues located along the paths of the transmitted and/or scattered waves.

There is a wide variety of electronic and mechanical devices for monitoring underlying patients' medical conditions. In some examples, depending on the underlying medical condition being monitored and/or treated, medical devices such as radio-frequency (RF)-based devices can be used for diagnosis and imaging of body tissues. Diagnostic devices that include antenna can be used to direct the RF electromagnetic waves into a body and generate signals responsively to the waves that are scattered from within the body. Such signals can be processed to determine various properties of body tissues located along the paths of the transmitted and/or scattered waves, thereby facilitating the diagnosis of medical conditions.

SUMMARY OF SOME OF THE EMBODIMENTS

Embodiments of the current disclosure are directed toward physiological monitoring of patients, and more particularly, systems, devices and methods for radio frequency (RF)-based physiological monitoring of patients to diagnosis arrhythmia and blood pressure related medical conditions (among others).

In some embodiments, a physiological blood pressure monitoring device is presented, which comprises at least one antenna and associated first circuitry configured to transmit radio-frequency (RF) waves in a range from about 100 MHz to about 5 GHz towards an artery of a subject located within an interrogation zone of tissue and proximate the at least one antenna and receive reflected RF waves from the artery, and second circuitry comprising at least one controller and configured to control generation of the RF waves, process reflected RF waves into RF signals corresponding to the reflected RF waves, analyze the RF signals to determine a time varying radar cross-section of the artery over a duration, determine an associated pulse waveform from the time varying radar cross-section of the artery over the duration, and determine a blood pressure measure of the subject based on the associated pulse waveform at least once every 2 minutes over the duration.

Such embodiments, for example, may include at least one of the following (and in some embodiments, a plurality of the following, and in still further embodiments all of the following) features, structure, steps, functionality and/or clarifications, yielding yet further embodiments. One of skill in the art will also appreciate that one or more of these features, structure, steps, functionality and/or clarifications (and in some embodiments, a plurality of) can comprise an embodiment:

the second circuitry may be configured to determine the blood pressure measure of the subject at least once every 90 seconds, every 60 seconds, every 45 seconds, every 30 seconds, every 15 seconds, or every 5 seconds over the duration;

the second circuitry may be configured to determine the blood pressure measure of the subject within an interval set by a user-configurable parameter, where, the user-configurable parameter may be stored in a memory of the device;

the second circuitry may be configured to determine the blood pressure measure of the subject from a first pulse to a second pulse of the patient;

a period of time between the first and second pulse may be at least one of predetermined and user configurable;

the at least one antenna may be configured to direct radio-frequency waves in one or more ranges from about 100 MHz to about 1 GHz, about 200 MHz to about 2.5 GHz, about 200 MHz to about 3 GHz, and about 500 MHz to about 5 GHz;

the interrogation zone of tissue may comprise a volume of tissue;

the at least one antenna and associated first circuitry may comprise at least two RF transceivers (RFTs);

a first of the at least two RFTs may be arranged adjacent a proximal portion of the interrogation zone where the pulse waveform enters and a second of the at least two RFTs may be located at a distal portion of the interrogation zone where the pulse waveform leaves the interrogation zone;

the proximal and distal portions of the interrogation zone may be arranged along a longitudinal path corresponding to the artery's longitudinal path;

the second circuitry may be additionally configured to sample the reflected RF waves received by each of the first and second RFTs;

a pulse transit time (PTT) may be determined based on the sampled RF waves;

the blood pressure measure may be determined from the PTT;

the at least two transceivers may be first and second RF transceivers, which may be synchronized;

the at least one antenna and at least one of the RFTs may comprise a monopulse RF transceiver configured to implement at least one of a delta and sigma signal, where:

the second circuitry may additionally be configured to determine a slope of the delta/sigma signal so as to estimate a velocity of the pulse wave; and the delta and sigma channels may be generated via the second circuitry and/or via software implemented on a microprocessor;

the at least one antenna may comprise at least two cyclic antenna arrays, where the second circuitry may then be configured to sample each array and select the best RF waves from one of the arrays;

an attachment mechanism for removably attaching the at least one antenna, the RFTs or arrays proximate the skin of the user, where the attachment mechanism may be selected from the group consisting of: a vest, a garment, a wrist strap, a bracelet, a patch, a sock, a shoe, a boot, and a chest strap;

upon the attachment mechanism comprising a wrist strap. the device is configured as a watch-like device for removable attachment to a wrist of the user;

at least two ECG electrodes;

where the second circuitry may be additionally configured to receive signals from the ECG electrode and at least one of process and analyze the received signals to determine arterial pulse peaks;

the second circuitry may be additionally configured to spatially resolve the interrogation zone or specific tissue therein;

the RFTs, if provided, may be spaced apart a predetermined distance comprising at least one of: between 1 cm and 30 cm, 30 cm and 50 cm, 50 cm and 90 cm, and 90 cm and 200 cm;

the first circuitry may be configured to control the at least one antenna to emit frequencies in one or more ranges from about 100 MHz to about 1 GHz, about 200 MHz to about 2.5 GHz, about 200 MHz to about 3 GHz, and about 500 MHz to about 5 GHz; and the area of at least one antenna is between 0.5 cm$^2$ and 15 cm$^2$;

In some embodiments, a physiological blood pressure monitoring system is provided, and comprises a radar cross-section monitoring device comprising an attachment structure configured to removably and mechanically attach the radar cross-section monitoring device to the subject, at least one antenna disposed within the attachment structure and configured to direct radio-frequency (RF) waves in a range from 500 MHz to 5 GHz towards an artery of the subject located within an interrogation zone of tissue and proximate the at least one antenna and receive the reflected RF waves from the artery, and device circuitry comprising at least one controller electrically coupled to the at least one antenna. The device circuitry is configured to control generation and transmission of the RF waves, and process reflected RF waves into RF signals corresponding to the reflected RF waves. The system further includes communications circuitry configured for wired or wireless transmission of the RF signals to an external entity, and a remote processing server. The remote processing server comprising server circuitry configured to:

receive the RF signals from the radar cross-section monitoring device, analyze the RF signals to determine a time varying radar cross-section of the artery over a period of time, determine an associated pulse waveform from the time varying radar cross-section of the artery over the period of time, and determine a time-varying blood pressure measure of the subject based on associated pulse waveform.

Such embodiments, for example, may include at least one of the following (and in some embodiments, a plurality of the following, and in still further embodiments all of the following) features, structure, steps, functionality and/or clarifications, yielding yet further embodiments. One of skill in the art will also appreciate that one or more of these features, structure, steps, functionality and/or clarifications (and in some embodiments, a plurality of) can comprise an embodiment:

the server circuitry may be configured to determine the blood pressure measure of the subject at least once every 90 seconds, every 60 seconds, every 45 seconds, every 30 seconds, every 15 seconds, or every 5 seconds over the duration;

the server circuitry may be configured to determine the blood pressure measure of the subject within an interval set by a user-configurable parameter, where the user-configurable parameter may be stored in a memory of the radar cross-section monitoring device;

the server circuitry may be configured to determine the blood pressure measure of the subject from a first pulse to a second pulse of the patient, where a period of time between the first and second pulse is at least one of predetermined and user configurable;

the at least one antenna may be configured to direct radio-frequency waves in one or more ranges from about 100 MHz to about 1 GHz, about 200 MHz to about 2.5 GHz, about 200 MHz to about 3 GHz, and about 500 MHz to about 5 GHz;

the interrogation zone of tissue comprises a volume of tissue;

the at least one antenna may comprise at least two RF transceivers (RFTs), where a first of the at least two RFTs may arranged adjacent a proximal portion of the interrogation zone where the pulse waveform enters and a second of the at least two RFTs may be located at a distal portion of the interrogation zone where the pulse waveform leaves the interrogation zone;

the proximal and distal portions of the interrogation zone may be arranged along a longitudinal path corresponding to the artery's longitudinal path;

the server circuitry may additionally be configured to sample the reflected RF waves received by each of the first and second RFTs;

the at least one antenna and at least one of the RFTs may comprise a monopulse RF transceiver configured to implement at least one of a delta and sigma signal;

where the circuitry may be additionally configured to determine a slope of the delta/sigma signal so as to estimate a velocity of the pulse wave;

and/or where the delta and sigma channels may be generated via the circuitry and/or via software implemented on a microprocessor;

a pulse transit time (PTT) may be determined based on the sampled RF waves, and the blood pressure measure may be determined from the PTT;

the at least two RF transceivers comprise first and second RF transceivers which may be synchronized;

the at least one antenna may comprise at least two cyclic antenna arrays, where the circuitry may be configured to sample each array and select the best RF waves from one of the arrays;

an attachment mechanism for removably attaching the at least one antenna, RFTs or arrays proximate the skin of the user, where the attachment mechanism may be selected from the group consisting of: a vest, a garment, a wrist strap, a bracelet, a patch, a sock, a shoe, a boot, and a chest strap;

the attachment structure may comprise a wrist strap and where the radar cross-section monitoring device is configured as a watch-like device for removable attachment to a wrist of the user;

at least two ECG electrodes, and if included, the server circuitry may be additionally configured to receive signals from the ECG electrode and at least one of process and analyze the received signals to determine arterial pulse peaks;

the server circuitry may be additionally configured to spatially resolve the interrogation zone or specific tissue therein;

the RFTs, if included, may be spaced apart a predetermined distance comprising at least one of: between 1 cm and 30 cm, 30 cm and 50 cm, 50 cm and 90 cm, and 90 cm and 200 cm;

the device circuitry may be configured to control the at least one antenna to emit frequencies in one or more ranges from about 100 MHz to about 1 GHz, about 200 MHz to about 2.5 GHz, about 200 MHz to about 3 GHz, and about 500 MHz to about 5 GHz; and the area of at least one antenna is between 0.5 cm$^2$ and 15 cm$^2$.

In some embodiments, a physiological monitoring device is presented and comprises at least one antenna and associated circuitry configured to direct radio-frequency (RF) waves in a range from about 100 MHz to about 5 GHz towards an artery located within a tissue of a subject and receive reflected RF waves from the artery, and circuitry comprising at least one controller and configured to (at least one of, and in some embodiments, a plurality of, in some embodiments, all of):

control generation and transmission of the RF waves, process reflected RF waves into RF signals corresponding to the reflected RF waves, analyze the RF signals to determine a time varying radar cross-section (RCS) of the artery over a duration of time, determine at established intervals within the duration of time based on the RCS at least one physiological condition including at least one of: a heart-rate, ventricular ectopic beats (VEB), ventricular runs, ventricular tachycardia, ventricular fibrillation, atrial fibrillation, bradycardia, and tachycardia, and output at least one of an alert and a signal corresponding to the determined and/or updated at least one physiological condition.

Such embodiments, for example, may include at least one of the following (and in some embodiments, a plurality of the following, and in still further embodiments all of the following) features, structure, steps, functionality and/or clarifications, yielding yet further embodiments. One of skill in the art will also appreciate that one or more of these features, structure, steps, functionality and/or clarifications (and in some embodiments, a plurality of) can comprise an embodiment:

a housing configured for removable attachment to or proximate the skin of the user, where the at least one antenna is arranged on the housing;

the at least one controller may be configured to analyze the RF signals by identifying reflected RF waves from a predetermined depth beneath the skin selected so as to correspond to an artery within the tissue of the subject;

the at least one controller may be further configured to identify the reflected RF waves from the predetermined depth beneath the skin by selecting the reflected RF waves having highest pulsating amplitudes of the corresponding RF signals;

the at least one controller may be configured to analyze the RF signals by analyzing each RF signal to detect arterial waveform peaks of the artery, where the detected waveform peaks corresponds to beats of the user heart;

the at least one controller may be configured to determine a plurality of RR intervals based on the detected peaks of the arterial waveform;

the at least one controller may be configured to analyze sequences of RR intervals and heartrate variability (ΔRR) values based on the plurality of RR intervals of the arterial waveform so as to determine atrial fibrillation in the subject;

an attachment mechanism for removably attaching the device to or proximate the skin of the user, where the attachment mechanism may be selected from the group consisting of: a vest, a garment, a wrist strap, a bracelet, a patch, and a chest strap, upon the attachment mechanism comprising a wrist strap, the device may then configured as a watch-like device for removable attachment to a wrist of the user;

the circuitry may be further configured to transmit at least one of the RF signals and the determined at least one physiological condition to a remote device, where the remote device may comprise at least one of a gateway device and a remote server, and the gateway device may be configured to relay data from the monitoring device to the remote server, moreover, the gateway device may include a gateway display, which may be a touch sensitive screen;

the circuitry may comprise a plurality of specific circuits, one and/or another of specifically structured to perform any one or more of the steps of any of the above-noted embodiments;

the circuitry may comprise one or more computer processors configured with computer instructions operating therein to perform any one or more of the steps of any of the above-noted embodiments;

a user interface for receiving input from the subject, where such user input may comprise one or more of a symptom experienced or being experienced by the subject, instruction to initiate recording of the least one physiological condition to device memory, transmission of data between the device and a remote device, and a response to a prompt initiated by the device;

the circuitry may further comprise a radio transmitter and/or receiver;

one or more sensors may be selected from the group consisting of a temperature sensor, conductance sensor, pressure sensor, an electrode(s), an accelerometer, a GPS sensor, and a light sensor;

a power source;

the one or more sensors may be configured to be affixed to or integral with the device;

a display configured to at least present information on at least one of operation, condition, and function of at least one of the circuitry and device, where:

the display may comprise a touch screen configured to receive user input; and the display may comprise an LED indicator; and the at least one antenna may comprise an adhesive antenna, a flexible antenna, a bistatic antenna, a narrowband antenna, or a wideband antenna In some embodiments, a physiological monitoring system is presented which comprises a physiological monitoring device comprising at least one antenna and associated circuitry configured to direct radio-frequency (RF) waves in a range from about 100 MHz to about 5 GHz towards an artery located within a tissue of a subject and receive reflected RF waves from the artery, and device circuitry comprising at least one controller and electrically coupled to the at least one antenna and configured to at least one of (in some embodiments, a plurality of, and in some embodiments, all of):

control generation and transmission of the RF waves, process reflected RF waves into RF signals corresponding to the reflected RF waves, and communications circuitry configured for wired or wireless transmission of the RF signals to an external entity;

The system may also include a remote processing server comprising server circuitry configured to at least one of (in some embodiments, a plurality of, in some embodiments, all of):

analyze the RF signals to determine a time varying radar cross-section (RCS) of the artery over a duration of time, determine at established intervals within the duration of time based on the RCS at least one physiological condition including at least one of: a heart-rate, ventricular ectopic beats (VEB), ventricular runs, ventricular tachycardia, ventricular fibrillation, atrial fibrillation, bradycardia, and tachycardia; and output at least one of an alert and a signal corresponding to the determined and/or updated at least one physiological condition.

Such embodiments, for example, may include at least one of the following (and in some embodiments, a plurality of the following, and in still further embodiments all of the following) features, structure, steps, functionality and/or clarifications, yielding yet further embodiments. One of skill in the art will also appreciate that one or more of these features, structure, steps, functionality and/or clarifications (and in some embodiments, a plurality of) can comprise an embodiment:

a housing configured for removable attachment to or proximate the skin of the user, wherein the at least one antenna is arranged on the housing;

the at least one controller may be configured to analyze the RF signals by identifying reflected RF waves from a predetermined depth beneath the skin selected so as to correspond to an artery within the tissue of the subject;

the at least one controller may be further configured to identify the reflected RF waves from the predetermined depth beneath the skin by selecting the reflected RF waves having highest pulsating amplitudes of the corresponding RF signals;

the at least one controller is configured to analyze the RF signals by analyzing each RF signal to detect arterial waveform peaks of the artery, wherein the detected waveform peaks corresponds to beats of the user heart.

the at least one controller may be configured to determine a plurality of RR intervals based on the detected peaks, and the at least one controller may be configured to analyze sequences of RR intervals and heartrate variability ($\Delta$RR) values based on the plurality of RR intervals to determine atrial fibrillation in the subject, an attachment mechanism for removably attaching the device to or proximate the skin of the user, where the attachment mechanism is selected from the group consisting of: a vest, a garment, a wrist strap, a bracelet, a patch, and a chest strap, where upon the attachment mechanism comprising a wrist strap, the device is configured as a watch-like device for removable attachment to a wrist of the user;

the communications circuitry is further configured to transmit at least one of the RF signals and the determined at least one physiological condition to a remote device, where the remote device may comprise at least one of a gateway device and a remote server, and the gateway device may be configured to relay data from the monitoring device to the remote server;

the gateway device may include a gateway display; and the gateway display may be a touch sensitive screen;

the server circuitry may comprise a plurality of specific circuits, one and/or another of specifically structured to perform any one or more of the steps in the above-noted embodiments;

the server circuitry may comprise one or more computer processors configured with computer instructions operating therein to perform any one or more of the steps of the above-noted embodiments;

a user interface for receiving input from the subject, where such user input may comprise one or more of a symptom experienced or being experienced by the subject, instructions to initiate recording of the least one physiological condition to device memory, transmission of data between the device and a remote device, and/or a response to a prompt initiated by the device;

the communications circuitry may further comprise a radio transmitter and/or receiver;

one or more sensors which may be selected from the group consisting of a temperature sensor, conductance sensor, pressure sensor, an electrode(s), an accelerometer, a GPS sensor, and a light sensor;

the one or more sensors may be configured to be affixed to or integral with the device;

a power source;

a display which may be configured to at least present information on at least one of operation, condition, and function of at least one of the server circuitry and device, where the display may comprise a touch screen configured to receive user input, and the display may comprise an LED indicator; and the at least one antenna may comprise an adhesive antenna, a flexible antenna, a bistatic antenna, a narrowband antenna, or a wideband antenna.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are provided for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 4A-B respectively show example RF signal and example flowchart illustrating the process of detecting heart rate of a patient using the RF-based monitoring device disclosed herein, according to some embodiments.

FIG. 6 shows example flowchart illustrating the process of detecting atrial fibrillation using the RF-based monitoring device disclosed herein, according to some embodiments.

FIG. 7 shows example flowchart illustrating the process of detecting bradycardia using the RF-based monitoring device disclosed herein, according to some embodiments.

FIG. 8 shows example flowchart illustrating the process of detecting tachycardia using the RF-based monitoring device disclosed herein, according to some embodiments.

FIG. 9 shows example flowchart illustrating the process of detecting pauses and asystole using the RF-based monitoring device disclosed herein, according to some embodiments.

FIG. 10 shows example flowchart illustrating the process of detecting ventricular fibrillation using the RF-based monitoring device disclosed herein, according to some embodiments.

DETAILED DESCRIPTION OF SOME OF THE EMBODIMENTS

Figure 1A:
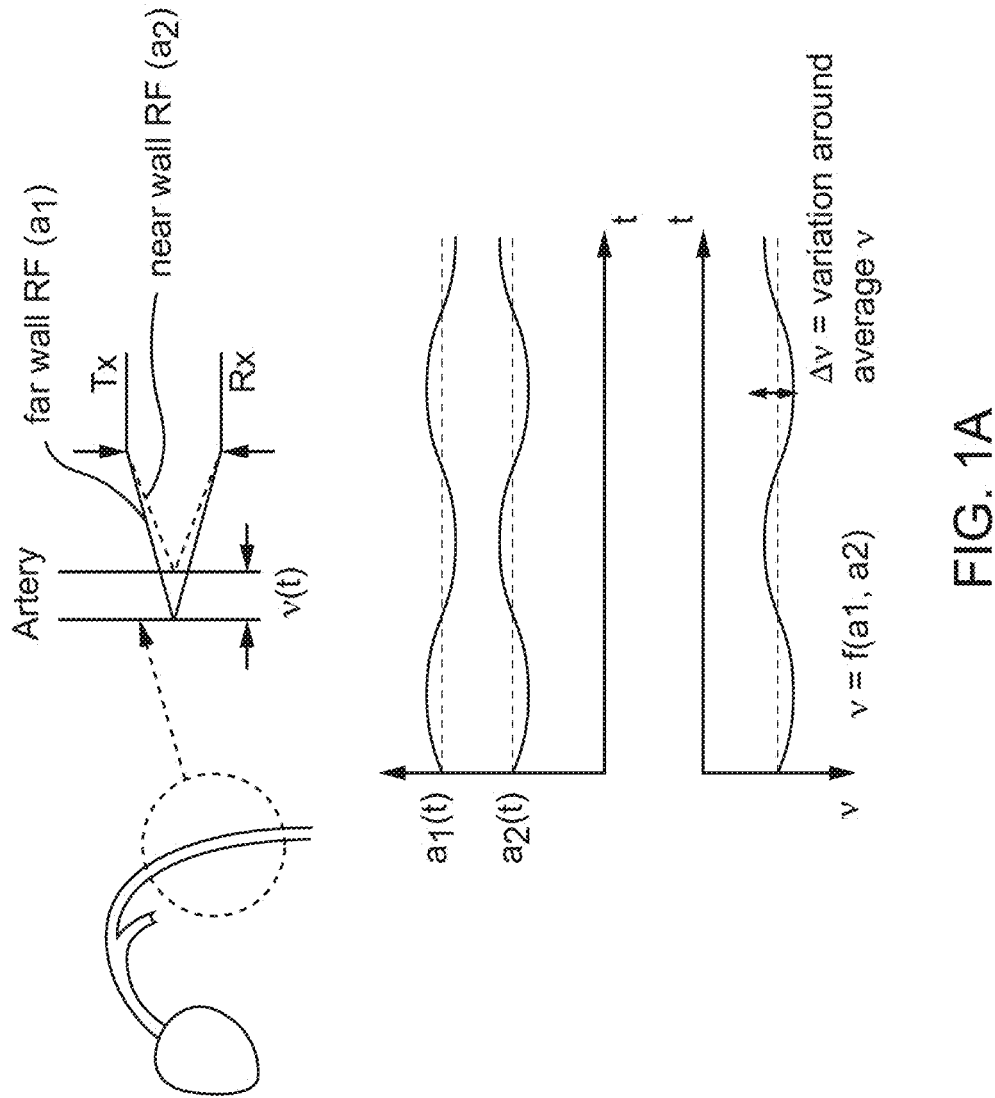
FIG. 1A shows an example illustration of using RF radar techniques for monitoring a patient's artery, according to some embodiments.

This disclosure relates to physiological monitoring systems, devices and methods implemented as, for example, wearable and/or wireless sensor(s) that can be used to aid clinicians in the diagnosis and identification of various medical conditions, events and/or trends. In implementations described herein, a physiological monitoring device is equipped with an RF radar transmitter and detector. The RF device transmits radio-frequency (RF) waves towards tissue of a patient, e.g., in some embodiments, a predetermined artery located within the tissue, and receives reflected RF waves from the artery. The arteries are blood lumen or vessels that deliver oxygen-rich blood from a subject's heart to the tissues of the subject's body.

The device, according to some embodiments, includes a transmitting antenna and a receiving antenna (which, in some embodiments could be a single antenna used for both transmission and reception), along with associated circuitry, configured to direct RF waves into the patient in a range from about, according to various embodiments: 100 MHz to about 5 GHz, from about 100 MHz to about 1 GHz, from about 200 MHz to about 2.5 GHz, from about 200 MHz to about 3 GHz, and from about 500 MHz to about 5 GHz, including values and subranges therebetween. In some embodiments, the antennas may be configured to have an area in the range from about 0.5 cm² to about 15 cm², from about 1 cm² to about 10 cm², from about 1.5 cm² to about 5 cm², about 2.5 cm², including values and subranges therebetween.

The RF radar techniques include generating and/or controlling RF waves and corresponding reflections from tissue, and in particular, moving arteries within the antennas' "field of view" or range. A time delay from RF wave emission to reflection is due to a physical distance from the antennas, while a strength of the RF reflection (or echo) is due to the artery's shape, size and dielectric constant relative to the surrounding tissue. The RF radar techniques, according to some embodiments, use the RF waves and reflections that occur along differences in the electromagnetic properties of the tissue such as permittivity and permeability. Larger transitions in underlying electromagnetic properties of tissues of interest (such as the patient's arteries or other natural lumen in the body of the patient) relative to surrounding tissue create larges contrast between tissue properties and stronger reflections. For example, the electromagnetic property difference between bone and muscle is larger than between lungs and muscle, and the reflections from the bone are expected to be greater than for the muscle for equal reflector size and shape. The RF device, according to some embodiments, can be configured such that electromagnetic property differences between a patient's artery and surrounding tissue can be used to study changes in the artery.

The device, according to some embodiments, includes a controller configured to process and analyze the reflected RF waves to determine one or more arterial pulses, which can then be used to determine a velocity of an arterial pulse waveform. An arterial pulse is a rhythmic contraction and expansion of the artery at each beat of the subject's heart. The RF-based physiological monitoring device, according to some embodiments, can discern such pulses from a position external to the patient and proximate to the artery. For example, the device may be located over a radial artery on a wrist forearm, upper arm, shoulder, and/or upper chest region of the patient. In some embodiments, the device may be attached to a part of the patient's using an attachment mechanism for removably attaching the device proximate the skin of the user, examples of the attachment mechanism can include one or more of a vest, a garment, a wrist strap, a bracelet, a patch, a sock, a shoe, a boot, and a chest strap. In some embodiments, the RF techniques include any one or more of the following (for example): monitoring the movements of different walls of the patient's artery in determining the arterial pulses, and monitoring a changing parameter of the artery that can be used to determine the arterial pulses. For example, a changing (e.g., time-varying) parameter can be a time-varying radar cross-section (RCS) of the artery over a duration of time. In some embodiments, an RF-based pulse pressure of the arterial pulse waveform can be determined based on one or more amplitudes of the RF pulse. For example, the pulse pressure can be a value representing the average, median, or mode peak amplitude value of one or more successive peaks in the RF waveform for a predetermined duration, e.g., 1 second, 2 seconds, 3 seconds, 5 seconds, or more.

An artery monitored by the device (according to some embodiments) may be e.g. anterior tibial, popliteal, brachial, carotid, or radial. Selecting an artery can be accomplished, in some embodiments, by tuning the device's depth perception (as described in further detail below). The aorta is the root systemic artery, and other arteries of the body include the arteries of the head and neck (e.g., the common carotid artery, an external carotid artery), the arteries of the upper extremity (arm) (e.g., the subclavian artery, the axillary artery, brachial artery, radial artery, ulnar artery), the arteries of the trunk (e.g., the descending aorta, that is, the thoracic aorta and abdominal aorta), the common iliac arteries (e.g., the hypogastric artery and the external iliac artery), and arteries of the lower extremity (leg) (e.g., the femoral artery, the popliteal fossa, the popliteal artery, the anterior tibial artery, the arteria *dorsalis* pedis, and the posterior tibial artery). One or more arteries of the human physiology may be selected for monitoring.

As noted above, RF radar can be used to monitor for changes in the RF reflections due to shifting artery boundaries relative to the surrounding tissue. FIG. 1A is an example scheme, according to some embodiments, for using RF radar techniques for monitoring a patient's artery. As shown, the RF transmitter Tx and receiver Rx can monitor an artery's two walls—a far wall and a near wall. The movement of the far wall of the artery over time relative to the surrounding tissue can be represented by the variable a1(t), The movement of the near wall of the artery over time relative to the surrounding tissue can be represented by the variable a2(t). As shown in the graphs, the two variables (a1, a2) are correlated to the artery wall ranges and indicate a time-varying change in the radius of the artery, r=f(x1, x2). Ar represents a variation around an average or mean value of r. In some implementations, r can be directly related to a patient's blood pressure. In some implementations, Ar can be related to changes in the patient's blood pressure. In other implementations, the rat two locations, e.g., t1, and t2 may be captured, and a delay, d between the can be used to estimate the arterial pulse propagation velocity, v=L/d, where L may be a distance travelled by the pulse. This speed, in turn can be related to mean blood pressure as described in detail below.

Figure 5A:
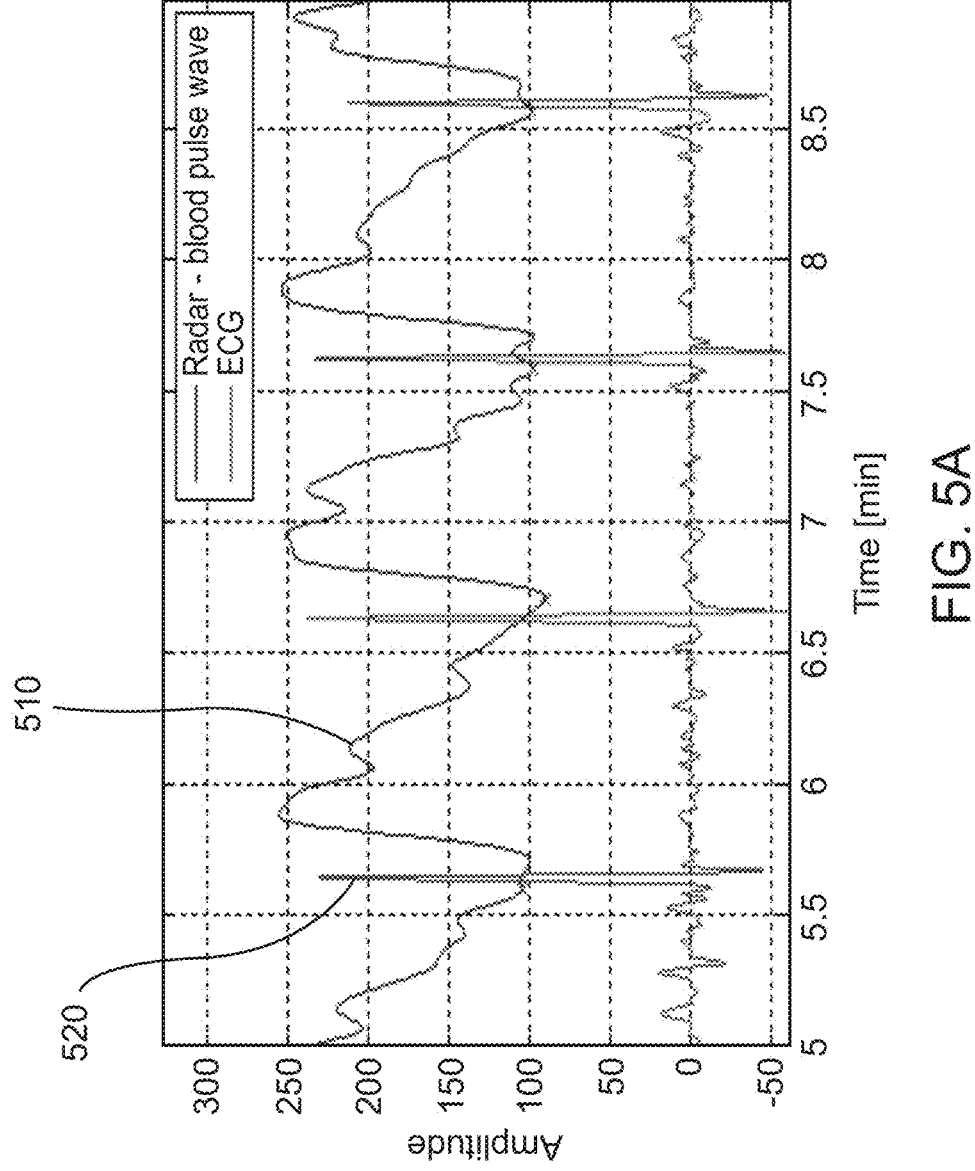
FIGS. 5A-B show example relationships between arterial pulse waveform peaks and R peaks of electrocardiogram (ECG) measurements, according to some embodiments.
Figure 5B:
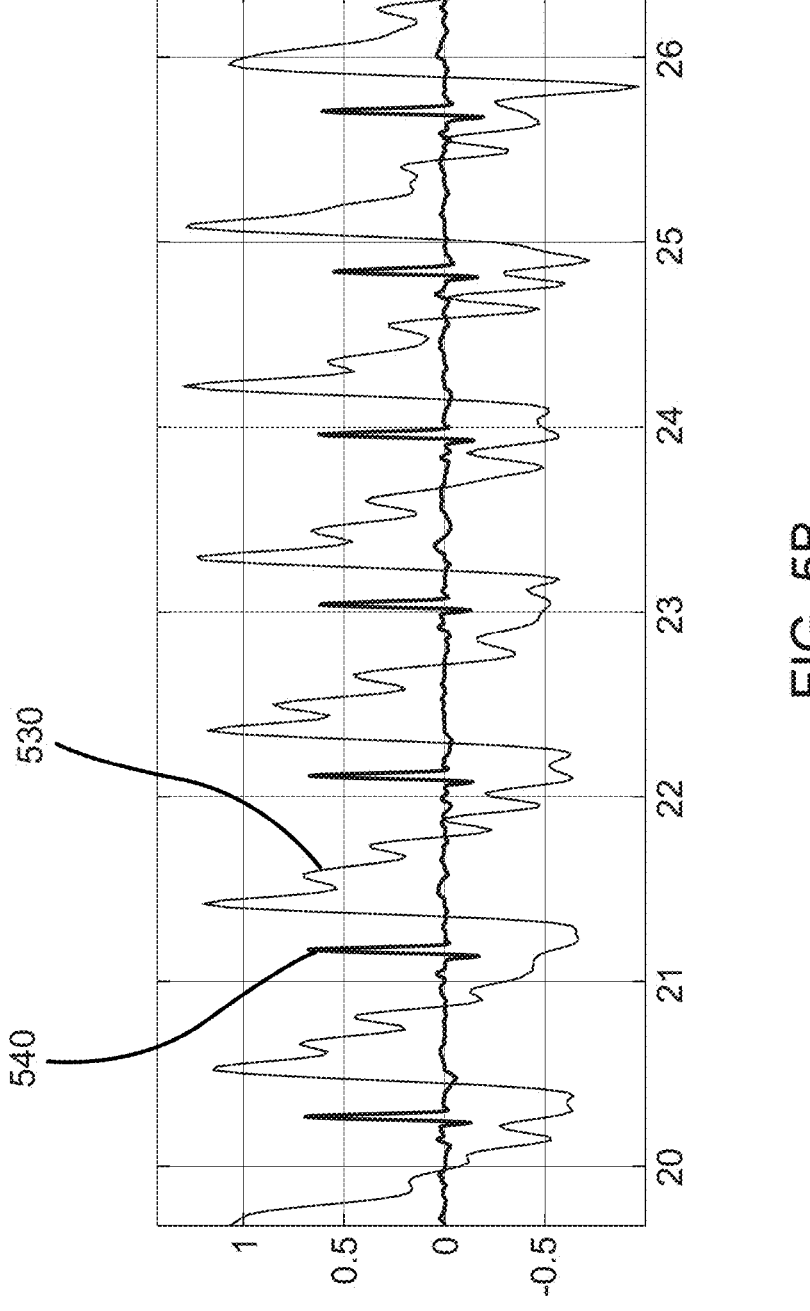

In some embodiments, the RF sensor can be used to obtain the arterial pulse waveform, which may provide clinical information such as, but not limited to, arterial stiffness and cardiac output. As the pulse wave is propagating through the artery, the RF sensor may measure the changing radar cross section of the artery. In such instances, the changing arterial cross section is related to the pulse wave, and accordingly, the arterial pulse waveform may be determined from the changing cross section. An example arterial pulse wave obtained using this method is depicted in FIGS. 5A-B, illustrating the radar pulse wave 510, 530, and the ECG wave 520, 540. Further, rather than use a direct measure of r, in implementations, a radar cross-section (RCS) of the artery can be determined as detailed below and used as a representation of r.

The techniques, methods, devices, and systems herein, according to various embodiments, have a number of advantages over conventional techniques, methods, devices, and systems of monitoring arterial pulses. For one, obtaining the arterial pulse waveform with embodiments of the present disclosure is non-invasive, while allowing penetration into the body, and can be operated with little or no expertise. In some embodiments, RCS information can be used to monitor cardiac related physiological information, including physiological information for underlying arrhythmia conditions. For example, such physiological information can include heart-rate information, and one or more cardiac arrhythmias, ventricular ectopy, ventricular ectopic beats (VEB), ventricular runs, ventricular tachycardia, atrial fibrillation, ventricular fibrillation, bradyarrhythmias, tachyarrhythmias, as well as, in some embodiments, one or more heart conduction disorders. For example, the device, according to some embodiments, can use RF based methods as described herein to confirm or verify ECG-based cardiac indications of heart-rate information, and one or more cardiac arrhythmias, ventricular ectopy, ventricular ectopic beats (VEB), ventricular runs, ventricular tachycardia, atrial fibrillation, ventricular fibrillation, bradyarrhythmias, tachyarrhythmias, and/or one or more heart conduction disorders.

In some embodiments, where a monopulse RF transceiver is used as an antenna, the velocity of the pulse wave can be determined/estimated by comparing the delta and sigma signals of the monopulse transceiver. For example, the velocity may be determined based on the slope of the delta/sigma signal. In some embodiments, the delta and sigma channels of the monopulse RF transceiver can be generated via a circuitry of the blood pressure monitoring device and/or software implemented on the controller.

In another example, a physiological blood pressure monitoring device according to some embodiments, is configured to analyze the RF signals to determine a time varying radar cross-section of the artery over a duration. The device can then determine an associated pulse waveform from the time varying radar cross-section of the artery over the duration, and determine, in some embodiments, a blood pressure measure of the subject. For example, the blood pressure measure may be made at least once every 60 seconds over the duration. As described below, the measurement period may be shorter or longer based on user-defined criteria. For instance, the interval can be a predetermined and user-configurable parameter, which may be stored in the memory of the blood pressure monitoring device. As an example, the blood pressure measure can be determined at least once every 500 milliseconds. For example, the blood pressure measure can be determined any of: at least once every 1 second, at least once every 2 seconds, at least once every 10 seconds, at least once every 30 seconds, at least once every 1 minutes, at least once every 2 minutes, at least once every 5 minutes, at least once every 10 minutes, and at least once every 30 minutes.

Also, in some embodiments, the blood pressure measure may be determined on a pulse to pulse, i.e., beat to beat basis. For example, a blood pressure measure may be determined from a first blood pressure measure taken at a first pulse to a second, different measure taken at a second, subsequent pulse of the patient. A duration between the first pulse and the second, subsequent pulse can be predetermined as an established value (e.g., 1 pulse, 2 pulses, 3 pulses, 5 pulses, 10 pulses, or more). In some cases, the number of pulses between measurements may be up to 25 pulses. In some cases, the number of pulses between measurements may be up to 50 pulses, 100 pulses, 200 pulses, 500 pulses, or 1000 pulses.

The techniques, methods, devices, and systems described herein have several advantages over conventional techniques, methods, devices, and systems of determining a patient's blood pressure, such as, for example, using a cuff sphygmomanometer and taking manual readings at periodic intervals or an invasive arterial line. For example, conventional readings are spaced far apart, e.g., by several minutes, or even hours, to provide information needed for time-sensitive decisions in an in-hospital or other critical care setting. For instance, when patients are under sedation or otherwise undergoing a surgical or other medical procedure, serious adverse events involving swings in the patient's underlying blood pressure can develop in a matter of seconds. This is problematic since a caregiver may need to react quickly to hypotensive or hypertensive conditions in the patient by taking appropriate corrective action. Invasive systems, e.g., an arterial line, present additional risks or contraindications, thus limiting their use in many cases. Thus, example devices according to various embodiments are advantageously capable of providing caregivers with critical time-sensitive, near continuous blood pressure information to make critical care decisions. A further advantage is that such devices, according to some embodiments, can monitor the blood pressure and/or other arterial pulse measures non-invasively because of external placement of these devices. Further, the devices according to some embodiments, are ambulatory devices, capable of and designed for moving with the patient as the patient goes about his or her daily routine. As such, blood pressure monitoring via the techniques, methods, devices, and systems herein can advantageously be carried out in out-patient settings, e.g., in the patient's home or office.

The wearable sensor(s), according to some embodiments, comprises ECG acquisition and processing circuitry can be physically housed within a same enclosure or unit as the radio-(RF) frequency based radar and associated circuitry (and/or software running on a processor performing some or all of the functionality of the circuitry). To overcome potential interferences between the two types of acquisition and processing circuits, in some embodiments, certain steps are taken which can include, for example, separation between of the grounds for the digital circuitry and the RF components, providing shielding for the RF radar components, using different power paths for the ECG processing and other digital circuitry from that of the RF radar components, and further, using filters in the digital circuits to minimize noise effects, implementing ECG filtering to minimize RF high frequency signals, and designing the circuit layout such that ECG signal paths are physically separated from the RF signal paths.

The system may further comprise, according to some embodiments, a patch for housing the sensor(s) and/or attaching the sensor(s) to the surface of the patient. In addition, the system can include a wireless gateway (GW) for linking the device and/or sensor(s) to an external or outside server. The server can be configured to analyze the continuously transmitted ECG data from the wearable device comprising the sensor(s), and includes, for example, databases, automated analysis algorithms, reporting tools, and may also include a web interface (e.g., touchscreen that facilitates interaction between the system and a user such as a patient or health care provider). In some embodiments, the gateway may also include a gateway display, which may be a touchscreen or a touch sensitive screen. Various electronic components of the arrhythmia and fluid monitoring sensor(s) including, for example, the controller, ECG leads (a pair, for example), ECG circuitry, accelerometer (three-axis), RF antenna integrated PCB, RF circuitry, and power source (e.g., battery), which may all be enclosed within reusable, hermetically sealed slender housing made of plastic material (such as a cartridge).

Figure 1B:
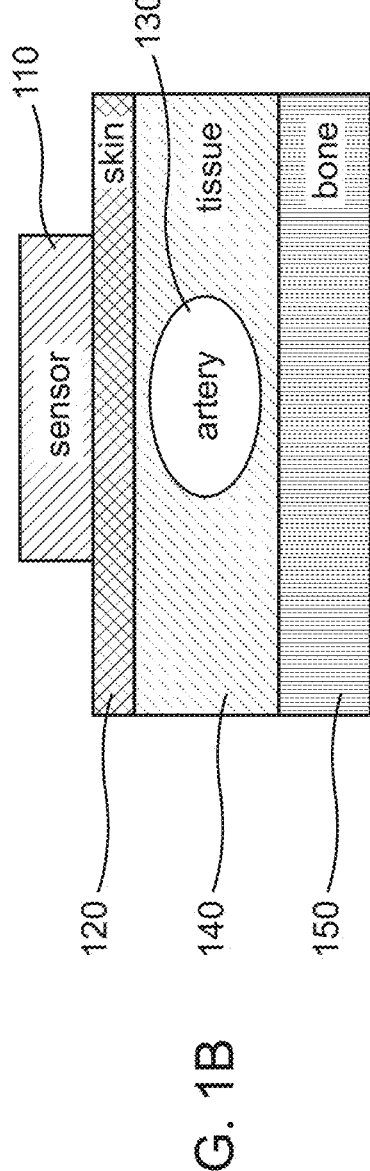
FIG. 1B shows an example schematic illustration of the placement of an RF-based monitoring device in the vicinity of an artery to be investigated, according to some embodiments.

FIG. 1B shows an example schematic illustration of the placement of an radio frequency (RF)-based monitoring device in the vicinity of an artery or tissue to be investigated, according to some embodiments. In some embodiments, the RF-based monitoring device or sensor 110 including a radar can be placed on an arm of a patient, a leg of a patient or any other location on a patient's body that allows the radar proximate access to an artery. For example, the sensor 110 may be placed in contact with the skin of the patient 120 at the wrist or the ankle. The contact may be direct, i.e., without any other object placed in between the sensor 110 and the skin 120 or it may be indirect, i.e., via other materials such as clothing, gels, etc. In some embodiments, the positioning of the sensor 110 on the skin 120 may be configured to allow RF waves transmitted by the radar to travel the measurement range (e.g., the depth of the distance between the sensor 110 and the artery 130 (as measured to the center of the artery, for example)), and be reflected back to the sensor 110. In some embodiments, the waves transmitted to, and/or reflected back from, the artery 130 may be analyzed to determine the properties of the artery 130, or changes thereof. In some embodiments, such analysis may also include analysis of the waves transmitted to and/or reflected back from the skin 120, the tissues 140 surrounding the artery 130, and nearby bones 150.

In some embodiments, an example of the properties of the artery 130, or changes thereof, that may be determined via the analysis of transmitted and/or reflected RF waves is the radar cross section (RCS) of the artery 130. In some embodiments, RCS can be understood as a measure of the amount of waves reflected back to an RF wave source in relation to the transmitted waves, and may include information about the reflecting object.

For example, the RCS may be a measure of the amount of the RF wave scattered by the artery as a function of the observation angle. In this respect, RCS can be expressed as a limit of {4*pi*d²(Sr/Si)} as d tends to infinity in the far field. Here, d is the distance of the artery from the antennas, and Sr and Si are reflected and incident power densities (W/m²) of the RF waves respectively. The RCS is given in units of m² and may be interpreted as a cross-sectional area of a perfectly reflecting sphere and which would isotropically re-radiate the incident field. The artery can be approximated as a circular cylinder, as shown for example in FIG. 1D.

Figure 1C:
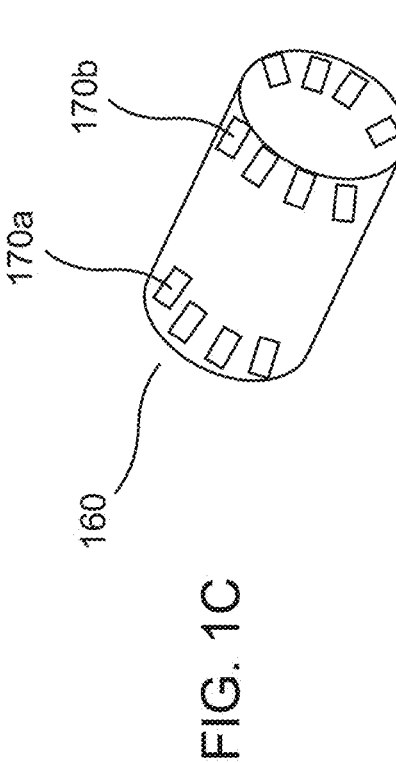
FIG. 1C shows an example schematic illustration of such a device as wrist-worn blood pressure detector, according to some embodiments.
Figure 1D:
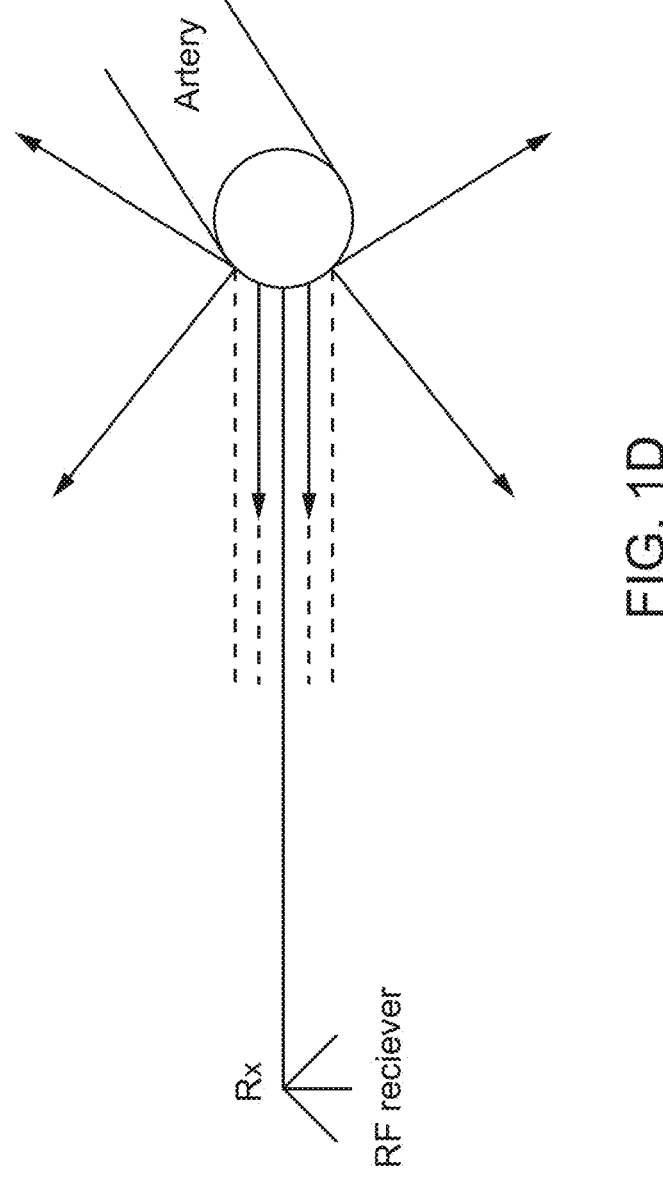
FIG. 1D shows an example schematic of the transmission to, and reflection from, an artery of an RF signal for use in monitoring the physiological conditions of a patient or subject, according to some embodiments.

As shown in FIG. 1D, the RF receiver, in some embodiments, receives only a portion of the reflected waves from the artery. In the schematic shown for example, the time-varying RCS measure can be calculated by modeling the artery as a circular cylindrical model of infinite length relative to the wavelength of the RF signals.

For example, during a cardiac cycle, since the diameter of the artery 130 varies over time, the time-varying RCS of the artery 130 extracted from an analysis of the waves reflected back to the sensor 110 may change over time as well, providing information on whatever caused the change in artery diameter. In some embodiments, from the measurements of a time-varying RCS, an arterial pulse waveform representing the pulse wave propagating through the artery 130 may be determined. For example, a reflected wave may be modulated by the artery 130 over the course of the cardiac cycle, and information from the reflected wave can be used to determine/estimate the arterial pulse waveform within the artery 130. Such a modulation may be caused by changes in the measurement range (the depth of the artery 130 or the distance from the sensor to the artery 130) over the course of the cardiac cycle, leading to changes in the phase of the reflected waves, which may be part of the information used to determine or estimate the arterial pulse waveform. In turn, from the arterial pulse waveform, a variety of clinical information can be obtained, such as, but not limited to: arterial stiffness, pulse wave velocity, cardiac output, blood pressure measurements (continuous or non-continuous) and atrial fibrillation. In some embodiments, the transmission of the waves by the sensor 110 or radar may be continuous or non-continuous (e.g., intermittent, periodic, etc.). FIG. 1C shows a schematic illustration of such a device as an exemplary wrist-worn blood pressure detector, according to some embodiments. In some implementations, the detector may be worn about a leg or other body portion of the patient (e.g., and modified to fit a shoulder, torso, and the like). Radar antennas 170*a, b,* arranged cyclically around the device 160, may transmit and receive waves so as to facilitate the analysis of the waves and the determination of clinical information as discussed above. In some embodiments, the antennas 170 may be configured to receive not only their own reflected waves, but also waves transmitted from other antennas located across from them.

Figure 2A:
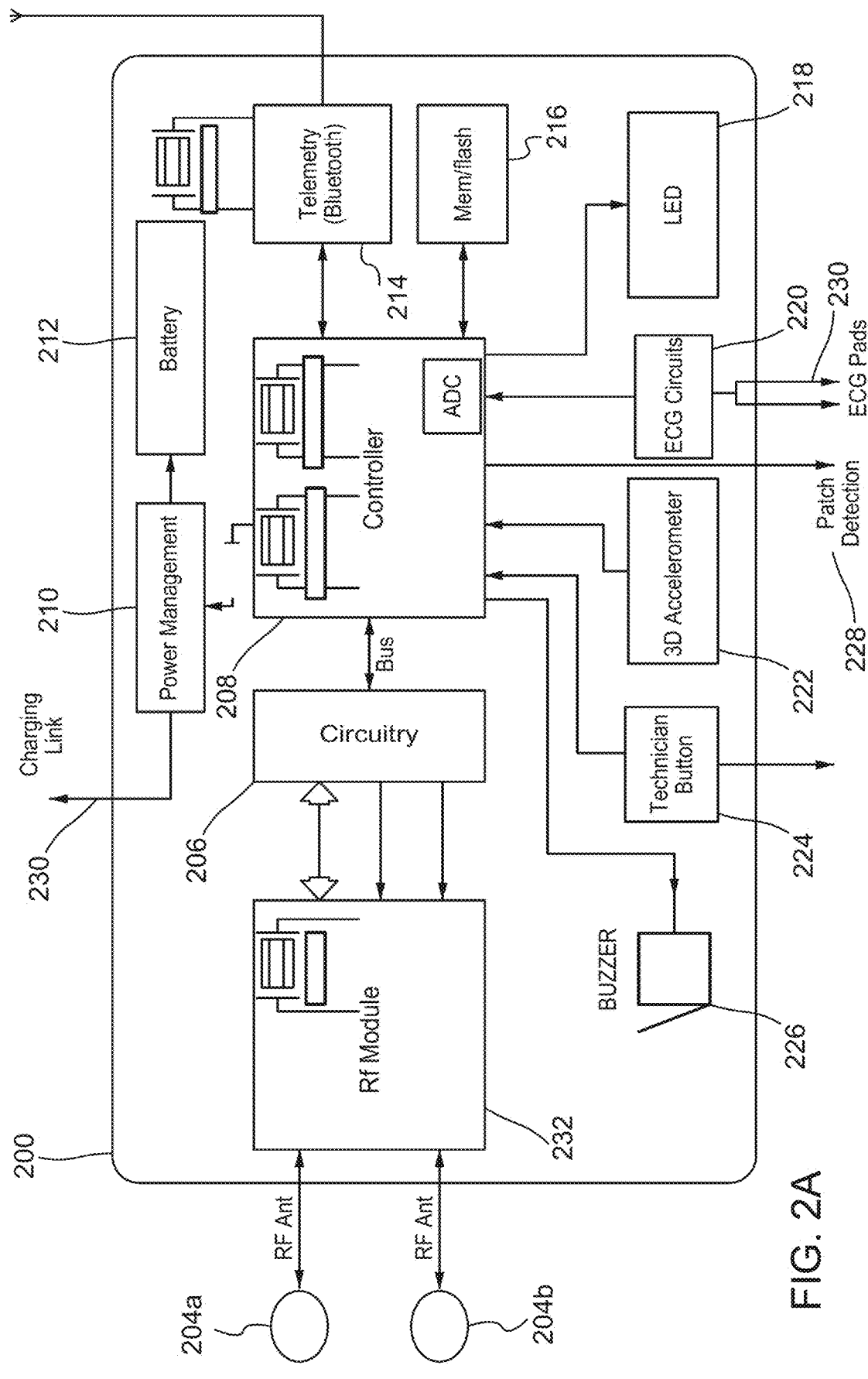
FIG. 2A shows an example illustration of device electronics architecture for measurements and transmission of patient physiological data, according to some embodiments.

With reference to FIG. 2A, in some embodiments, an RF-based monitoring device or sensor includes RF antenna(s), an RF module and circuits for controlling the module (e.g., field-programmable gate array (FPGA) circuits). The sensor 200 can include external interfaces such as but not limited to one or more RF antennas (e.g., bi-static) 204*a,* 204*b* for at least one of transmitting and receiving RF signals, a button or switch 224 for activating or deactivating the sensor 200, an LED 218 and a buzzer 226 for providing light and audio feedback to a user of the sensor 200, a battery charging link 230 coupled to a power management module 210 for charging an onboard power source such as a battery 212, and electrocardiogram (ECG) circuits 220 and pads 230 for at least one of sensing and recording synchronization signal. The ECG synchronization signal may be used, e.g., for gating the RF transmission cycles to an ECG of the patient. In some embodiments, the sensor 200 may also include a wireless link (e.g., Bluetooth®) (not shown) to provide an external server access to the sensor 200 to exert at least some control on the sensor 200.

In some embodiments, the sensor 200 may include a controller 208 (which may be implemented as a microprocessor or microcontroller in some implementations) that includes instructions operating thereon for specifying at least one of how measurements (RF, ECG, accelerometer, etc.) are taken, analyzed, and transmitted, how to relay the status of the sensor 200, how/when the sensor 200 can enter the plurality of sleep levels, and/or the like. In some examples, controller 208 may comprise two or more controllers. For instance, a first controller may be configured with instructions operating thereon to cause the controller to control at least one of generation, transmission, and other signal processing functions relating to the RF signals. A second controller may be configured with instructions operating thereon to cause the controller to at least one of implement specialized arrhythmia detection algorithms, handle noise discrimination, and/or communications control with a remote server. In such implementations, the two controllers may access a shared memory 216 (which, of course, can also be used with a single controller), where the first controller can store RF signal information for a predetermined period of time (e.g., 15 seconds, 30 seconds, 1 minute, or more). The second controller may access the RF signal information in the shared memory for one or more operations as listed above. In some embodiments, the instructions may also specify the conditions for performing certain types of measurements. For example, the instructions may specify that the accelerometer may not commence measurements (for physical activity, and patient posture, for example) unless the user of the sensor is at rest or maintaining a certain posture. As another example, the instructions may identify the conditions that may have to be fulfilled before ECG measurements can commence, such conditions including at least sufficient attachment level between the sensor and the surface on the body to which the sensor 200 is attached. In some embodiments, the controller 208 may have internal and external non-volatile memory banks that can be used for keeping measurement directory and data, scheduler information, and/or a log of actions and errors. This non-volatile memory allows power saving via a total power-down while retaining data and status information.

Figure 2B:
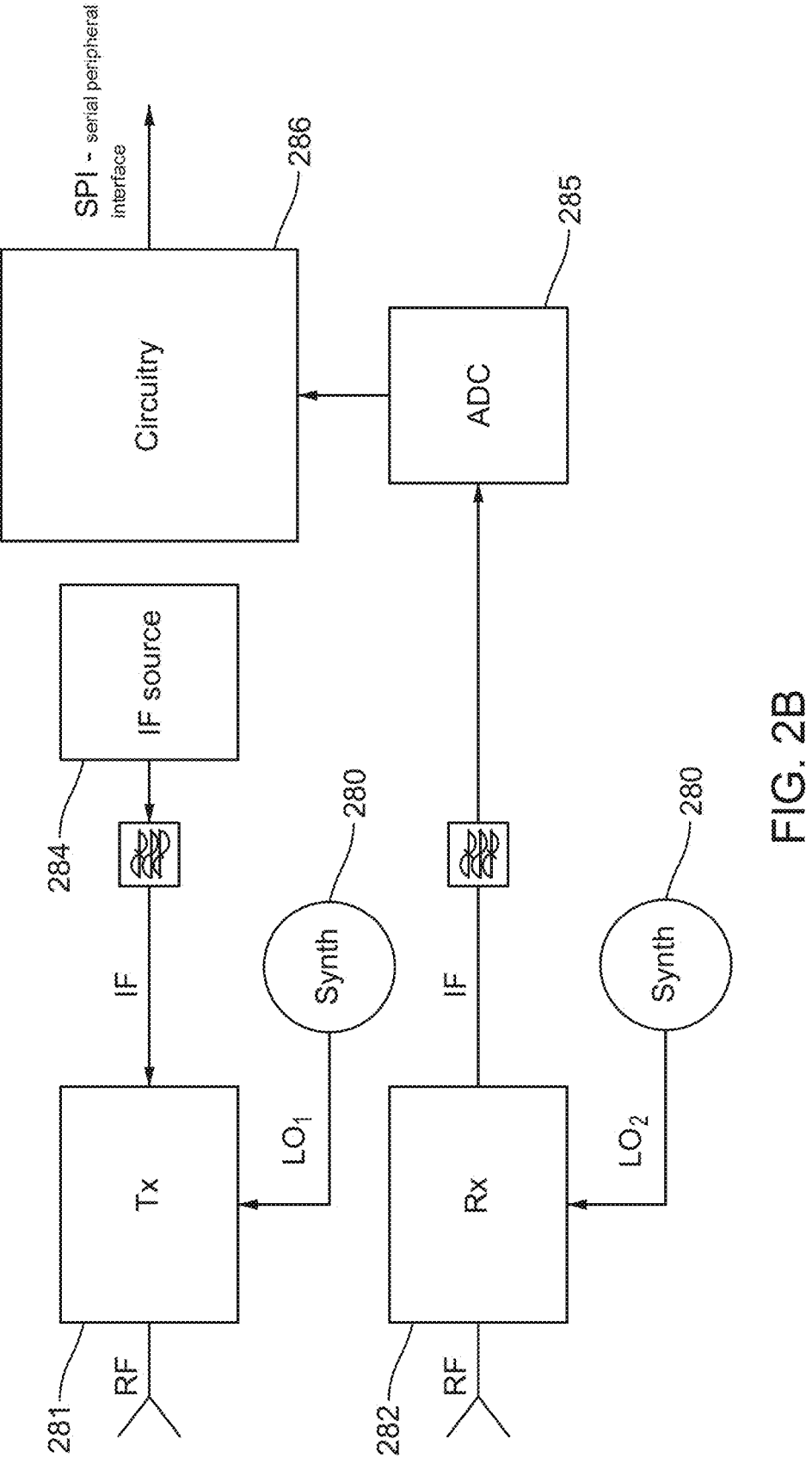
FIGS. 2B-C show block diagrams of example implementations of architecture of radio frequency (RF) modules, according to some embodiments.
Figure 2C:
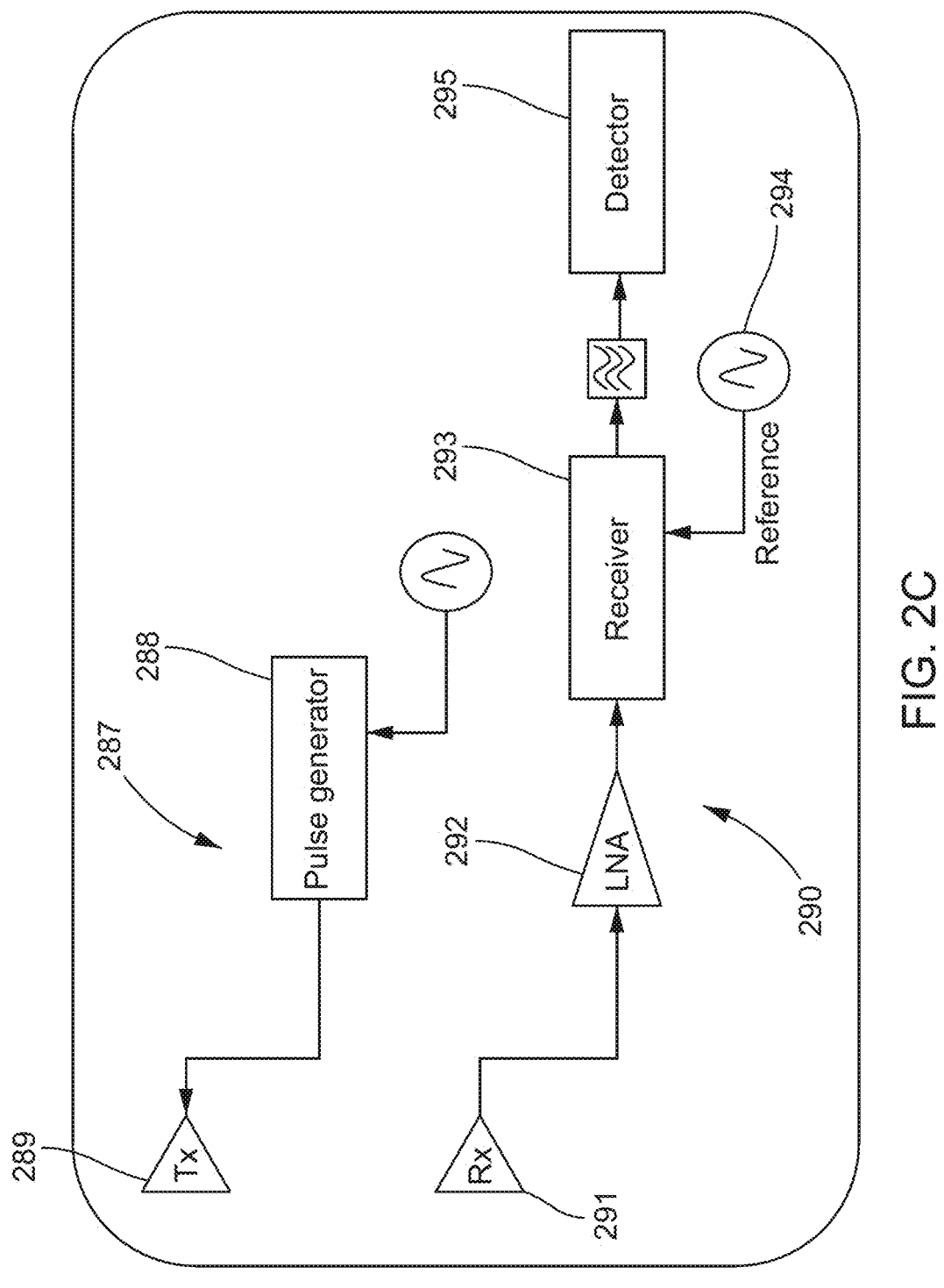

FIGS. 2B and 2C are block diagrams that illustrate examples of RF sensor functionality disposed within an RF module (e.g., RF module 232), according to some embodiments. Referring first to FIG. 2B, initially, one or more RF signals (e.g., a single "local oscillator (LO)" signal, or different "$LO_1$" and "$LO_2$" signals, collectively "LO" signals) can be generated by a broadband synthesizer 380 (e.g., a pulse generator and synthesizer—LO). Such a synthesizer 280 can include moderate phase noise performance and fast settling time capabilities (in some embodiments, one or the other). The RF module can include a transmitter portion 281, including a transmitting antenna (Tx) and associated circuitry for transmitting RF waves directed, for example, towards a tissue of interest in the patient's body, and a receiver portion 282, including a receiver antenna (Rx) and associated circuitry for receiving reflected RF waves from, for example, the tissue of interest in the patient's body.

The LO signal at the transmitter portion 281 is multiplied with an external sine wave at a low frequency intermediate frequency (IF) signal, generated by an IF source 284, and directed to the output of the transmitter (Tx). As noted above, the LO signal at transmitter portion 281 and the receiver portion 282 can be generated by one or two LO sources (e.g., synthesizer(s) 280). Output power can be controlled via digital control of a digitally controlled attenuator (DCA) on the RF transceiver path. An external reflected RF wave returning to a receiving antenna (Rx) may be directed to the receiver portion and down-converted to an IF frequency by a down conversion mixer. The reflection characteristics (phase and amplitude) can be transformed to a new IF carrier (e.g., on the order of 250 KHz), filtered and amplified before the analog-to-digital converter (ADC) 285.

Digital control for the functionality may be achieved directly by a processor and/or digital logic circuitry (e.g., a circuitry 286), which may be configured to control both the transceiver's configuration process, IF signal adjustments and associated switching.

Referring now to FIG. 2C, in some embodiments, the RF module 232 may be implemented using a transmitting portion 287 and a receiver portion 290, as shown. For example, the transmitting portion can include a pulse generator 288 and a transmitting antenna Tx 289 for transmitting the RF waves directed towards a tissue of interest in the patient's body. The receiver portion 290 may include a receiving antenna Rx 291, a low-noise RF amplifier 292, a receiver 293 that converts the reflected RF signals to an IF signal by using mixer and local oscillator 294, which may be a monostatic (sheared LO) or a bi-static system. The signal can be filtered, amplified and fed in to a detector 295, the output of which may be connected to additional circuitry for further signal processing.

With respect to potential RF/ECG interference, in some embodiments, the following steps can be taken (in some embodiments, only one, in some embodiments, a plurality, and in some embodiments, all):

Ground Separation between digital and RF components: may be achieved by separating the digital and RF grounds, and utilizing a single connection point (for example) through ferrite bead.

RF module shielding may also be used which may comprise a metallic cover, for example, radio frequency shield 290 as shown in FIG. 2C.

Power circuity considerations: different power paths may be utilized for different components/modules. Additionally, the power circuit may include filters to avoid noise.

ECG filtering may also be used to aid in minimizing RF interference which prevents high frequency signals interfering with the ECG circuitry/module. and Circuitry layout: ECG signal paths may be physically separated from RF paths. In some embodiments, the ECG signal paths can also be physically separated from other lines that might interfere.

FIG. 2C shows a non-limiting example of a general architecture of the RF module with low frequency IF and shared local oscillator (LO). Accordingly, the transmitted RF signal may be mixed with the IF signal (e.g., about 250 KHz) before transmission, so the transmission is actually 2 tones around the carrier RF signal, separated by about 500 KHz.

Figure 13A:
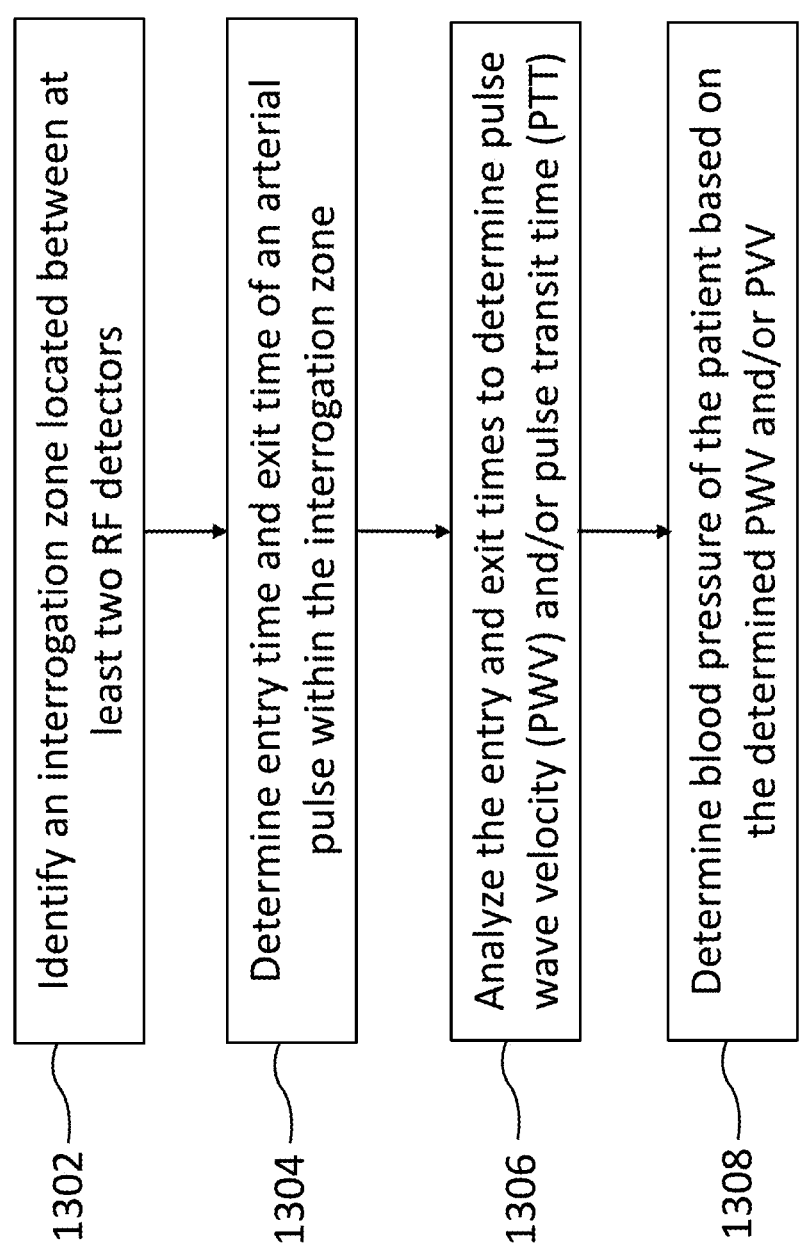
FIG. 13A shows example flowchart illustrating the process of detecting blood pressure of a patient using the RF-based monitoring device disclosed herein, according to some embodiments.
Figure 13B:
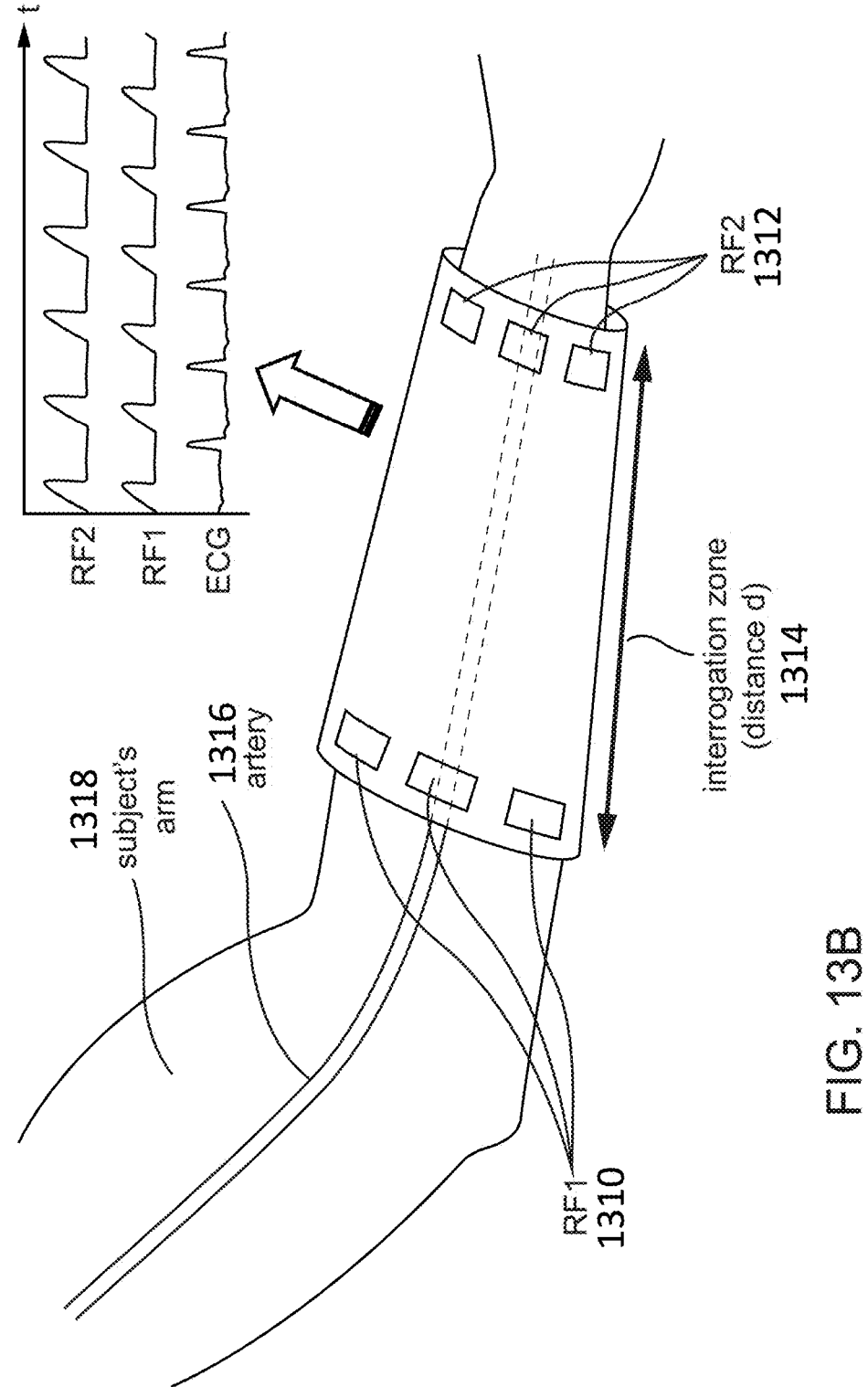
FIG. 13B shows example implementation of the RF-based monitoring device disclosed herein as worn around the lower portion of a patient's arm, according to some embodiments.

In some examples, the plurality of RF antennas (e.g., RF antennas 204a, 204b) and associated circuitry (e.g., RF module 232, transceiver 281, or receiver 282) may be implemented on a separate device from the rest of the RF transmitting, monitoring, and processing circuitry. For example, the RF antennas and associated circuitry may be mounted on, mounted within, or otherwise disposed on or within a structure adapted to be worn on a portion of the patient's body. For instance, the RF antennas and associated circuitry may be disposed within or on a wrist and/or forearm-worn device (as shown in FIG. 13B below). For example, the controller 208, power management circuitry 210, battery 212, and other components may be housed within a single housing (in some embodiments, multiple housings) distinct from the body worn device. The body worn device can be electrically coupled via a cable or other wire to the controller 208 (and additional or optional components) that is configured to control and/or process the transmitted RF and reflected RF waves from the RF antennas. In some embodiments, the controller may be activated (or some other functionality may be conducted), upon detecting 228 use of a patch.

In some implementations, the body worn device may be in wireless communication with the controller 208 (and additional or optional components). For example, in a hospital setting, a patient may be fitted with the body worn device (such as the one shown in FIG. 13B), while the controller 208 and other components described above may be housed within a separate device and placed at the patient's bedside. In some examples, wireless interface circuitry disposed in the body worn device can facilitate the communication of RF data between the body worn device and controller 208. For example, the wireless interface can include communications circuitry for transmitting RF-based data in accordance with a Bluetooth® wireless standard to the controller 208. Other technologies or standards of communications that may be implemented for such purposes including broadband cellular network communication standards (e.g., 2.5G, 2.75G, 3G, 4G, 5G cellular standards, and/or Long-Term Evolution (LTE) technology or GSM/EDGE and UMTS/HSPA technologies for high-speed wireless communication) or Wi-Fi™ communications standards based on the IEEE 802.11 standard.

In some embodiments, the RF module 232 may include a calibration path (e.g., an electric reflector such as but not limited to a resistor on board) which generates a steady and constant or near-constant reflection uncorrelated with the external propagation path. This reflector can be configured to generate a reflection profile with minimal dependencies to temperature, system noise and/or device location on the body.

In some embodiments, the RF module 232 itself may not have any processing components inside. For example, it may be controlled by a field-programmable gate array (FPGA) that defines in each or nearly each frequency point one or more of the frequency, output power levels, system gain, bypassing modes and/or enable/disable transmissions.

In some embodiments, the RF module 232 may support different types of waveform configurable options, including but not limited to normal operation, calibration frame operation, interleaved switching between normal and calibration frame operation, interleaved switching between normal and delayed path operation, and clear channel sensing. In some embodiments, for example the normal and interleaved switching ones, the attenuation may be different per frequency, while in the case of clear channel sensing, there may not be any transmission. For the calibration frame operation, the attenuation can be the same for all frequencies but may be higher when compared to those of the normal operation.

In some embodiments, the transmit (Tx) and receive (Rx) switches may be respectively set to transmit and receive through a calibration path for the case of calibration frame operation, while for the clear channel sensing, Rx switch may be set to antenna and Tx to calibration path. For interleaved switching between normal and calibration frame operations and between normal and delayed path operations, in some embodiments, the Tx and Rx switches may alternate between calibration and antenna path per frequency, and normal and delayed path, respectively.

In some embodiments, the RF waves may be in the frequency ranges, for example, from about 100 MHz to about 1 GHz, 200 MHz to about 2.5 GHz, from about 200 MHz to about 3 GHz, from about 500 MHz to about 5 GHz, including values and subranges therebetween. In some embodiments, the dynamic range is no less than 100 dB, measured in the presence of a strong coupling signal between transmission & reception. Further, the waveform may be stepped frequency (16-128 frequencies), arbitrary with 1 MHz accuracy & resolution. In some embodiments, actual frequencies selected may be contiguous or not, depending on regulatory requirements. In some embodiments, the dwell and settling times 321a may be configurable to allow 16-128 frequencies within less than 5 to 20 ms, respectively.

In some embodiments, the sensor may include indicators providing information on the attachment level of the sensor to a skin of the patient to which the sensor is attached. Such information may be obtained from RF-based measurements as discussed in PCT International Patent Publication No.; WO2016/115175, filed Jan. 12, 2016, titled "Systems, Apparatuses, and Methods for Radio Frequency-Based Attachment Sensing," the disclosure of which is incorporated by reference herein in its entirety.

In some embodiments, the circuitry 206 (e.g., comprising logical and/or computational circuit components, such as FPGA circuitry) may be configured to interface with the RF module 232. For example, the circuitry 206 can be configured to one or more of control the transceiver module, control the RF discrete pins, control the ADC module, generate the IF signal for the RF module 232, and acquire ADC (analog-digital conversion) output samples, synchronized with the generated IF signal. Further, in some embodiments, the circuitry 206 can be configured to process the ADC output samples to generate the baseband data. In addition, in some embodiments, the circuitry 306 may be configured to interface with the controller or controller 208. For example, the circuitry 206 may start RF transmission (per frame) upon command from controller 208, save baseband data to local RAM, per frame, for controller 208 to read, allow controller 208 read/write transactions towards configuration memory, provide a debug interface for the controller 208, and/or allow controller 208 to change configuration settings using a dedicated memory.

In some embodiments, the circuitry 206 can support, for example, up to 128 frequencies, allowing for a different gain and dwell time per frequency. In some embodiments, power consumption can be minimized by using several clock frequencies within the design and gating unused clock signals. In some embodiments, controller data acquisition can be performed using a separate clock, allowing the shut-down of the entire control & processing pipe while reading the data.

In some embodiments, the sensor disclosed herein may comprise an accelerometer and the accelerometer may be used to determine one or more of the physical activity, posture and respiration rate of a patient wearing the sensor. For example, an accelerometer 222 (e.g., a three-axis (3D) accelerometer) may be used to acquire data on patient movements and posture as well as the respiration rate, and a processor (of the sensor or an external server, for example) receiving the acquired data may use the data (e.g., in conjunction with data obtained by the sensor such as ECG data or RF-based measurements) to determined physiological parameters of the patient. The accelerometer 222 may be used to aid RF and/or ECG analysis by detecting different types of motion segments in the recording so that the conditions of the measurements of the RF and/or the ECG may be interpreted/analyzed accordingly. For example, in some embodiments, RF and/or ECG measurements may be performed while the patient wearing the sensor is active or at rest. The analysis of the RF and/or ECG data may then depend on the state of the patient's physical activity (e.g., at rest, low intensity activity, high intensity activity, etc.). In such embodiments, the accelerator may be used to identify the patient's physical state so as to properly analyze and interpret the RF and/or ECG measurements.

In some embodiments, the accelerometer 222 (or other sensor) may also contain an internal tap detector, which may be used for generating a patient triggered event (e.g., using "double tap", or plurality of taps, feature). The acceleration signal can be used to calculate respiration rate. FIG. 2A shows an example embodiment of a sensor comprising a 3D accelerometer 222, RF antennas 204a, 204b, ECG processing circuitry coupled to ECG electrodes, a controller 208

(which may be alternatively referred as a processor) and telemetry (e.g., Bluetooth®) 214. In such embodiments, for example, the micro-controller 208 may receive data on patient respiration rate, movements, posture, ECG as well as RF-based measurements of the patient and process, and/or transmit to an external processor via the telemetry 214 for further processing, to determine a physiological parameter of the patient. As an example, the micro-controller 208 of the sensor may cause the Bluetooth® telemetry 214 to transmit the noted data and measurements to an external server which in turn analyzes the RF measurements, the ECG, posture, movement, and/or respiration rate data to determine the lung fluid level of the patient. As in another example, the external server may analyze ECG data to determine patient health conditions related to, for example, one or more of a heart rate, atrial fibrillation, flutter, supraventricular tachycardia, ventricular tachycardia, pause, atrioventricular (AV) block, ventricular fibrillation, bigeminy, trigemini, ventricular ectopic beats, supraventricular ectopic beats (SVEB), bradycardia, and tachycardia. The determination of patient physiological health parameters (e.g., any of the above-noted health conditions) may allow the server to provide a notification on health-related events of the patient wearing the sensor for which the data came. For example, upon determining an arrhythmia condition from data received from a sensor, an external server may provide a notification indicating a cardiac event with respect to the wearer of the sensor that transmitted the data.

In some embodiments, the sensor may also include one or more of any of: a temperature sensor, a conductance sensor, a pressure sensor, a respiration sensor, SPO2 (a peripheral capillary oxygen saturation sensor), and/or a light sensor. For example, a respiration sensor can include an accelerometer configured to monitor the patient's chest movements, e.g., during certain portions of the day and/or night or during an RF measurement. For instance, a 3D multi-axis, multi-channel accelerometer can be configured to, on a first channel, monitor for a patient movement and/or posture, and on a second, different channel, monitor the chest movements of the patient to determine respiration rate and other related data. Alternatively, a respiration accelerometer can be provided in the device that is separate from a posture sensing accelerometer. In some examples, the respiration rate measurement can be based on the operation of a tri-axis micro-electromechanical system (MEMS) accelerometer within the device mounted on the patient's torso. The accelerometer can measure projections of the gravity vector on its intrinsic axes. From these measurements, a respiration rate can be derived based on measured quasi-periodic changes of the projections that occur due to respiration movements of the patient's rib cage.

In other examples, the respiration rate and/or other respiration data can be derived from the RF signals themselves. For example, dedicated respiration circuitry can be provided and/or the processor can be configured with instructions to cause the processor to monitor the reflected RF waves as described herein and determine respiration rate and related data therefrom. In some embodiments, respiration characteristics such as exhale vs. inhale times can also be measured via an accelerometer and health conditions such as sleep apnea may be detected from accelerometer measurements.

In some embodiments, as noted above, transmitted and/or the reflected waves can be analyzed to measure or estimate the RCS of an artery in the vicinity of a sensor, thereby allowing for the determination of clinical or physiological information of the patient using the sensor. In selecting the waves to transmit to the arteries, as well as in receiving the waves reflected back from the arteries, it may be desirable to identify the strongest and/or clearest signals as described further below to obtain robust data or information on the patient's conditions.

Figure 3A:
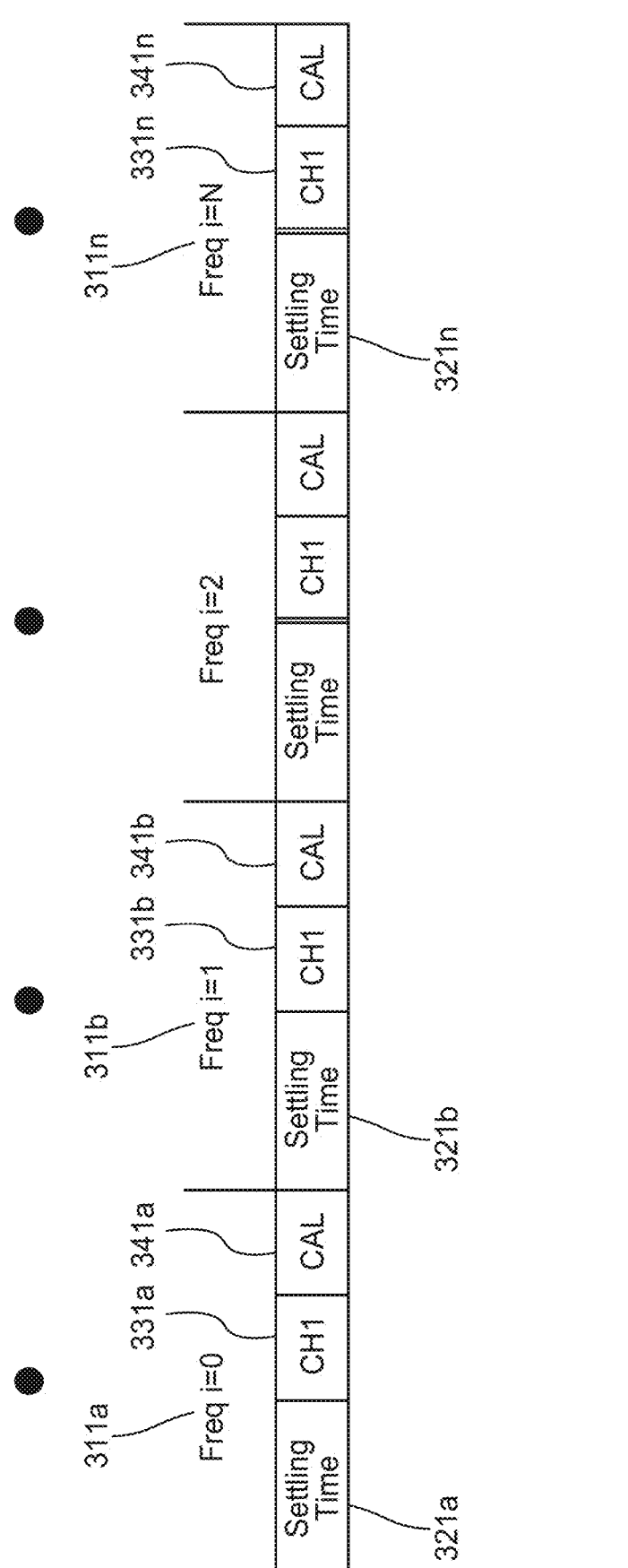
FIG. 3A shows an example illustration of the processing of transmitted and/or received signals that relate to physiological data of a patient using the RF-based monitoring device disclosed herein, according to some embodiments.
Figure 3B:
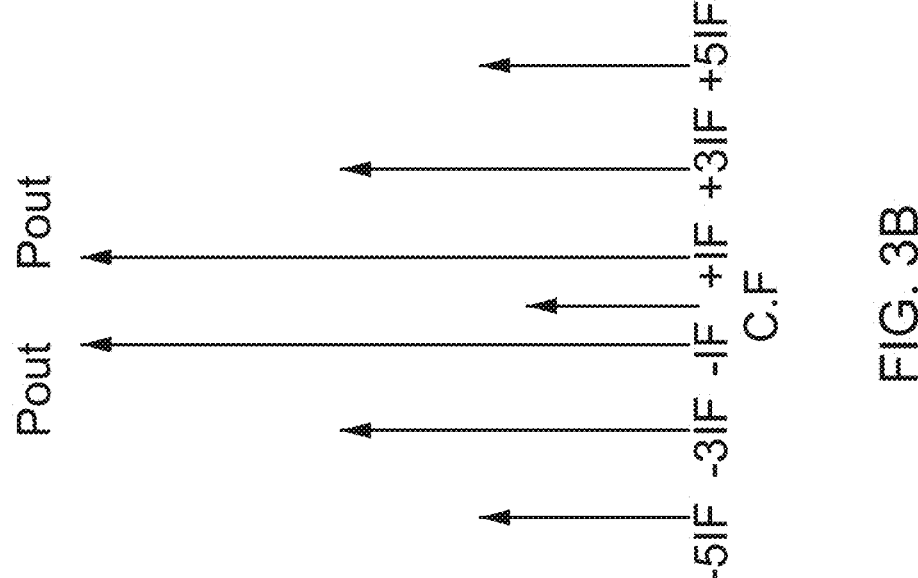
FIG. 3B shows example results of such signal processing, according to some embodiments.

FIGS. 3A-B show example illustrations of the processing of transmitted and/or received signals that relate to physiological data of a patient using the sensor disclosed herein. In some embodiments, the signal processing identifies frequency components of signals with strong power level for transmitting to an artery being monitored or investigated. Further, the processing can also identify strong/clear reflected arterial radar signals corresponding to some predetermined depth within the body of a patient (e.g., depth or distance to an artery at the wrist of the patient).

With reference to FIG. 3A, in some embodiments, a frame-based signal processing technique/methodology is shown, where the transmitter of the sensor 110 steps through a plurality of frequencies 311*a*, . . . , 311*n* in each frame (indexed by the variable i). That is, each frequency 311*a-n* corresponds to a slot in the frame, and represents a period where the synthesizer 380 generates an LO signal at a new frequency. After an initial settling time 321*a-n*, in some embodiments, the transmitter may transmit a carrier wave ("CW") signal for the dwell time 331*a-n* (denoted CH1). Each slot also includes an optional calibration period 341*a-n* (denoted by "CAL" in the figure) that can be used to calibrate the circuitry in preparation for the next slot. In some embodiments, the settling time may be in the range from about 50 μs to about 200 μs, from about 75 μs to about 175 μs, from about 100 μs to about 150 μs, about 120 μs, including values and subranges therebetween. In some embodiments, the dwell time may be in the range from about 50 μs to about 150 μs, from about 75 μs to about 125 μs, about 100 μs, including values and subranges therebetween. The CW signal can be created by mixing a local oscillator ("LO") signal from a synthesizer with an intermediate frequency ("IF") signal, for example, as discussed above with reference to FIG. 2B-C. In some embodiments, the IF signal may be in the range from about 100 KHz to about 400 KHz, from about 150 KHz to about 350 KHz, from about 200 KHz to about 300 KHz, about 250 KHz, including values and subranges therebetween.

FIG. 3B shows an example embodiment of the resulting transmitted CW signal, which may be a "double sided" signal with a "center" frequency ("CF") that is at least substantially equal to the selected LO frequency created by the synthesizer for a slot. Accordingly, the CW signal may also include additional frequency components above and below the center frequency, spaced out from each other by an amount at least substantially equal to the IF. In some embodiments, the frequency components of the CW signal with the largest power level may appear at about 1IF above and below the CF (i.e., CF±1 IF). In some embodiments, weaker components may also appear above or below CF by amounts that are at least substantially equal to odd multiples of IF (i.e., weaker components may appear at CF±3IF, CF±5IF, etc.).

In some embodiments, the set of carrier frequencies that the transmitter steps through in each frame can be configurable. For example, one or more of the settling time, the dwell time, the radar signal amplitude, and/or the like, may be configured to achieve a CW signal with desired characteristics. In some embodiments, the set of frequencies may be preset. For example, in some embodiments, a set of about 16, about 32, about 64, about 128, etc., frequencies in the range from about 300 MHz to about 5 GHz, from about 400 MHz to about 4 GHz, from about 500 MHz to about 3 GHz, from about 530 MHz to about 2.105 GHz, including values and subranges therebetween, may be used to generate the carrier waves.

In some embodiments, in each slot, the incoming electromagnetic signals, that is, the signals reflected back from an artery or other tissues, can be picked up by the receiving antenna. For example, the receiving antenna may be active throughout the entire frame, and as such may be configured to pick up signals with several different frequencies. In some embodiments, the signal processing steps may include down-converting the received signals by mixing them with the same LO signal that was generated by the synthesizer for use in creating the transmitted signal. In some embodiments, using the same LO signal for down-conversion (i.e., on the receive chain) as was used for up-conversion (i.e., on the transmit chain) allows the system to cancel out or at least reduce the effects of noise that might be present in the LO signal, resulting in a received radar signal in the IF spectrum. When receiving this IF signal, in some embodiments, the sensor (or other component) may low-pass filter the signal and feed it into an ADC converter, which may sample the signal and produce a digital representation. In some embodiments, this digital representation of the signal can then be sent through a serial peripheral interface ("SPI") to logic circuitry (e.g., FPGA circuitry), which may then group all of the samples for each frame together and send the samples to a controller for writing or storing into memory.

In some embodiments, the signal processing steps may further include performing a time-domain transformation of the stored samples. For example, the transformation, which may include one or more of transformations such as a "chirp-Z" transform (CZT) or inverse fast Fourier Transform (IFFT), can result in a vector corresponding to each frame and containing an amplitude measurement for each frequency component. In embodiments where IFFT is used, a signal processing software can be used to filter unwanted frequencies and perform the IFFT, which may result in a time-domain signal representing the reflections of the transmitted radar signal from the artery being monitored. In some embodiments, the system may focus on portions of this time-domain signal that occur at specific times, with these time locations corresponding to specific depths (e.g., depths or distances to the artery) within the patient's body to isolate the desired arterial radar signals (e.g., strongest/clearest signals) as described below.

In one implementation, prior to determining actual RCS measurements, an adaptive algorithm (e.g., implemented by controller 208) can determine a desired artery RF depth or range. For example, the algorithm can identify one or more reflected RF wave(s) that have maximal pulsating amplitudes during an initial period of time. The initial period of time, for example, can be established during configuration of the device prior to use. For example, the initial period of time may be less than 2 seconds, less than 1 second, less than 500 ms, or less than 200 ms. For example, the initial period of time can be based on a plurality of successive arterial pulses (e.g., 5 pulses, 10 pulses, 15 pulses or more). During the initial period, the algorithm can scan the amplitudes of the received various RF reflections from the patient's body. One or more of these RF reflections may have pulsing amplitudes in accordance with the underlying arterial pulse rate of the patient. In some examples, an ECG signal of the patient (e.g., specifically the R waves) may also be used to correlate to the occurrences of the peak RF pulses. The adaptive algorithm determines for each pulsating RF waves an average of the amplitudes over a duration. The algorithm can then select the RF wave(s) that has the highest average amplitude(s) as the desired reflected RF wave(s) corresponding to the pulsating artery being monitored. In some implementations, the algorithm can select the RF wave(s) that has a highest number of peaks over a certain amplitude value as the desired reflected RF wave(s) corresponding to the pulsating artery being monitored.

In some embodiments, the raw radar returns can be translated using FFT to range related echos. The range resolution can be calculated using the formula $$\Delta R = \frac{c}{2\,\text{bandwidth}\sqrt{\kappa}},$$

where c is the velocity of light, $\kappa$ is tissue permittivity and bandwidth refers to the RF bandwidth. As an example, for an RF bandwidth of about 2 GHz and tissue permittivity (about 55, for example), the range resolution can be about 1 cm.

Figure 3C:
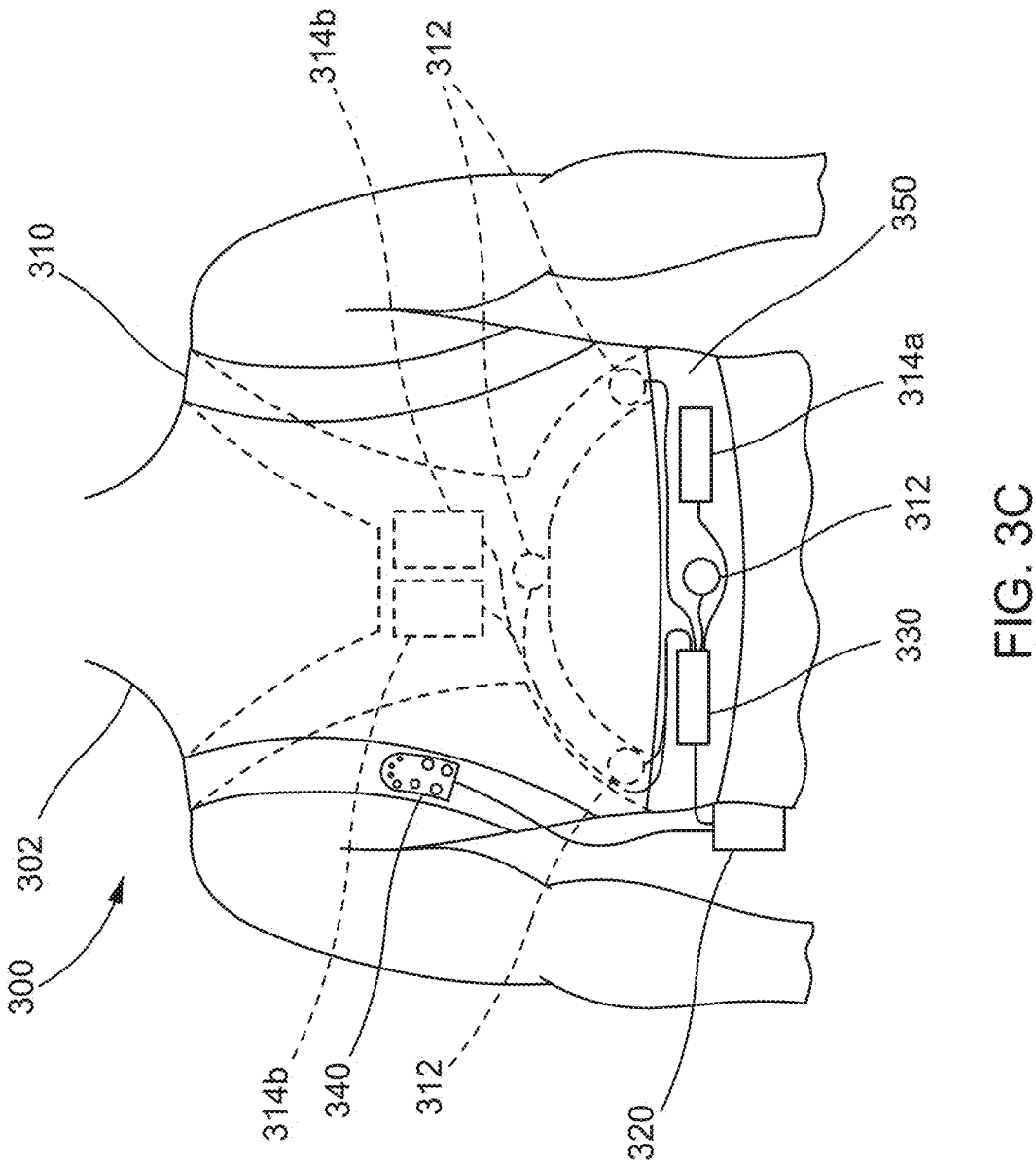
FIG. 3C shows an example wearable cardioverter defibrillator incorporating an RF-based monitoring device, according to some embodiments.
Figure 3D:
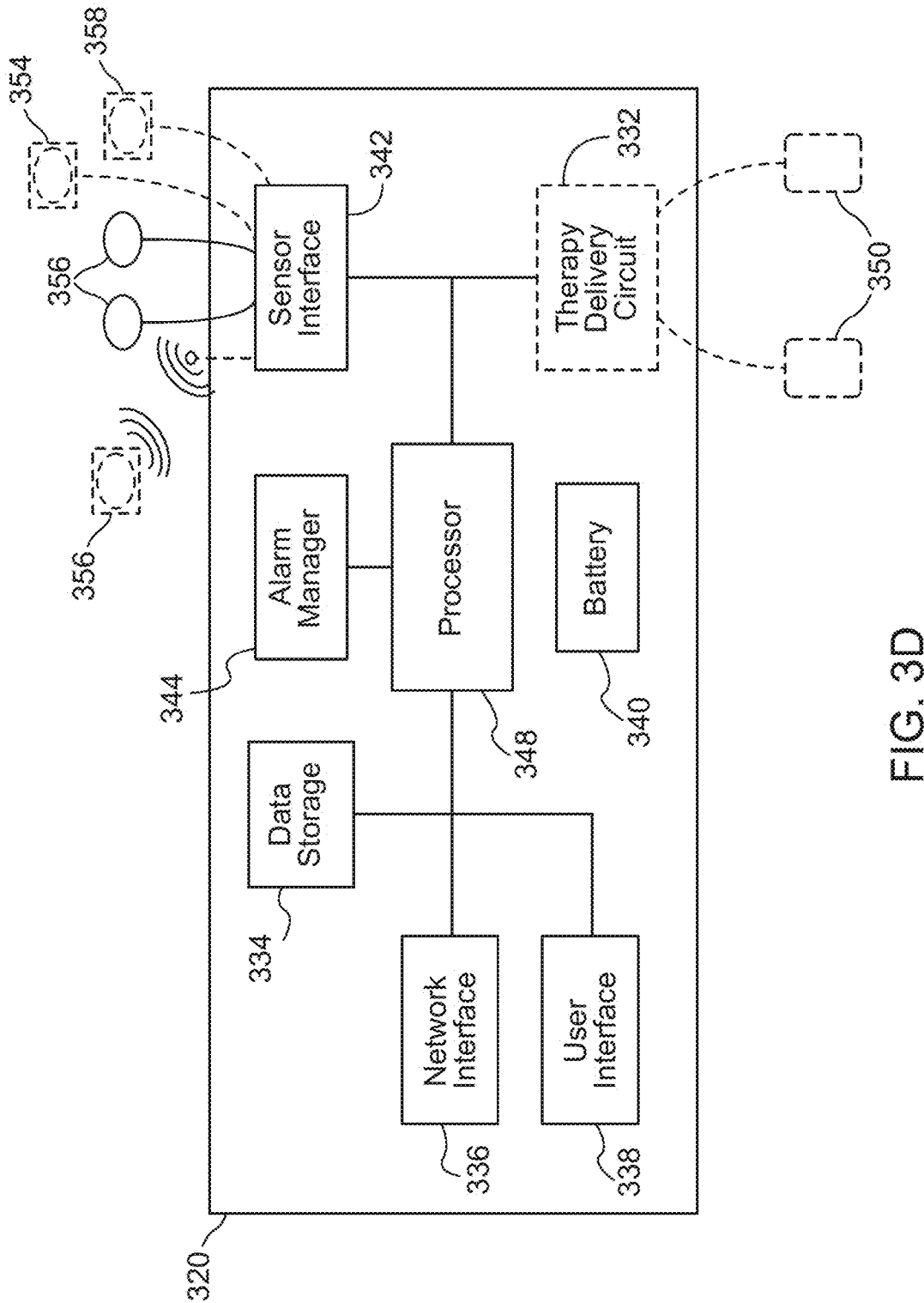
FIG. 3D shows an example wearable cardioverter defibrillator electronics architecture incorporating the RF-based monitoring device, according to some embodiments.

Referring to FIGS. 3C-3D, the radio-frequency radar device as described in various embodiments herein can be incorporated into a wearable cardioverter defibrillator system, according to further embodiments. For example, such a wearable cardioverter defibrillator can be the LifeVest® Wearable Defibrillator provided by ZOLL Medical Corporation (Chelmsford, MA).

FIG. 3C illustrates an example medical device 300 that is external, ambulatory, and wearable by a patient 302, and configured to implement one or more configurations described herein. For example, the medical device 300 can be a non-invasive medical device configured to be located substantially external to the patient. Such a medical device 300 can be, for example, an ambulatory medical device that is capable of and designed for moving with the patient as the patient goes about his or her daily routine. For example, the medical device 300 as described herein can be bodily-attached to the patient (e.g., LifeVest®, see above). Such wearable defibrillators are typically worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 300 can include one or more of the following: a garment 310, one or more sensing electrodes 312 (e.g., ECG electrodes), one or more therapy electrodes 314a and 314b (collectively referred to herein as therapy electrodes 314), a controller 320, a connection pod 330, a patient interface pod 340, a belt 350, or any combination thereof. In some examples, at least some of the components of the medical device 300 can be configured to be affixed to the garment 310 (or in some examples, permanently integrated into the garment 310), which can be worn about the patient's torso.

The controller 320 can be operatively coupled to the sensing electrodes 312, which can be affixed to the garment 310, e.g., assembled into the garment 310 or removably attached to the garment, e.g., using hook and loop fasteners. The controller 320 can be operatively coupled to the therapy electrodes 314. Additionally, component configurations other than those shown in FIG. 3C are possible. For example, the sensing electrodes 312 can be configured to be attached at various positions about the body of the patient 302, and can be operatively coupled to the controller 320 through, e.g., the connection pod 330. In some implementations, the sensing electrodes 312 can be adhesively attached to the patient 302. The sensing electrodes 312 can be configured to detect one or more cardiac signals, with examples of such signals including ECG signals and/or other sensed cardiac physiological signals from the patient. In certain implementations, the sensing electrodes 312 can include additional components such as accelerometers, vibrational signal detecting devices, and other measuring devices for recording additional parameters. For example, the sensing electrodes 312 can also be configured to detect other types of patient physiological parameters and vibrational signals, such as tissue fluid levels, cardio-vibrations, lung vibrations, respiration vibrations, patient movement, etc.

The connection pod 330 can, in some examples, include a signal processor configured to amplify, filter, and digitize these cardiac signals prior to transmitting the cardiac signals to the medical device controller 320. One or more of the therapy electrodes 314 can be configured to deliver one or more therapeutic defibrillating shocks to the body of the patient 302 when the medical device 300 determines that such treatment is warranted based on the signals detected by the sensing electrodes 312 and processed by the controller 320. Example therapy electrodes 314 can include conductive metal electrodes such as stainless steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 314 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or specific patient. Alternatively, the optional therapeutic elements can be deactivated (e.g., by means of a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

FIG. 3D illustrates a sample component-level view of the controller 320 (FIG. 3C) according to some embodiments. As shown, the controller 320 can include any of (and preferably several, and in some embodiments, all of) a therapy delivery circuitry 332, a data storage 334, a network interface 336, a user interface 338, at least one battery 340, a sensor interface 342, an alarm manager 344, and least one processor 348. A patient monitoring medical device can include the controller 320 that includes like components as those described above, but not include the therapy delivery circuitry 332 (shown in dotted lines).

The therapy delivery circuitry 332 can be coupled to one or more electrodes 350 configured to provide therapy to the patient (e.g., therapy electrodes 314 as described above in connection with FIG. 3C). For example, the therapy delivery circuitry 332 can include, or be operably connected to, circuitry components that are configured to generate and provide the therapeutic shock. The circuitry components can include, for example, resistors, capacitors, relays, switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuitry and under control of one or more processors (e.g., processor 348) to provide, for example, one or more pacing or defibrillation therapeutic pulses.

Pacing pulses, in some embodiments, can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

In some embodiments, the capacitors can include a parallel-connected capacitor bank comprising a plurality of capacitors (e.g., two, three, four or more capacitors). These capacitors can be switched into a series connection during discharge for a defibrillation pulse. For example, four capacitors of approximately 650 μF if can be used. The capacitors can have between a 350 to 500 volt surge rating and can be charged in approximately 15 to 30 seconds from a battery pack.

For example, each defibrillation pulse can deliver between 60 to 200 joules of energy. In some embodiments, the defibrillating pulse can be a biphasic truncated exponential waveform, whereby the signal can switch between a positive and a negative portion (e.g., charge directions). The therapy delivery circuitry 332 can be configured to perform the switching and pulse delivery operations, e.g., under control of the processor 348, according to some embodiments. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

Data storage 334 can include one or more of non-transitory computer readable media, such as, for example, flash memory, solid state memory, magnetic memory, optical memory, cache memory, and combinations thereof. The data storage 334 can be configured to store at least one of executable instructions and data used in the operation of the medical device (e.g., controller 320). In some embodiments, the data storage can include executable instructions that, when executed, are configured to cause the processor 348 to perform one or more functions (e.g., methodology steps enumerated in the present disclosure).

In some embodiments, the network interface 336 can facilitate the communication of information between the controller 320 and one or more other devices or entities over a communications network. For example, where the controller 320 is included in an ambulatory medical device (such as medical device 300), the network interface 336 can be configured to communicate with a remote computing device such as a remote server or other similar computing device. The network interface 336 can include communications circuitry for transmitting data in accordance with a Bluetooth® wireless standard for exchanging such data over short distances to an intermediary device(s), e.g., base station, "hotspot" device, smartphone, tablet, portable computing device, and/or other devices in proximity of the wearable medical device. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In some embodiments, the user interface 338 can include one or more physical interface devices such as input devices, output devices, and combination input/output devices and a software stack configured to drive operation of the devices. These user interface elements may render visual, audio, and/or tactile content. Thus, the user interface 208 may receive input or provide output, thereby enabling a user to interact with the controller 320. The controller 320 can also include at least one battery 340 configured to provide power to one or more components integrated in the controller 320. The sensor interface 342 can be coupled to one or more sensors configured to monitor one or more physiological parameters of the patient. As shown, the sensors may be coupled to the controller 320 via a wired or wireless connection. The sensors can include one or more electrocardiogram (ECG) electrodes 352 (e.g., similar to sensing electrodes 212 as described above in connection with FIG. 3C), bio-vibration sensors 354, RF-based monitors 356 (e.g., based on ultra-wide band radiofrequency devices), and a patient movement sensor 358.

The ECG electrodes 352 can monitor a patient's ECG information, and can be galvanic (e.g., conductive) and/or capacitive electrodes, configured to measure changes in a patient's electrophysiology to measure the patient's ECG information. The ECG electrodes 352 can transmit information descriptive of the ECG signals to the sensor interface 342 for subsequent analysis.

Bio-vibration sensors 354 can be included, in some embodiments, which can be configured to detect vibrations associated with, for example, heart and lung activity, of a patient. For example, the bio-vibration sensors 354 can be configured to detect heart vibration values including any one or all of S1, S2, S3, and S4. From these heart vibration values, certain heart vibration metrics may be calculated, including any one or more of electromechanical activation time (EMAT), percentage of EMAT (% EMAT), systolic dysfunction index (SDI), and left ventricular systolic time (LVST). The bio-vibration sensors 354 can include a vibration sensor configured to detect vibrations from a subject's cardiac system and provide an output signal responsive to the detected cardio-vibrations. The bio-vibration sensors 354 can also include a multi-channel accelerometer, for example, a three channel accelerometer configured to sense movement in each of three orthogonal axes such that patient movement/body position can be detected and correlated to detected heart vibrations information. The bio-vibration sensors 354 can, in some embodiments, transmit information descriptive of the cardio-vibration information to the sensor interface 342 for subsequent analysis.

In some embodiments, patient movement sensor(s) 358 can be included, and can include one or more accelerometers configured to measure motion data related to patient movement. In some embodiments, the patient movement sensor 358 can be configured to measure the number of steps a patient takes over a particular amount of time. For example, a patient may be instructed to perform a particular exercise such as a walk test. The patient movement sensor 358 can be configured to measure step and pace information during the particular exercise. It should be noted, however, that the patient movement sensor 358 is shown as a separate component by way of example only. In certain implementations, the one or more accelerometers included in the patient movement sensor 358 may be integrated into other components such as the bio-vibration sensors 354 or the tissue fluid monitors 356.

Motion information from sensor 358 can be used to track motion-related artifact and compensate and/or cancel the effects of such artifact in the RF measurements and/or ECG information. Additionally, or alternatively, based on the motion information, the devices/systems disclosed herein can determine a period of time when the patient is not moving or changing position long enough for a RF based blood pressure or other arterial pulse measure to be recorded (e.g., a duration of around 5 seconds, around 10 seconds, around 30 seconds, around 45 seconds, around 1 minute, around 2 minutes, around 5 minutes, around 10 minutes, around 20 minutes, around 30 minutes, or around 1 hour). For example, the device may be configured to take such measurements while the patient is asleep. For example, the device may be configured to receive a time of day or other such time based metric via a user-configurable parameter for when the measurement is to be taken. In such a scenario, the device may prompt the patient to lie down or sit still when the measurement is being taken (for example). For instance, the time of day may be set based on a predetermined schedule (e.g., every day at 8 PM). Alternatively or additionally, a caregiver may indicate at a remote server one or more values for the user-configurable parameter indicating the time of day when a measurement is to be taken. The remote server can upload or transmit the value of the parameter to the device in order to configure the device to prompt the patient to allow for the measurement to be taken.

The sensor interface 342 can be coupled to any one or a combination of sensing electrodes and other sensors to receive other patient data indicative of patient parameters. Once data from the sensors has been received by the sensor interface 342, the data can be directed by the processor 348 to an appropriate component within the medical device controller 320. For example, if heart data is collected by bio-vibration sensor 354 and transmitted to the sensor interface 342, the sensor interface 342 can transmit the data to the processor 348 which, in turn, relays the data to a cardiac event detector. The cardiac event data can also be stored on the data storage 334.

In some embodiments, the alarm manager 344 can be configured to manage alarm profiles and notify one or more intended recipients of events specified within the alarm profiles as being of interest to the intended recipients. For example, the alarm manager 344 may be used to implement the alert sequence as described in further detail below. In some implementations, the processor 348 includes one or more processors (or one or more processor cores) that each are configured to perform a series of instructions that result in manipulated data and/or control the operation of the other components of the medical device controller 320. In some implementations, when executing a specific process (e.g., cardiac monitoring), the processor 348 can be configured to make specific logic-based determinations based on input data received, and be further configured to provide one or more outputs that can be used to control or otherwise inform subsequent processing to be carried out by the processor 348 and/or other processors or circuitry with which processor 348 is communicatively coupled. Thus, the processor 348 reacts to specific input stimulus in a specific way and generates a corresponding output based on that input stimulus. In some example cases, the processor 348 can proceed through a sequence of logical transitions in which various internal register states and/or other bit cell states internal or external to the processor 348 may be set to logic high or logic low. The processor 348 can be configured to execute a function where software is stored in a data store coupled to the processor 348, the software being configured to cause the processor 348 to proceed through a sequence of various steps/logic-decisions that result in the function being executed. The various components that are described herein as being executable by the processor 348 can be implemented in various forms of specialized hardware, software, or a combination thereof. For example, the processor can be any one or more of: a digital signal processor (DSP), such as a 24-bit DSP processor, a multi-core processor, e.g., having two or more processing cores, and an Advanced RISC Machine (ARM) processor, such as a 32-bit ARM processor or a 64-bit ARM processor. The processor can execute an embedded operating system, and can include services (or service) provided by the operating system that can be used for any one or more of file system manipulation, display & audio generation, basic networking, firewalling, data encryption and communications.

The RF-based device(s) 356 may be configured to monitor fluid in tissue, that use radio frequency based techniques to assess fluid levels and accumulation in a patient's body tissue (see, e.g., U.S. Pat. No. 9,572,512, granted Feb. 21, 2017, hereby incorporated by reference in its entirety). For example, such tissue fluid monitoring functionality can be configured to measure fluid content in the lungs, typically for diagnosis and follow-up of pulmonary edema or lung congestion in heart failure patients. The tissue fluid monitors can include one or more antennas configured to direct radio frequency waves through a patient's tissue and measure output radio frequency signals in response to the waves that have passed through the tissue. In some embodiments, the output radio frequency signals include parameters indicative of a fluid level in the patient's tissue. The tissue fluid monitor(s) can be configured to transmit information descriptive of the tissue fluid levels to the sensor interface 342 for subsequent analysis.

In some embodiments, the RF-based device 356 can include arterial pulse monitoring as disclosed herein. For example, such an RF-base device 356 for monitoring arterial pulse waveforms may be located over the patient's artery and be coupled in a wired or wireless manner to the wearable defibrillator. For example, the RF based device may be implemented as a wrist-worn device and be configured to wirelessly transmit RF readings via Bluetooth® technology to the controller 320. In another implementation, the wrist-worn device may be coupled via a wire to the controller 320. In some examples, the wrist-worn device may be disconnected from the controller 320, e.g., by the patient by disengaging the wire running between the device 356 and the controller 320 or by turning off the wireless transmission between the device 356 and the controller 320. In some examples, the link between the device 356 and the controller

320 may be configured to not be decoupled by the patient during use of the wearable defibrillator.

As discussed above, in some embodiments, an RF-based monitoring device or sensor in proximity to an artery may be configured to transmit RF signals towards the artery and receive reflections back therefrom. To extract information/data related to the artery, in some embodiments, the reflected signals may be processed to isolate the signals that are reflected by the artery, as the reflected signals may include additional signals reflected from other organs such as the surrounding tissues and bones. For example, as discussed above, the reflected signals may be transformed into time domain signals and those time-domain signals that correspond to the distance or depth to the artery may be identified as the signals of interest for further analysis. In some embodiments, an adaptive algorithm as described above may be used to determine the depth or distance to the artery.

In some embodiments, after identifying the signals reflected from an artery under monitoring, the reflected signals may be processed to measure changes in the RCS of the artery, which relates to changes in the radius of the artery that may be caused by the arterial pulse waves propagating within the artery. In other words, in some embodiments, the time-varying RCS of the artery may be measured and the measurements may be correlated to the time-varying radius (or diameter) of the artery, which then allows for the determination of the arterial pulse waveforms in the artery. As such, in some embodiments, by analyzing the signals reflected from an artery, arterial pulse waveforms within the artery may be determined. In some embodiments, these waveforms hold clinical or physiological information of the patient such as, for example, atrial fibrillation, bradycardia, tachycardia, pauses, asystole, ectopy, and/or the like.

Figure 4A:
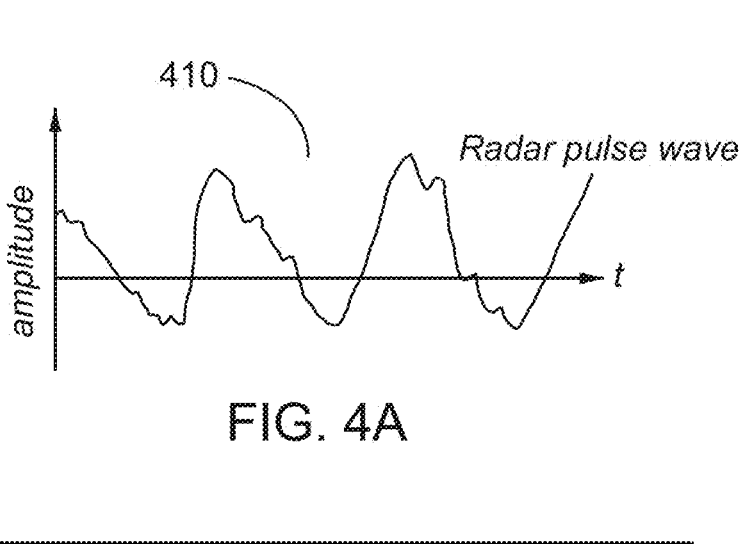

FIGS. 4A-B show example RF signal and example flowchart illustrating the process of detecting a patient's heart rate based on the RF signal using the RF-based monitoring device or sensor disclosed herein, according to some embodiments. In some embodiments, the basic operations of the beat detection algorithm based on the RF signal shown in FIG. 4A with reference 410 to the detection of the heart rate can be same or similar to those operations applied when determining the occurrence, or lack thereof, of the above-noted arrhythmic events. In some embodiments, these operations include identifying peaks of arterial pulse waveforms obtained from an analysis of signals reflected from an artery being monitored. In some embodiments, the peaks of the waveforms may be detected to obtain information on the ventricular inter-beat intervals (RR intervals) and/or differences between successive intervals ($\Delta$RR), since the peaks at least substantially correspond to ventricular contractions. For example, one may specify certain time windows and detect RR intervals that appear in these time windows. The arterial pulse waveform peaks, in some embodiments, also correspond to the R-peaks of electrocardiogram (ECG) measurements.

FIGS. 5A-B show example relationships between arterial pulse waveform peaks and R peaks of electrocardiogram (ECG) measurements, according to some embodiments. In these figures, the arterial pulse waveforms are obtained for depths (into the body of a patient) measuring about 2.4 cm, and the overlaps between the pulse waveforms and the ECG signals illustrate the relationship between the ECG R-peaks and the waveform peaks. In some embodiments, the RF measurements to obtain the arterial pulse waveforms may be performed for depths ranging from about 0.5 cm to about 10 cm, from about 1 cm to about 8 cm, from about 1.5 cm to about 6 cm, from about 2 cm to about 5 cm, including values and subranges therebetween.

The relationship with the ECG signal and arterial pulse waveform is shown to illustrate how the arterial pulse waveform may be used to detect cardiac abnormalities including abnormal cardiac rhythms alone, or in conjunction with the ECG signal. For example, the ECG signal may be used to determine an ongoing occurrence of an atrial fibrillation episode and may be confirmed via the arterial pulse waveform prior to establishing a treatment response. For instance, in a wearable cardioverter defibrillator, an ECG signal may initially determine that the patient is undergoing a ventricular fibrillation event, and if the arterial pulse waveform also confirms the event, the wearable defibrillator can respond to the event by delivering a defibrillation pulse. Prior to delivering the pulse, the device may initial an alert sequence to warn the patient of the impending shock.

Figure 5C:
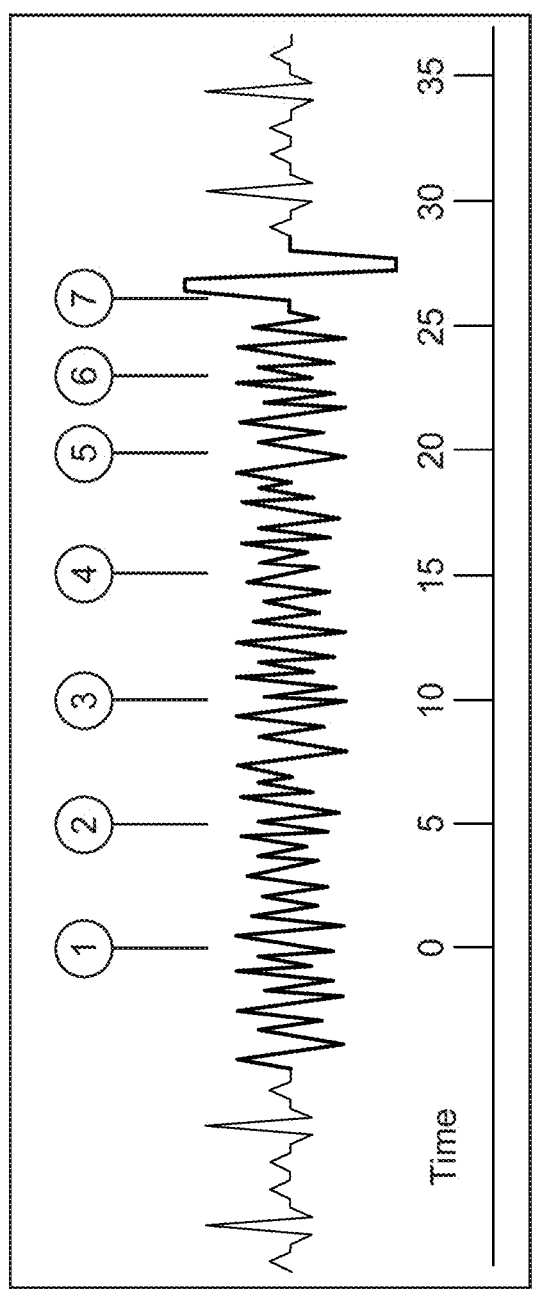
FIG. 5C shows a sample alert sequence generated by an example wearable cardioverter defibrillator of FIG. 3C, according to some embodiments.

As an example, consider the example alert sequence for a wearable cardioverter defibrillator shown in FIG. 5C. At point 1 of the treatment sequence, a ventricular fibrillation event may be detected via the ECG sensors of the device. For example, the ECG-based arrhythmia detection algorithm may use heart rate and morphology analysis to identify a ventricular fibrillation event. In addition, or in the event morphology analysis is not available, the device may use heart rate, vectorcardiogram stability, and frequency domain analysis of the ECG signal, along with predetermined and onset criteria to provide arrhythmia detection. Additional details can be found in U.S. Pat. No. 5,944,669, filed Nov. 20, 1997, titled "Apparatus and Method for Sensing Cardiac Function," the disclosure of which is incorporated by reference herein in its entirety. Between points 1 and 2, an RF-based device incorporated in the wearable defibrillator system can monitor the arterial pulse waveform and confirm the ventricular fibrillation event, e.g., by implementing an example process described in FIG. 5C below.

At point 2 (about 5 seconds after point 1), the wearable defibrillator can issue a first alert to the patient. For example, the first alert may be an audible alarm. In some examples at either point 1, or between points 1 and 2, the wearable defibrillator may initiate a vibration or tactile alert prior to issuing the first alert to the patient. At point 3 (about 10 seconds after point 1), the wearable defibrillator may initiate a second alert. For example, the second alert may be a louder alarm designed to draw the subject's attention. At point 4 (about 15 seconds after point 1), the wearable defibrillator may initiate a third alert. For example, the third alert may be an audible instruction to the patient and/or bystander: "Patient, push response buttons" and/or "Bystanders, please do not touch patient". At points 5-7, additional alerts may be delivered to the patient. In addition, at points 5-7, the defibrillator may take actions such as charging one or more capacitors, deploying a conductive gel over the therapy electrodes, and/or selecting treatment parameters for the shock to be delivered to the patient.

Additional discussion on the use of ECG measurements in conjunction with RF measurements to obtain clinical or medical information of patients such as blood pressure can be found in PCT International Application No. PCT/IL2015/050140, filed Feb. 5, 2015, titled "Systems, Apparatuses and Methods for Determining Blood Pressure," incorporated herein by reference in its entirety.

In some embodiments, the information obtained on inter-beat intervals may be evaluated with the aid of algorithms to detect the presence of a variety of arrhythmic events such as but not limited to atrial fibrillation, bradycardia, tachycardia, pauses, asystole, and ventricular ectopy. For example, the presence of atrial fibrillation may be detected by using methods discussed in, for example, the article "Automatic detection of atrial fibrillation using the coefficient of variation and density histograms of RR and DeltaRR intervals. K. Tateno, L. Glass, Medical & Biological Engineering & Computing, 2001, v.39, pp. 664-671," and U.S. Patent Publication No. 2015/0018693, filed Jul. 9, 2013, titled "Method And Apparatus For Monitoring A Subject For Atrial Fibrillation," both of which are incorporated herein by reference in their entireties.

FIGS. 4A-B show example RF signal and an example flowchart illustrating the process of detecting a patient's heart rate based on the RF signal using the RF-based monitoring device or sensor disclosed herein, according to some embodiments. The flowchart shows the operations of the beat detection algorithm based on the RF signal. In some embodiments, some or all of these operations can be used in determining the occurrence or absence of arrhythmic events in the patient. In some implementations, the beat detection algorithm can be broken down into two sections: filtration and beat detection rules. For example, with filtration, one or more filters can be implemented using circuit elements (e.g., low pass, high pass, bandpass and/or narrow band filter elements). Beat detection rules as illustrated below can be implemented in a series of instructions performed by the at least one controller (e.g., controller 208). In some embodiments, both functions can be implemented in code executed by the at least one controller 208. In this regard, the at least one controller 208 can be coded as follows. Assuming implementation in a high-level computer programming language (such as C, for instance), a first code file can be implemented as, for example, RFFiltering.c which contains the filter implementations (see portion of flow labeled RF filter algorithm, e.g., 416). A second code file can be implemented as, for example, RFPeakDetectionRules.c which contains the detection rules implementation (see portion of flow labeled RF pulse peak detection algorithm, e.g., 418). The example file names used here are for illustration purposes only.

For example, initially, a depth of an artery to be interrogated by the RF signals is identified, e.g., 412. For example, the arterial pulse waveforms can be obtained for depths measuring about 2.4 cm. As noted above, in some embodiments, RF measurements to obtain the arterial pulse waveforms may be performed for depths ranging from about 0.5 cm to about 10 cm, from about 1 cm to about 8 cm, from about 1.5 cm to about 6 cm, and from about 2 cm to about 5 cm, including values and subranges therebetween. In some embodiments, the system may focus on portions of this time-domain signal that occur at specific times, with these time locations corresponding to specific depths (e.g., depths or distances to the artery) within the patient's body. Next, using techniques described above, the RF signal corresponding to the identified depth can be isolated, e.g., 414. As noted previously, the reflected RF signals may have reflections from other objects and tissues within the patient's body. For example, the desired arterial radar signal may be identified based on selecting signals that are, for the selected depth, stronger than a predetermined threshold. The RF pulse signal 420 is input to the RF filter algorithm 416. In the RF filter algorithm 416, the code is designed to filter the RF signal to generate a windowed (e.g., time limited) estimate of the energy in the QRS frequency band. For example, this is achieved by low pass filtering 422 (e.g., around a predetermined cutoff, say 16 Hz of the RF signal), high pass filtering 424 (e.g., around another predetermined cutoff, say around 8 Hz of the RF signal), taking the derivative of the result and taking an absolute value of the signal, e.g., 426.

In some examples, the absolute value is averaged over the window (e.g., over an about 80 ms window), e.g., 428. Other window lengths are possible, e.g., about 40 ms, about 60 ms, about 100 ms, about 150 ms, about 180 ms, or more. In some embodiments, larger windows can allow for detection of premature ventricular contractions (PVCs) that have wider RF peak wave widths. A final filter output produces an indication corresponding to a detected peak signal in the RF wave. For example, the high pass, low pass, and derivative, can be combined to produce a bandpass filter with a pass band from, e.g. about 5 to about 11 Hz, roughly the bandwidth that contains most of the energy in the RF wave corresponding to the peak signal (corresponding to the QRS complex in an ECG signal). The averaging window can be selected to be roughly the width of a typical QRS complex.

After the signal has been filtered, the second code file RFPeakDetectionRules.c, can be called. This code is designed to detect peaks in the signal, e.g., 430. For example, each time a peak is detected the code can classify the signal as either an RF pulse or noise, or the signal can be saved for later classification. The code can use, for example, the peak height, location relative to a prior or last RF peak, and a maximum derivative to classify the peaks. For example, the below are example detection rules that can be implemented (one or more or all) in the second code file, e.g., 432:

Ignore all peaks that precede or follow larger peaks by less than about 200 ms.

If a peak occurs, check to see whether the raw signal contained both positive and negative slopes. If not, the peak represents a baseline shift.

If the peak occurred within about 360 ms of a previous detection check to see if the maximum derivative in the raw signal was at least half the maximum derivative of the previous detection. If not, the peak can be ignored or classified as noise.

If the peak is larger than the detection threshold call it an RF peak, otherwise call it noise.

If no RF peak has been detected within 1.5 peak-to-peak intervals (peak-peak intervals, also can be referred to as RR intervals), there was a peak that was larger than half the detection threshold, and the peak followed at least about 360 ms preceding detection by at least about 360 ms, classify that peak as a RF peak.

Determine peak-peak interval estimate. For example, this estimate may be an average, median, or mode peak-peak interval for a predetermined period of time (e.g., preceding 10 seconds, 15 seconds, 30 seconds, or more). and In some embodiments, the period of time can be user-configurable in advance or hard coded into the instructions. Other statistical measures for peak-peak intervals may be employed. For example, the peak-peak interval estimate used in step 5 above can be calculated as the median or mean of a predetermined most recent peak-peak intervals. For example, five, ten, two, thirty, or more of the most recent peak-peak intervals may be used. Once a peak-peak interval estimate has been determined, in some implementations, heart rate can be calculated 434 using the formula: 60/peak-peak interval estimate.

The detection threshold can be calculated using estimates of the RF peak and noise peak heights. For example, every time a peak is classified as an RF peak signal, the peak value can be added to a first buffer (e.g., stored in memory and accessible by the at least one 208) containing a predetermined most recent RF peak values. For example, the buffer may hold five, ten, two, thirty, or more of the last RF peak values that were calculated. Every time a peak occurs that is not classified as an RF peak signal, it can be added to a second buffer containing a predetermined most recent non-RF peak (e.g., noise peaks). For example, the second buffer may hold five, ten, two, thirty, or more of the last noise peak values that were calculated. The detection threshold can then be set between the mean or median of the noise peak(s) and the RF peak(s) buffers according to a predetermined formula. As an example, such a formula may be:

$$\text{Detection}_{Threshold} = \text{Average}_{Noise\ Peak} + \mu(\text{Average}_{RF\_Peak} - \text{Average}_{Noise\ peak}),$$

where $\mu$ is a user-configurable threshold coefficient (e.g., ranging from about 0 to about 1).

In some embodiments, with reference to FIG. 6, one of the methods for detecting atrial fibrillation may include the steps of analyzing the radar signals to detect peak-peak or RR interval values as discussed above with respect to the detection of the heart rate (e.g., FIGS. 4A-B). As previously described, initially, a depth of an artery to be interrogated by the RF signals is identified, e.g., step 602. For example, in some implementations, the RF measurements corresponding to depths ranging from about 0.5 cm to about 10 cm, from about 1 cm to about 8 cm, from about 1.5 cm to about 6 cm, from about 2 cm to about 5 cm, about 2.4 cm, including values and subranges therebetween, may be obtained. In some embodiments, the system may focus on portions of the time-domain signal that occur at specific times, with these time locations corresponding to the predetermined depths (e.g., depths or distances to the artery) within the patient's body. Next, the RF signal corresponding to the identified depth is isolated, e.g., step 604. Since, the reflected RF signals may have reflections from other objects and tissues within the patient's body, in some embodiments, the desired arterial radar signal may be identified based on selecting signals that are, for the selected depth, stronger than a predetermined threshold. Thereafter, the peaks of the arterial waveforms corresponding to the isolated RF signals can be determined, e.g., step 606, and then the ventricular interbeat or peak-peak (RR intervals) can be determined.

Further, in some embodiments, the analysis may further reveal differences between successive RR intervals, $\Delta RR$ values, e.g., step 608. $\Delta RR$ values may then be analyzed with respect to RR intervals to identify properties of the $\Delta RR$ values including a distribution, e.g., step 610. Based on this analysis, in some embodiments, the occurrence of atrial fibrillation can be determined, e.g., step 612. The analysis of the RR and/or $\Delta RR$ values may be performed per sliding window of length N centered about each beat. The RR and/or $\Delta RR$ values may be accumulated from chosen time windows of the arterial pulse waveforms based on the peaks of the waveforms, and the analysis of sequences of these RR and/or $\Delta RR$ values may be performed by considering the values as random variables. In some embodiments, a Kolmogorov-Smirnov test may be applied to the RR and $\Delta RR$ values to determine the probability that a set of $\Delta RR$ values over a window belong to a standard distribution about a mean value of the RR values over the same window. In some embodiments, if this probability value exceeds a threshold value (e.g., pre-defined threshold value), then the central beat and/or subsets of beat around the central beat can be interpreted as indications of atrial fibrillation.

In some embodiments, after an initial detection of an atrial fibrillation event as discussed above, the sensor may delay the reporting of the detected event until the event has lasted some duration (e.g., to ascertain that the detected event is in fact occurring and not a "glitch"). For example, this duration may be a predetermined configurable parameter ranging from one or more seconds, to about an hour, from about lmin to about 30 mins, from about 2 mins to about 15 mins, from about 3 mins to about 10 mins, about 5 mins, including values and subranges therebetween. In some embodiments, this parameter may be set to zero for immediate reporting of the occurrence of atrial fibrillation. In some embodiments, the sensor may delay the reporting of a detected atrial fibrillation event until after the event has lapsed by some duration, which may be same as or different from the aforementioned predetermined and configurable parameter (e.g., to ascertain that detection is not part of an ongoing event).

In some embodiments, accurate detection of the occurrence of atrial fibrillation events, in particular, when the events occur in repeated or excessive fashion, provides healthcare providers valuable insights into patients' related medical conditions. For example, measurement of regular (e.g., daily) atrial fibrillation events can be indicative of patient deterioration for CHF and other patients. As another example, the detection of frequent, regular and/or excessive atrial fibrillation events (e.g., occurrence of atrial fibrillation events for more than about an hour a day) can be associated with an increased risk of stroke and can be used as parameters for determining different levels of stroke risks. In some embodiments, healthcare providers may primarily consider the context in which asymptomatic, subclinical arrhythmias are detected (e.g., primary or secondary prevention of stroke and systemic embolism) and the risk profile of every individual patient in making patient prognosis and/or diagnosis.

In some embodiments, some patients may not show symptoms of atrial fibrillation, a condition known as asymptomatic atrial fibrillation, and in such patients, the detection of atrial fibrillation using the devices and methods disclosed herein can be highly valuable from at least a prognosis point of view. For example, asymptomatic atrial fibrillation patients can be monitored for a fixed amount of time (e.g., over about a 24 hr period to determine their "daily atrial fibrillation burden") and/or overall burden (e.g., over the entire monitoring period) and the information obtained from such observations may allow healthcare providers to make proper prognosis of the patients' medical conditions.

In some embodiments, the steps discussed above with reference to the detection of a patient's heart rate and atrial fibrillation events may also be used to determine the presence of other arrhythmic events such as but not limited to bradycardia, tachycardia, pauses, asystole, ectopy events and/or the like. For example, FIG. 7 shows example flowchart illustrating the process of detecting bradycardia using the RF-based monitoring device disclosed herein, according to some embodiments. Accordingly, in some embodiments, RF signals may be transmitted towards an artery by an RF monitoring device or sensor in proximity to the artery (e.g., an RF sensor worn on a wrist in proximity to the artery), and reflected signals may be processed to isolate those signals that are reflected by the artery. For example, as previously described, initially, a depth of an artery to be interrogated by the RF signals is identified, e.g., step 702. In some implementations, the RF measurements corresponding to depths ranging from about 0.5 cm to about 10 cms, from about 1 cm to about 8 cms, from about 1.5 cm to about 6 cms, from about 2 cm to about 5 cms, about 2.4 cms, including values and subranges therebetween, may be obtained. In some embodiments, the system may focus on portions of the time-domain signal that occur at specific times, with these time locations corresponding to the predetermined depths (e.g., depths or distances to the artery) within the patient's body. Next, the RF signal corresponding to the identified depth is isolated, e.g., step 704. Since, the reflected RF signals may have reflections from other objects and tissues within the patient's body, in some embodiments, the desired arterial radar signal may be identified based on selecting signals that are, for the selected depth, stronger than a predetermined threshold.

In some embodiments, these signals may be analyzed to determine the heart rate of the patient as discussed above with reference to FIGS. 4A-B, e.g., step 706. Further, the heart rate may then be compared with various threshold values to determine the occurrence of arrhythmic events in the patient, e.g., step 708. For example, if the heart rate is below a threshold heart rate, that may be identified as a bradycardic event. In some embodiments, the threshold heart rate may be a predetermined configurable value. For example, the threshold value can be in the range from about 20 beats per minute to about 60 beats per minute, from about 25 beats per minute to about 55 beats per minute, from about 30 beats per minute to about 50 beats per minute, about 40 beats per minute, including values and subranges therebetween. In some embodiments, the heart rate can be an average heart rate calculated over multiple heartbeats and/or several seconds. For example, the average may be calculated over about 15 beats, about 20 beats, about 25 beats, about 30 beats, etc., and/or over about 20 secs, about 25 secs, about 30 secs, about 35 secs, about 40 secs, etc.

In some embodiments, after the patient experiences bradycardic event, if the heart rate exceeds some threshold value (which may be the same or different from, i.e., larger than, the above threshold value for determining the onset of a bradycardic event), then that event may be characterized or identified as the patient exiting bradycardia, e.g., step 710. For example, the threshold value may be about 45 beats per minute, and the heart rate exceeding this threshold value may be understood as the end of the bradycardic event. In some embodiments, the threshold value can be in the range from about 30 beats per minute to about 60 beats per minute, from about 35 beats per minute to about 55 beats per minute, from about 40 beats per minute to about 50 beats per minute, about 45 beats per minute, including values and subranges therebetween. In some embodiments, the heart rate can be an average heart rate calculated over multiple heartbeats and/or several seconds. For example, the average may be calculated over about 15 beats, about 20 beats, about 25 beats, about 30 beats, etc., and/or over about 20 secs, about 25 secs, about 30 secs, about 35 secs, about 40 secs, etc.

In some embodiments, when the heart rate (or average heart rate) drops by some threshold amount (e.g., a predetermined configurable value) below the bradycardia onset threshold value (e.g., 40 beats per minute as discussed above), such an event may be identified and recorded as an event of bradycardia. In some embodiments, the threshold heart rate drop amount can be in the range from about 0 beats per minute to about 100 beats per minute, from about 1 beat per minute to about 50 beats per minute, from about 3 beats per minute to about 10 beats per minute, about 5 beats per minute, including values and subranges therebetween. In some embodiments, if the heart rate (or average heart rate) drops again by at least the threshold amount, then it may be considered as another event of bradycardia. However, a single heart rate (or average heart rate) drop by twice (or larger) the threshold amount would still be considered and recorded as a single event of bradycardia. In other words, in some embodiments, a single heart rate (or average heart rate) drop by the threshold amount below the bradycardia onset threshold value, regardless of the size of the drop, may still be identified and recorded as one event of bradycardia.

In additional or alternatively, the RF device may monitor for degradation into hemodynamically unstable bradycardia. As noted above, each particular patient may have a particular R-R interval and ECG QRS morphological characteristic that is indicative of hemodynamic compromise. Even on a same patient, the ECG may remain essentially the same as the patient degrades from hemodynamically stable to hemodynamically unstable bradycardia. If, for instance, a bradycardia has been detected using the ECG or RF-based R-wave detection as described above, the rate RF-based pulse pressure measurements may be increased, for instance from once every 5 minutes to once every 5 or 10 seconds. In such a fashion, the algorithm can more expeditiously detect such a hazardous degradation in hemodynamics. Additionally, after therapeutic pacing has been delivered, the RF-pulse detection or RF-based blood pressure measurements may be used to determine whether the shock or pacing has been effective in generating a hemodynamically viable return of circulation to the patient.

In some embodiments, if the heart rate is measured to be above a threshold heart rate, the event may be identified as a tachycardic event. FIG. 8 shows example flowchart illustrating the process of detecting tachycardia using one of the RF-based monitoring devices disclosed herein (according to some embodiments). Similar to the detection of bradycardia discussed above with reference to FIG. 7, in some embodiments, RF signals may be transmitted towards an artery by an RF monitoring device or sensor in proximity to the artery, and reflected signals may be processed to isolate those signals that are reflected by the artery. For example, as previously described, initially, a depth of an artery to be interrogated by the RF signals is identified, e.g., step 802. In some implementations, the RF measurements corresponding to depths ranging from about 0.5 cm to about 10 cm, from about 1 cm to about 8 cm, from about 1.5 cm to about 6 cm, from about 2 cm to about 5 cm, about 2.4 cm, including values and subranges therebetween, may be obtained. In some embodiments, the system may focus on portions of the time-domain signal that occur at specific times, with these time locations corresponding to the predetermined depths (e.g., depths or distances to the artery) within the patient's body. Next, the RF signal corresponding to the identified depth is isolated, e.g., step 804. Since, the reflected RF signals may have reflections from other objects and tissues within the patient's body, in some embodiments, the desired arterial radar signal may be identified based on selecting signals that are, for the selected depth, stronger than a predetermined threshold.

In some embodiments, these signals may be analyzed to determine the heart rate of the patient as discussed above with reference to FIGS. 4A-B, e.g., step 806. Further, the heart rate may then be compared with threshold values to determine the occurrence of tachycardia in the patient, e.g., step 808. In some embodiments, tachycardia may be considered to have occurred if the heart rate exceeds a heart rate threshold value. In some embodiments, this threshold value may be a predetermined configurable value. For example, the threshold value can be configured to be in the range from about 100 beats per minute to about 250 beats per minute, from about 110 beats per minute to about 200 beats per minute, from about 120 beats per minute to about 150 beats per minute, about 130 beats per minute, including values and subranges therebetween. In some embodiments, the heart rate can be an average heart rate calculated over multiple heartbeats and/or several seconds. For example, the average may be calculated over about 15 beats, about 20 beats, about 25 beats, about 30 beats, etc., and/or over about 20 secs, about 25 secs, about 30 secs, about 35 secs, about 40 secs, etc.

In some embodiments, after the patient experiences tachycardia, if the heart rate falls below some threshold value (which may be the same or different from, i.e., smaller than, the above threshold value for determining the onset of a tachycardic event), then that may be determined as the patient exiting tachycardia, e.g., step 810. For example, the threshold value may be about 110 beats per minute, and the heart rate falling below this threshold value may be understood as the end of the tachycardic event. In some embodiments, the threshold value can be in the range from about 100 beats per minute to about 250 beats per minute, from about 102 beats per minute to about 200 beats per minute, from about 105 beats per minute to about 150 beats per minute, about 110 beats per minute, including values and subranges therebetween. In some embodiments, the heart rate can be an average heart rate calculated over multiple heartbeats and/or several seconds. For example, the average may be calculated over about 15 beats, about 20 beats, about 25 beats, about 30 beats, etc., and/or over about 20 secs, about 25 secs, about 30 secs, about 35 secs, about 40 secs, etc.

In some embodiments, when the heart rate (or average heart rate) rises by some threshold amount (e.g., a predetermined configurable value) above the tachycardia onset threshold value (e.g., 130 beats per minute as discussed above), such an event may be identified and recorded as an event of tachycardia. In some embodiments, the threshold heart rate rise amount can be in the range from about 0 beats per minute to about 250 beats per minute, from about 1 beat per minute to about 150 beats per minute, from about 3 beats per minute to about 50 beats per minute, about 10 beats per minute, including values and subranges therebetween. In some embodiments, if the heart rate (or average heart rate) rises again by at least the threshold amount, then it may be considered as another event of tachycardia. However, a single heart rate (or average heart rate) rise by twice (or larger) the threshold amount would still be considered and recorded as a single event of tachycardia. In other words, in some embodiments, a single heart rate (or average heart rate) rise by the threshold amount above the tachycardia onset threshold value, regardless of the size of the rise, may still be identified and recorded as one event of tachycardia.

In addition, or alternatively, the RF device according to some embodiments, may monitor for degradation into hemodynamically unstable tachycardia. As noted above, each particular patient may have a particular R-R interval and ECG QRS morphological characteristic that is indicative of hemodynamic compromise. Even on a same patient, the ECG may remain essentially the same as the patient degrades from hemodynamically stable to hemodynamically unstable tachycardia. If, for instance, a tachycardia has been detected using the ECG or RF-based R-wave detection as described above, the rate RF-based pulse pressure measurements may be increased, for instance from once every 5 minutes to once every 5 or 10 seconds. In such a fashion, the algorithm can more expeditiously detect such a hazardous degradation in hemodynamics. Additionally, after therapeutic pacing has been delivered, the RF-pulse detection or RF-based blood pressure measurements may be used to determine whether the shock or pacing has been effective in generating a hemodynamically viable return of circulation to the patient.

In some embodiments, pauses in heartbeats and/or asystole can be other types of arrhythmic events to be detected by the RF sensor and methods disclosed herein. With reference to FIG. 9, in some embodiments, RF signals may be transmitted towards an artery by an RF monitoring device or sensor in proximity to the artery, and reflected signals may be processed to identify those signals that are reflected by the artery. For example, as previously described, initially, the depth of an artery to be interrogated by the RF signals is identified, e.g., step 902. In some implementations, RF measurements corresponding to depths ranging from about 0.5 cm to about 10 cm, from about 1 cm to about 8 cm, from about 1.5 cm to about 6 cm, from about 2 cm to about 5 cm, about 2.4 cm, including values and subranges therebetween, may be obtained. In some embodiments, the system may focus on portions of the time-domain signal that occur at specific times, with these time locations corresponding to the predetermined depths (e.g., depths or distances to the artery) within the patient's body. Next, the RF signal corresponding to the identified depth is isolated, e.g., step 904. Since, the reflected RF signals may have reflections from other objects and tissues within the patient's body, in some embodiments, the desired arterial radar signal may be identified based on selecting signals that are, for the selected depth, stronger than a predetermined threshold.

In some embodiments, these signals may be analyzed to determine the presence of signal peaks as discussed above with reference to FIG. 6, e.g., step 906. For example, a beat detection algorithm, such as the aforementioned algorithm may be utilized to filter the identified signals and detect any peaks thereto. In some embodiments, the algorithm may monitor the signals for a time duration to confirm the presence of asystole and/or a pause, e.g., step 908. For example, if the algorithm fails to detect a peak during a threshold duration, then the absence of a peak may be interpreted as an indication of a cardiac pause. Further, if the algorithm fails to detect any peak past the first threshold duration, then this absence may be viewed as an indication of the occurrence of an asystole, e.g., step 910. For example, the threshold duration can be in the range from about 3 to about 5 periods of typical RR interval lengths, from about 3 to about 10 periods of typical RR interval lengths, from about 3 to from about 15 periods of typical RR interval lengths, including values and subranges therebetween. As another example, the threshold duration can be from about 1.5 seconds to about 150 seconds, from about 1.8 seconds to about 100 seconds, from about 2 seconds to about 50 seconds, from about 2.5 seconds to about 10 seconds, from about 2.5 seconds to about 5 seconds, about 3 secs, including values and subranges therebetween.

In some embodiments, ventricular fibrillation events can be another type of arrhythmia events to be detected by the RF sensor and methods disclosed herein. For example, when a subject's heart is in ventricular fibrillation, there is not enough pressure generated within the heart to cause the aortic value to open. In such situations, there may not be any blood flow to the patient's arteries, and as such there may not be an arterial pulse waveform. In this regard, if the ECG signal of the patient is indicating the presence of a ventricular fibrillation event, and no peaks are determined in the arterial pulse waveform, then the processor implementing the ventricular fibrillation detection algorithm can declare that the subject is in ventricular fibrillation. With reference to FIG. 10, in some embodiments, RF signals may be transmitted towards an artery by an RF monitoring device or sensor in proximity to the artery, and reflected signals may be processed to identify those signals that are reflected by the artery. For example, as previously described, initially, the depth of an artery to be interrogated by the RF signals is identified, e.g., step 1002. In some implementations, RF measurements corresponding to depths ranging from about 0.5 cm to about 10 cms, from about 1 cm to about 8 cms, from about 1.5 cm to about 6 cm, from about 2 cm to about 5 cm, about 2.4 cm, including values and subranges therebetween, may be obtained. In some embodiments, the system may focus on portions of the time-domain signal that occur at specific times, with these time locations corresponding to the predetermined depths (e.g., depths or distances to the artery) within the patient's body. Next, the RF signal corresponding to the identified depth is isolated, e.g., step 1004. Since, the reflected RF signals may have reflections from other objects and tissues within the patient's body, in some embodiments, the desired arterial radar signal may be identified based on selecting signals that are, for the selected depth, stronger than a predetermined threshold.

In some embodiments, these signals may be analyzed to determine the presence or absence of signal peaks as discussed above with reference to FIG. 6, e.g., step 1006. For example, a beat detection algorithm, such as the aforementioned algorithm may be utilized to filter the identified signals and detect any peaks thereto. In some embodiments, the algorithm may monitor the signals for a predetermined threshold duration to confirm the presence or absence of peaks, e.g., step 1008. For example, if the algorithm fails to detect a peak during the predetermined threshold duration, then the absence of a peak may be interpreted as an indication of the occurrence of a ventricular fibrillation, e.g., step 1012. Further, in some embodiments, the determination of the occurrence of a ventricular fibrillation event may be corroborated by monitoring ECG signals for indications of same event, e.g., step 1010.

An RF-based device incorporated in a wearable defibrillator system, as described above can monitor the arterial pulse waveform and indicate a shockable rhythm, for example, by detecting a significant drop in RF-based pulse pressure. Although the description below uses pulse pressure as a metric for monitoring hemodynamic stability, other RF-based metrics can be used. For example, an RF-based blood pressure measure as determined herein can be used in place of or in combination with the pulse pressure. In some configurations, the drop in the pulse pressure that indicates a shockable rhythm can be greater than a predetermined limit, such as, greater than 5%, 10%, 20%, or 50%. For example, a parameter may be stored in a memory of the device indicating the predetermined pulse pressure drop. A caregiver, technician, or other health care professional may set the parameter prior to use by the patient. In examples, the device can have a default initial value, e.g., 10%. In some embodiments, the device can dynamically automatically adjust the parameter based on real-time monitoring of the patient.

In some cases, a patient's ECG rhythm may first degrade from a normal sinus into a hemodynamically stable (i.e., able to circulate enough oxygenated blood for a patient to remain conscious) ventricular tachycardia. At some point, however, the rhythm may degrade into a hemodynamically unstable ventricular tachycardia that is hazardous to the patient. In such a situation, the ECG signal alone may be incapable of detecting such a hazardous shift in the patient's condition. For instance, a patient's heart rate and morphology may remain essentially unchanged at a rate of 150 BPM and QRS width of 120 ms, but if there is a drop in heart contractility, the ECG signal may remain essentially unchanged while being, in its new state, unable to supply the needed oxygen to the patient's brain and vital organs. Using ECG alone to detect such a degradation may involve waiting for the ECG signal to degrade into either, for instance a more hazardous polymorphic ventricular tachycardia, or ventricular fibrillation, in which the hemodynamics are already compromised. If, for instance, a ventricular tachycardia has been detected using the ECG or RF-based R-wave detection as described below, the rate of RF-based pulse pressure measurements may be increased, for instance, from once every 5 minutes to once every 5 or 10 seconds. In such a fashion, the algorithm can more expeditiously detect such a hazardous degradation in hemodynamics. Additionally, after a therapeutic shock or pacing has been delivered, the RF-pulse may be used to determine whether the shock or pacing has been effective in generating a hemodynamically viable return of circulation to the patient.

For example, in the case of bradycardia arrhythmias, each particular patient may have a particular R-R interval and ECG QRS morphological characteristic that is indicative of hemodynamic compromise. Even on a same patient, the ECG may remain essentially the same as the patient degrades from hemodynamically stable to hemodynamically unstable bradycardia. If, for instance, a bradycardia has been detected using the ECG or RF-based R-wave detection as described in further detail below, the rate RF-based pulse pressure measurements may be increased, for instance from once every 5 minutes to once every 5 or 10 seconds. In such a fashion, the algorithm can more expeditiously detect such a hazardous degradation in hemodynamics. Additionally or alternatively, after therapeutic pacing has been delivered, the RF-pulse detection or RF-based blood pressure measurements may be used to determine whether the shock or pacing has been effective in generating a hemodynamically viable return of circulation to the patient.

A similar situation may also occur with tachycardia arrhythmias. For example, each particular patient may have a particular R-R interval and ECG QRS morphological characteristic that is indicative of hemodynamic compromise. Even on a same patient, the ECG may remain essentially the same as the patient degrades from hemodynamically stable to hemodynamically unstable tachycardia. If, for instance, a tachycardia has been detected using the ECG or RF-based R-wave detection as described in further detail below, the rate RF-based pulse pressure measurements may be increased, for instance from once every 5 minutes to once every 5 or 10 seconds. In such a fashion, the algorithm can more expeditiously detect such a hazardous degradation in hemodynamics. Additionally, after therapeutic pacing has been delivered, the RF-pulse detection or RF-based blood pressure measurements may be used to determine whether the shock or pacing has been effective in generating a hemodynamically viable return of circulation to the patient.

Figure 11:
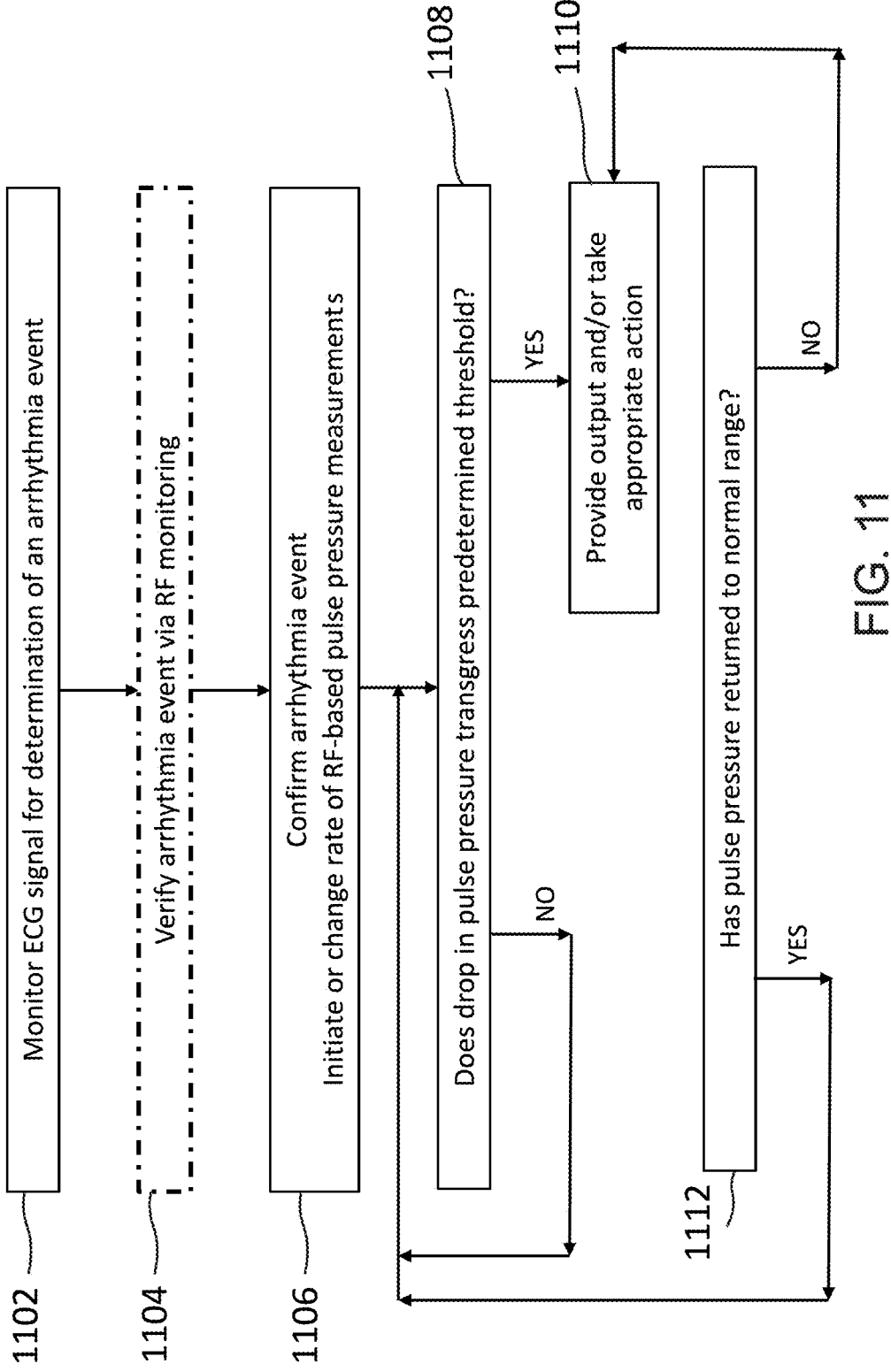
FIG. 11 shows example flowchart illustrating the use of the RF-based monitoring device disclosed herein to determine whether an arrhythmia condition has degraded to a hemodynamically unstable arrhythmia condition, according to some embodiments.

FIG. 11 shows an example flowchart that can be implemented by, for example, a wearable medical device, according to some embodiments, for determining whether an arrhythmia condition has degraded to a hemodynamically unstable arrhythmia condition. In some embodiments, the medical device can monitor the patient's ECG signal for a determination of an arrhythmia event, e.g., step 1102. For example, such arrhythmia events can include shockable ventricular tachycardia, or paceable arrhythmias such as bradycardia or tachycardia arrhythmias. Alternatively or additionally, in some embodiments, the medical device can verify the presence of the arrhythmia event via the one or more RF-based pulse measurements described herein, e.g., step 1104. For example, in the event of bradycardia, the device can monitor the patient's pulse via the RF-based techniques described in connection with FIG. 7. As another example, in the event of tachycardia, the device can monitor the patient's pulse via the RF-based techniques described in connection with FIG. 8.

Once an arrhythmia event has been confirmed, in some embodiments, RF-based pulse pressure measurements can be initiated, e.g., step 1106. Where RF-based pulse pressure measurements are already ongoing, a rate of the RF-based pulse pressure measurements may be increased, for instance, from once every 5 minutes to once every 5 or 10 seconds. In other examples, the rate can be changed to once every 3 seconds, 2 seconds, 1 second, or 500 ms. If the RF-based pulse pressure measurements transgress a threshold (e.g., indicates a drop in the pulse pressure below a predetermined threshold), e.g., step 1108, in some embodiments, the arrhythmia can be regarded to be a hemodynamically unstable arrhythmia. Otherwise, the arrhythmia is regarded to be hemodynamically stable and monitoring resumes as indicated. As described above, the predetermined threshold representing the drop in the pulse pressure can be set to be 5%, 10%, 20%, or 50%. Other threshold values are possible. For example, a parameter may be stored in a memory of the device indicating the predetermined pulse pressure drop. A caregiver, technician, or other health care professional may set the parameter prior to use by the patient. In examples, the device can have a default initial value, e.g., 10%. In some implementations, the device can dynamically automatically adjust the parameter based on real-time monitoring of the patient.

In some embodiments, one or more actions can be taken on determining that the arrhythmia is hemodynamically unstable, e.g., step 1110. For example, in a wearable defibrillation system, the device can initiate providing a defibrillation shock (e.g., where the arrhythmia is a shockable ventricular tachycardia) and/or providing one or more pacing pulses (e.g., where the arrhythmia is bradycardia or tachycardia) to the body of the patient. In some examples, a notification can be sent to a remote server indicating that the patient has suffered an arrhythmia. For example, a caregiver of the patient, a technician, or other designated person can be informed so that appropriate action can be taken. In some embodiments, e.g., step 1112, if after providing therapy to the patient, the patient's pulse pressure measurement returns to within a normal range (e.g., rises such that it no longer transgresses the threshold value), the device can determine that the therapy has been effective in generating a hemodynamically viable return of circulation to the patient. Otherwise, the device can continue to take the actions specified in step 1110, including continuing the provision of therapy to the patient.

Figure 12A:
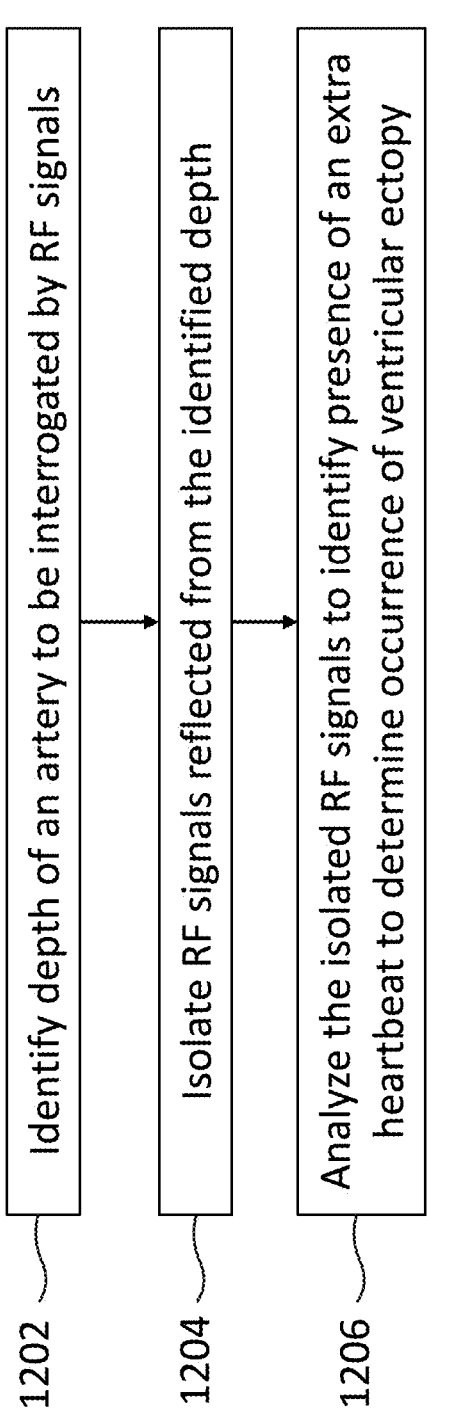
FIG. 12A shows example flowchart illustrating the process of detecting ventricular ectopy using the RF-based monitoring device disclosed herein, according to some embodiments.

In some embodiments, the monitoring of peaks in the RF signals, as discussed above with reference to FIG. 9, may indicate the presence of an extra heartbeat in the signals. For example, with reference to FIG. 12A, RF signals may be transmitted towards an artery by an RF monitoring device or sensor in proximity to the artery, and reflected signals may be processed to identify those signals that are reflected by the artery. For example, as previously described, initially, the depth of an artery to be interrogated by the RF signals is identified, e.g., step 1202. In some implementations, RF measurements corresponding to depths ranging from about 0.5 cm to about 10 cm, from about 1 cm to about 8 cm, from about 1.5 cm to about 6 cm, from about 2 cm to about 5 cm, about 2.4 cm, including values and subranges therebetween, may be obtained. In some embodiments, the system may focus on portions of the time-domain signal that occur at specific times, with these time locations corresponding to the predetermined depths (e.g., depths or distances to the artery) within the patient's body. Next, the RF signal corresponding to the identified depth is isolated, e.g., step 1204. Since, the reflected RF signals may have reflections from other objects and tissues within the patient's body, in some embodiments, the desired arterial radar signal may be identified based on selecting signals that are, for the selected depth, stronger than a predetermined threshold.

Figure 12B:
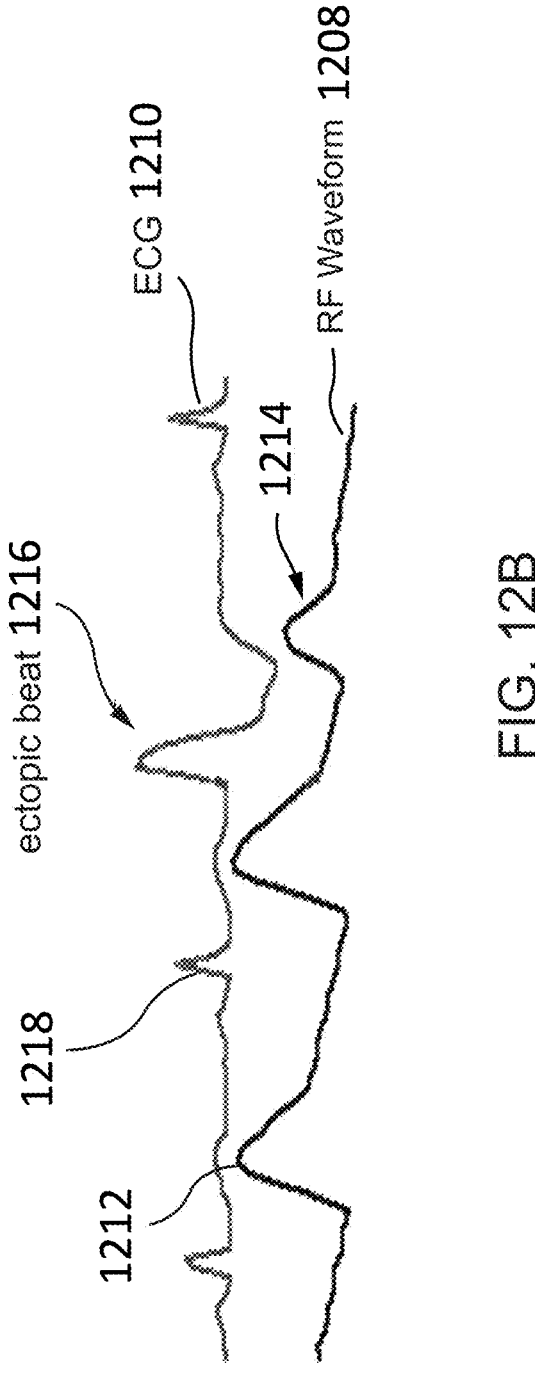
FIG. 12B shows an example image of RF signals obtained via the RF-based monitoring device disclosed herein and ECG signals illustrating the occurrence of ventricular ectopy, according to some embodiments.

In some embodiments, an analysis of the signals 1206 to determine the presence of signal peaks as discussed above with reference to FIGS. 4A-B, may indicate the presence of an extra peak in the signals, indicating the occurrence of ventricular ectopy in the patient. FIG. 12B shows an example image of an RF signal 1208 obtained via the RF-based monitoring device disclosed herein and compared with ECG signal 1210 for illustration, according to some embodiments. The image shows regularly spaced peaks 1212 indicating a normal or regular heartbeat rhythm interjected with an extra beat 1214 indicating an episode of ventricular ectopy in the patient. In such embodiments, the extra beat 1216 amongst the regularly spaced peaks 1218 of the ECG signals 1210 also confirms the occurrence of a ventricular ectopy event observed from the RF signals 1208. In ectopic episodes, in some embodiments, the patient can experience a compensatory pause before returning to normal rhythm after the ectopy.

In some embodiments, the RF-based monitoring device and methods disclosed herein can be used to determine the blood pressure of a patient wearing the device or sensor. With reference to FIGS. 13A-B, in some embodiments, the device/sensor may comprise two ends at which one or more RF antennas are located, the two ends defining an interrogation zone 1314 for monitoring the arteries located within the zone, e.g., step 1302. For example, the device may have a tubular structure as shown in FIG. 1B, which facilitates the wearability of the sensors on the body of patients in proximity to arteries 1316 (e.g., at wrists, ankles, etc.). In some embodiments, one or more RF antennas 1310 and 1312 may be located at the two ends of the device, each antenna containing a transmitter and a receiver. In such embodiments, the one or more antennas 1310, 1312 may be synchronized, and can be used to measure a pulse transit time as a pulse traveling through an artery of a patient enters the interrogation zone past one of the two ends and exits the zone past the other end, e.g., step 1304. For example, each RF antenna 1310, 1312 may transmit RF signals towards the artery and receive reflections therefrom, and these signals may be processed to determine/estimate the pulse transit time in the artery, e.g., step 1306, from which the blood pressure, and/or changes thereof, of the patient can be deduced, as detailed below, e.g., step 1308. In embodiments where there are a plurality of antennas at one or both of the ends 1310, 1312 (e.g., cyclic antenna arrays), the channels from which the signals slated for further processing are obtained may be those channels that produce the strongest and/or clearest signals.

Referring to FIG. 13B, an example implementation of the patient worn RF-based monitoring device is shown. In this implementation, the monitoring device has a tubular structure as shown and is configured to be worn around the lower portion of the subject's arm 1318. As shown, one or more entry RF antennas RF1 1310 are located at an upper end of the device and one or more exit RF antennas RF2 1312 are located at a lower end of the device. For example, each of the entry and exit RF antennas RF1 1310 and RF2 1312 can be controlled by a controller (e.g., controller 208 of FIG. 2A).

A pulse wave velocity (PWV) corresponds, for example, to a velocity of propagation of an arterial pulse waveform between points along the arterial tree, which may depend on, amongst other things, the blood pressure. A pulse transit time (PTT) corresponds, for example, to time taken for an arterial pulse waveform to propagate through a length of the arterial tree. As noted above, the arterial pulse waveform result from an ejection of blood from the left ventricle that may then move with a velocity greater than a forward movement of the blood itself. A pulse arrival time (PAT) corresponds, for example, to a time interval between the R-wave of the QRS complex in an electrocardiogram (ECG) signal of the patient and a particular point in the arterial pulse waveform recorded at the distal artery. In some embodiments, a length of this time interval may be inversely and non-linearly related to arterial stiffness: the shorter the PAT, the stiffer the arteries. For example, there may be a delay between the generation of the pulse by the ventricular muscle and the opening of the aortic valve.

In some embodiments, when using sensors such as an electrocardiogram (ECG) device, the PAT may correspond to the delay between the ECG's QRS peak (e.g., R-peak) and a point on the PPG signal representing the pressure pulse at the distal artery. PAT measured from the heart to the foot can include the time needed for the pulse wave to travel through two different arterial paths: one from the heart to the femoral artery (central path) and another from the femoral to the plantar artery (peripheral path). This way, PAT provides information about both central and peripheral arterial stiffness. In some instances, techniques here include determining an R-peak of the ECG waveform, and determining a time difference between the pulse arrival time (PAT) and the R-peak to determine a pre-ejection period (PEP). The PEP, in some embodiments, includes a duration between the ventricular polarization and the opening of the aortic valve. In some embodiments, this duration corresponds to time taken for the myocardium to raise sufficient pressure to open the aortic valve and start pushing blood out of the ventricle. In some instances, the effects of the PEP may be significant in determining blood pressure levels. In some cases, the processor may calculate PTT by subtracting PEP from PAT.

In some embodiments, the PTT to some point along the arterial tree (e.g., peripheral location in the arterial system) may be represented as the difference between the arrival time of the pulse at the point and the pre-ejection period, i.e., PTT=PAT–PEP. Upon determining or estimating the PTT, in some embodiments, the PWV may then be calculated based on the distance the pulse traveled to arrive at the point and the estimated/determined PTT. For example, in the embodiment of FIG. 13B, the PWV=distance between the antenna(s) RF1 1310 and antenna(s) RF2 1312 (shown as the interrogation zone 1314 with distance d) divided by the PTT. For example, the distance d can:

be between approximately 1 cm to approximately 30 cm, be between approximately 30 cm to approximately 50 cm; or be between about 50 cm to around 90 cm (e.g., span a length of the patient's forearm, span the entire length of an arm of the patient).

Accordingly, in some embodiments, the device can be variably adjusted to a desired suitable length during an initial fitting of the device on the patient. In such embodiments, a wrist worn device may be comprised of a compression fabric material that can be formed to fit about the patient's arm. For example, the compression fabric can be stretched or shortened so as to change the relative distance d between the two sets of antennas RF1 1310 and RF2 1312. While the distance d is described in this embodiment in connection with a wrist worn or forearm worn device, it is understood that the device can likewise be adapted for wear and similar operation about another portion of the patient's body. For example, the device may be adapted for similar wear and operation about a patient's leg (e.g., a lower extremity or ankle). For example, where the device is worn about the patient's leg, the distance d can be configured to span a portion or an entire length of the leg; e.g., the distance d can be at least one of: between about 1 cm and 30 cm, between about 30 cm and 50 cm, between about 50 cm and 90 cm, and between about 90 cm and 200 cm.

Alternatively, if the PWV is known, the PTT=PWV×d. In some implementations, blood pressure values such as systolic and/or diastolic values can be determined non-invasively from the PWV and/or the PTT. For example, linear transformations relating the systolic blood pressure (SBP) and diastolic blood pressure (DBP) to the PTT may be expressed as follows:

$$SBP=(a{\times}PTT)+b,$$

$$DBP=(c{\times}PTT)+d,$$

where the coefficients a, b, c and d can be calibrated for each patient based on an initial calibration phase.

For example, such an initial calibration phase may be during an initial fitting of the device to the patient. In other examples, average calibrations taken from a predetermined plurality of prior patient records may be used to determine the coefficients for a patient. In such cases, predictive algorithms such as machine learning and/or artificial neural network algorithms may be used to determine patients whose medical history, demographics, and other physiological profile closely matches the patient in question being fitted with the device. In some embodiments, other types of transformations may be used to calculate blood pressures. For example, for a model that assumes constant artery thickness and radius, blood pressure P may be expressed as P=a×ln(PTT)+b, where, again a and b are constants to be calibrated for each patient or derived from prior patient records. In any case, in some embodiments, obtaining PTT, or conversely PWV of a pulse in an artery, may lead to the determination of blood pressure levels in the artery.

As previously noted, pulse wave velocity (PWV) intrinsically varies with blood pressure. The PWV can be linked to the blood pressure through the concept of arterial compliance. Arterial compliance is a measure of an increase in volume that occurs in the artery when the pressure in that artery is increased. The tendency of the artery to stretch in response to pressure has a large effect on perfusion and blood pressure. This physically means that arteries with a higher compliance deform easier than lower compliance blood vessels under the same pressure and volume conditions. Accordingly, arterial compliance is given by ΔP/ΔV, where ΔV is the change in volume (mL), and ΔP is the change in pressure (e.g., units may be mm of mercury or mmHg)

The Bramwell-Hill equation reproduced below, provides an expression for PWV in terms of arterial compliance, blood mass density and (diastolic) volume V.

$$PWV = \sqrt{\frac{dP \cdot V}{\rho \cdot dV}}$$

As shown, PWV increases with pressure for at least two reasons. Arterial compliance decreases with increasing pressure due to the curvilinear relationship between arterial pressure and volume, and volume V increases with increasing pressure (e.g., due to artery dilation), directly increasing PWV. In some implementations, PWV can be considered dependent on blood pressure at a rate of approximately 1 m/s per 10 mmHg. That is, for every change of 1 m/s of PWV, the blood pressure may be considered to have changed by about 10 mmHg.

For example, the timing of the blood pressure measurements may be determined based on the time specified in seconds, minutes, or even hours, or a number of pulses. For example, this time can be specified during initial configuration of the device as a preset parameter. For example, this parameter can be set by caregiver, technician, other health care professional, or the user of the device. For example, the blood pressure measurement may be determined at least once every minute (60 seconds) over a duration of use of the device. In some embodiments, the blood pressure measure may be determined at least once every 45 seconds, every 30 seconds, every 15 seconds, or every 5 seconds over the duration. For example, the blood pressure measure can be determined at least once every: 500 milliseconds, 1 second, 2 seconds, 10 seconds, 30 seconds, 1 minute, 2 minutes, 5 minutes, 10 minutes, or 30 minutes.

In some embodiments, the blood pressure measure may be determined on a pulse peak to pulse peak basis of the RF waveform. For instance, the blood pressure measure may be determined on a pulse to pulse or beat to beat basis. Accordingly, a blood pressure measure may be determined from a first blood pressure measure taken at a first pulse to a second, different measure taken at a second, subsequent pulse of the patient. A duration between the first pulse and the second, subsequent pulse can be predetermined as an established value (e.g., 1 pulse, 2 pulses, 3 pulses, 5 pulses, 10 pulses, or more). In some cases, the number of pulses between measurements may be up to 25 pulses. In some cases, the number of pulses between measurements may be up to 50 pulses, 100 pulses, 200 pulses, 500 pulses, or 1000 pulses. Other numbers of pulses are possible and can be set by a caregiver, technician, other health care professional, or the user of the device. Additional information regarding the use of the pulse transit time and/or the pulse wave velocity for determining blood measures can be found in, for example, as discussed in PCT International Publication No. WO/2015/118544, filed Feb. 5, 2015, titled "Systems, Apparatuses and Methods for Determining Blood Pressure," incorporated herein by reference in its entirety.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims, equivalents thereto, and any claims supported by the present disclosure, inventive embodiments may be practiced otherwise than as specifically described and claimed. Inventive embodiments of the present disclosure are directed to each individual feature, system, article, material, kit, method, and step, described herein. In addition, any combination of two or more such features, systems, articles, materials, kits, methods, and steps, if such features, systems, articles, materials, kits, methods, and steps, are not mutually inconsistent, is included within the inventive scope of the present disclosure. Embodiments disclosed herein may also be combined with one or more features, as well as complete systems, devices and/or methods, to yield yet other embodiments and inventions. Moreover, some embodiments, may be distinguishable from the prior art by specifically lacking one and/or another feature disclosed in the particular prior art reference(s); i.e., claims to some embodiments may be distinguishable from the prior art by including one or more negative limitations.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed:

1. A physiological monitoring device comprising:
at least one electrocardiogram (ECG) electrode configured to detect ECG signals of a subject;
at least one antenna and associated circuitry configured to direct arrhythmia-detection radio-frequency (RF) waves in a range from about 100 MHz to about 5 GHz towards an artery to be interrogated which is located within a tissue of the subject at a predetermined depth beneath skin of the subject and receive reflected RF waves from the predetermined depth beneath the skin of the subject that are reflected by the artery; and
circuitry comprising at least one controller and configured to:
receive and process the ECG signals detected by the at least one ECG electrode,
monitor the received ECG signals to identify an occurrence or absence of at least one arrhythmia condition of the subject, the at least one arrhythmia condition comprising at least one of: ventricular ectopic-beats (VEB), ventricular runs, ventricular tachycardia, ventricular fibrillation, atrial fibrillation, bradycardia, or tachycardia,
based on the identification of the occurrence of the at least one arrhythmia condition from the received ECG signals, control the at least one antenna and associated circuitry to at least one of initiate generation and transmission of the arrythmia-detection RF waves towards the artery at the predetermined depth beneath the skin of the subject or change a pulse rate that the arrhythmia-detection RF waves are generated and transmitted to the artery at the predetermined depth beneath the skin of the subject, as the arrhythmia-detection RF waves are being generated and transmitted to the artery at the predetermined depth beneath the skin of the subject, control the at least one antenna and associated circuitry to receive the reflected RF waves from the predetermined depth that are reflected by the artery, process the reflected RF waves into RF signals corresponding to the reflected RF waves for a time period following the identified occurrence of the at least one arrhythmia event, determine the heart-rate of the subject by analyzing the RF signals to classify RF peaks in a waveform representative of a time varying radar cross-section (RCS) of the artery over a duration of time, wherein intervals between the RF peaks in the waveform representative of the time varying RCS of the artery over the duration of time correlate to the heart-rate of the subject, using the heart rate determined by analyzing the RF signals, confirm the occurrence of the at least one arrhythmia condition of the subject, the at least one arrhythmia condition comprising at least one of: the ventricular ectopic-beats (VEB), the ventricular runs, the ventricular tachycardia, the ventricular fibrillation, the atrial fibrillation, the bradycardia, or the tachycardia, and output at least one of an alert or a signal corresponding to the identified occurrence of at least one arrhythmia condition when the occurrence of the at least one arrhythmia condition is confirmed based on the heart rate determined by the analysis of the RF signals.

2. The device of claim 1, further comprising a housing configured for removable attachment to or proximate skin of the subject, wherein the at least one antenna is arranged on the housing.

3. The device of claim 2, further comprising a metallic cover disposed within the housing for shielding the at least one ECG electrode from the arrhythmia-detection RF waves directed by the at least one antenna and associated circuitry.

4. The device of claim 1, wherein the at least one controller is configured to identify the reflected RF waves from the predetermined depth beneath the skin by selecting the reflected RF waves having highest pulsating amplitudes of the corresponding RF signals from a plurality of reflected RF waves from different depths beneath the skin of the subject.

5. The device of claim 1, wherein the at least one controller is configured to determine a plurality of RR intervals based on the classified RF peaks, and to analyze sequences of RR intervals and heart rate variability (ΔRR) values based on the plurality of RR intervals to determine atrial fibrillation in the subject.

6. The device of claim 1, further comprising an attachment mechanism for removably attaching the device to or proximate to skin of the subject, wherein the attachment mechanism comprises at least one of: a vest, a garment, a wrist strap, a bracelet, a patch, or a chest strap.

7. The device of claim 1, wherein the confirmation of the occurrence of the at least one arrhythmia condition occurs at an established interval, wherein the established interval comprises at least one of once: every 90 seconds, every 60 seconds, every 45 seconds, every 30 seconds, every 15 seconds, or every 5 seconds.

8. The device of claim 7, wherein the established interval is set by a user-configurable parameter stored in a memory of the device.

9. The device of claim 7, wherein the established interval comprises a duration between a first pulse and a second pulse of the subject.

10. The device of claim 1, wherein the circuitry is configured to control the at least one antenna to emit frequencies in one or more ranges from about 100 MHz to about 1 GHz, about 200 MHz to about 2.5 GHZ, about 200 MHz to about 3 GHZ, or about 500 MHz to about 5 GHz.

11. The device of claim 1, wherein the circuitry is configured to monitor the received ECG signals to identify the occurrence or absence of all of: the ventricular ectopic-beats (VEB), the ventricular runs, the ventricular tachycardia, the ventricular fibrillation, the atrial fibrillation, the bradycardia, and the tachycardia.

12. The device of claim 1, wherein the associated circuitry that directs the arrhythmia-detection RF waves towards the artery within the tissue of the subject comprises a ground that is separate from a ground of the circuitry comprising the at least one controller.

13. The device of claim 1, wherein following confirmation of the occurrence of the at least one arrhythmia condition, the circuitry is configured to determine an RF based pulse pressure measurement based on the RF signals, and wherein the output signal comprises the determined pulse pressure measurement.

14. The device of claim 1, wherein, upon identification of the occurrence of the at least one arrhythmia condition of the subject, the circuitry is configured to increase the pulse rate that the arrhythmia-detection RF waves are generated and transmitted to the artery from one pulse every 5 minutes or longer to one pulse every 10 seconds or less.

15. The device of claim 1, wherein the circuitry is further configured to determine whether the identified at least one arrhythmia condition of the subject has degraded to a hemodynamically unstable condition based on analysis of the RF signals.

16. The device of claim 15, wherein the circuitry is further configured to output an additional alert or signal when the identified at least one arrhythmia condition of the subject becomes hemodynamically unstable.

17. A physiological monitoring system comprising:
a physiological monitoring device comprising:
at least one ECG electrode configured to detect ECG signals of a subject;
at least one antenna and associated circuitry configured to direct arrhythmia-detection radio-frequency (RF) waves in a range from about 100 MHz to about 5 GHz towards an artery to be interrogated which is located within a tissue of the subject at a predetermined depth beneath skin of the subject and receive reflected RF waves from the predetermined depth beneath the skin of the subject that are reflected by the artery;
device circuitry comprising at least one controller and electrically coupled to the at least one antenna, the device circuitry being configured to:
receive and process the ECG signals detected by the at least one ECG electrode,
control generation and transmission of the arrhythmia-detection RF waves towards the artery at the predetermined depth beneath the skin of the subject,
as the arrhythmia-detection RF waves are being generated and transmitted to the artery at the predetermined depth beneath the skin of the subject, control the at least one antenna and associated circuitry to receive the reflected RF waves from the predetermined depth that are reflected by the artery, and process the reflected RF waves into RF signals corresponding to the reflected RF waves, and communications circuitry configured for wired or wireless transmission of the RF signals and the received ECG signals to an external entity; and a remote processing server comprising server circuitry configured to:

monitor the received ECG signals to identify an occurrence or absence of at least one arrhythmia condition of the subject, the at least one arrhythmia condition comprising at least one of: ventricular ectopic-beats (VEB), ventricular runs, ventricular tachycardia, ventricular fibrillation, atrial fibrillation, bradycardia, or tachycardia, based on the identification of the occurrence of the at least one arrhythmia condition from the received ECG signals, identify RF signals corresponding in time to the identified occurrence of the at least one arrhythmia condition, analyze the identified RF signals that correspond in time to the identified occurrence of the at least one arrhythmia condition to determine a heart-rate of a subject for a duration of time corresponding to the identified occurrence of the at least one arrhythmia condition, wherein the analysis of the identified RF signals comprises classifying RF peaks in a waveform representative of a time varying radar cross-section (RCS) of the artery over the duration of time, and wherein intervals between the RF peaks in the waveform representative of the time varying RCS of the artery over the duration of time correlate to the heart-rate of the subject;

using the heart-rate determined via the analysis of the identified RF signals, confirm the occurrence of at least one arrhythmia condition of the subject, the at least one arrhythmia condition comprising at least one of: the ventricular ectopic-beats (VEB), the ventricular runs, the ventricular tachycardia, the ventricular fibrillation, the atrial fibrillation, the bradycardia, or the tachycardia; and output at least one of an alert or a signal corresponding to the identified occurrence of the at least one arrhythmia condition when the occurrence of the at least one arrhythmia condition is confirmed based on the heart rate determined by the analysis of the identified RF signals.

18. The system of claim 17, further comprising a therapy device configured to deliver at least one therapeutic shock to the subject, wherein the device circuitry of the arrhythmia monitoring device is configured to cease receiving the ECG signals and to initiate monitoring of the subject using the RF signals when the therapy device delivers the at least one therapeutic shock to the subject.

19. The system of claim 18, wherein the therapeutic shock comprises at least one of pacing, defibrillation, or transcutaneous electrical nerve stimulation (TENS) pulses.

20. The system of claim 17, further comprising at least one movement sensor configured to measure motion data representative of movement of the subject, wherein the communications circuitry of the arrhythmia monitoring device is configured for wired or wireless transmission of the motion data to the remote processing server, and wherein the confirmation of the occurrence of the at least one arrhythmia condition of the subject by the server circuitry of the remote processing server is further based, in part, on the motion data.

* * * * *